(12) United States Patent
Clark et al.

(10) Patent No.: US 12,305,168 B2
(45) Date of Patent: May 20, 2025

(54) MATERIALS AND METHODS FOR EFFICIENT TARGETED KNOCK IN OR GENE REPLACEMENT

(71) Applicants: Mayo Foundation for Medical Education and Research, Rochester, MN (US); Iowa State University Research Foundation, Inc., Ames, IA (US)

(72) Inventors: Karl J. Clark, Rochester, MN (US); Stephen C. Ekker, Rochester, MN (US); Jeffrey Essner, Ames, IA (US); Jordan Michael Welker, Ames, IA (US); Maira Pedroso de Almeida, Ames, IA (US); Wesley Allen Wierson, Ames, IA (US); Maura McGrail, Ames, IA (US)

(73) Assignees: Mayo Foundation for Medical Education and Research, Rochester, MN (US); Iowa State University Research Foundation, Inc., Ames, IA (US)

( * ) Notice: Subject to any disclaimer, the term of this patent is extended or adjusted under 35 U.S.C. 154(b) by 664 days.

(21) Appl. No.: 16/630,158

(22) PCT Filed: Jul. 12, 2018

(86) PCT No.: PCT/US2018/041888
§ 371 (c)(1),
(2) Date: Jan. 10, 2020

(87) PCT Pub. No.: WO2019/014489
PCT Pub. Date: Jan. 17, 2019

(65) Prior Publication Data
US 2020/0208146 A1    Jul. 2, 2020

Related U.S. Application Data

(60) Provisional application No. 62/531,673, filed on Jul. 12, 2017.

(51) Int. Cl.
*C12N 15/11* (2006.01)
*C12N 9/22* (2006.01)
*C12N 15/85* (2006.01)

(52) U.S. Cl.
CPC ............ *C12N 15/11* (2013.01); *C12N 9/22* (2013.01); *C12N 15/85* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 8,586,363 B2 | 11/2013 | Voytas et al. |
| 2015/0376628 A1 | 12/2015 | Schoenherr et al. |
| 2015/0376650 A1 | 12/2015 | Auerbach et al. |
| 2015/0376651 A1 | 12/2015 | Frendewey et al. |
| 2016/0108381 A1 | 4/2016 | Lee et al. |
| 2017/0076039 A1 | 3/2017 | Kim et al. |
| 2017/0335300 A1 | 11/2017 | Frisch et al. |
| 2018/0208945 A1 | 7/2018 | Bao et al. |
| 2018/0334685 A1 | 11/2018 | Yeo et al. |
| 2019/0002920 A1 | 1/2019 | Sherwood et al. |

FOREIGN PATENT DOCUMENTS

| CN | 106834320 | 6/2017 |
| GB | 2531454 | 4/2016 |
| WO | WO 2016025759 | 2/2016 |
| WO | WO 2017096041 | 6/2017 |

OTHER PUBLICATIONS

Hisano, Precise in-frame integration of exogenous DNA mediated by CRISPR/Cas9 system in zebrafish, Nature, Article No. 8841, 2015 (Year: 2015).*
National Center for Biotechnology Information (2022). PubChem Pathway Summary for Pathway R-HSA-5693538, Homology Directed Repair, Source: Reactome. Retrieved Nov. 23, 2022 (Year: 2022).*
Hisano, Yu, et al. "Precise in-frame integration of exogenous DNA mediated by CRISPR/Cas9 system in zebrafish." Scientific reports 5.1 (2015): 8841. (Year: 2015).*
Lesueur, Léa L., Lluis M. Mir, and Franck M. André. "Overcoming the specific toxicity of large plasmids electrotransfer in primary cells in vitro." Molecular Therapy-Nucleic Acids 5 (2016). (Year: 2016).*
Schwartz, Matthew L., and Erik M. Jorgensen. "SapTrap, a toolkit for high-throughput CRISPR/Cas9 gene modification in Caenorhabditis elegans." Genetics 202.4 (2016): 1277-1288. (Year: 2016).*
Zhang, Jian-Ping, et al. "Efficient precise knockin with a double cut HDR donor after CRISPR/Cas9-mediated double-stranded DNA cleavage." Genome biology 18.1 (2017): 1-18. (Year: 2017).*
Hisano, Yu, et al. "Precise in-frame integration of exogenous DNA mediated by CRISPR/Cas9 system in zebrafish." Scientific reports 5.1 (2015): 1-7. (Year: 2015).*
Aida et al., "Gene cassette knock-in in mammalian cells and zygotes by enhanced MMEJ," BMC Genomics, 17(1):979, Nov. 28, 2016, 18 pages.
Bedell et al., "In vivo genome editing using a high-efficiency TALEN system," Nature, 491(7422): 114-118, Sep. 23, 2012.
Beumer et al., "Efficient gene targeting in *Drosophila* by direct embryo injection with zinc-finger nucleases," Proc. Natl. Acad. Sci. USA, 105(50):19821-19826, Dec. 16, 2008.
Carlson et al., "Efficient TALEN-mediated gene knockout in livestock," Proc. Natl. Acad. Sci. USA, 109(43):17382-17387, Oct. 23, 2012.

(Continued)

*Primary Examiner* — Weihua Fan
*Assistant Examiner* — Brian James Sullivan
(74) *Attorney, Agent, or Firm* — Fish & Richardson P.C.

(57) ABSTRACT

Materials and methods for generating targeted knock ins and gene replacements with high precision and efficiency are provided herein.

12 Claims, 33 Drawing Sheets

Specification includes a Sequence Listing.

(56) References Cited

OTHER PUBLICATIONS

Ceccaldi et al., "Repair Pathway Choices and Consequences at the Double-Strand Break," Trends Cell Biology, 26(1):52-64, Jan. 2016.
Geurts et al., "Knockout rats via embryo microinjection of zinc-finger nucleases," Science, 325(5939):433, Jul. 24, 2009.
Hasty et al., "Target frequency and integration pattern for insertion and replacement vectors in embryonic stem cells," Mol. Cell Biology, 11(9):4509-4517, Sep. 1991.
Hoshijima et al., "Precise Editing of the Zebrafish Genome Made Simple and Efficient," Dev. Cell, 36(6):654-667, Mar. 21, 2016.
Makarova et al., "Evolution and classification of the CRISPR-Cas systems," Nat. Rev. Microbiology, 9(6):467-477, May 9, 2011.
Orr-Weaver et al., "Yeast transformation: a model system for the study of recombination," Proc. Natl. Acad. Sci. USA, 78(10):6354-6358, Oct. 1981.
Rong et al., "Gene targeting by homologous recombination in *Drosophila*," Science, 288(5473):2013-2018, Jun. 16, 2000.
Shin et al., "Efficient homologous recombination-mediated genome engineering in zebrafish using TALE nucleases," Development, 141(19):3807-3818, Oct. 2014.
Wierson et al., "Efficient targeted integration directed by short homology in zebrafish and mammalian cells," eLife, 9:e53968, May 15, 2020, 25 pages.
Yang et al., "One-step generation of mice carrying reporter and conditional alleles by CRISPR/Cas-mediated genome engineering," Cell, 154(6):1370-1379, Aug. 29, 2013.
Balciuniene et al., "Efficient disruption of Zebrafish genes using a Gal4-containing gene trap.," BMC Genomics, 14(1):619, Dec. 2013, 17 pages.
Carroll, "Genome Engineering With Zinc-Finger Nucleases," Genetics, 188(4):773-782, Aug. 2011.
Cho et al., "Targeted genome engineering in human cells with the Cas9 RNA-guided endonuclease," Nat. Biotechnology, 31(3):230-232, Mar. 2013.
Cong et al., "Multiplex Genome Engineering Using CRISPR/Cas Systems," Science, 339(6121):819-823, Feb. 15, 2013.
Conway et al., "Crystal structure of a Rad51 filament," Nat. Struct. Mol. Biology, 11(8):791-796, Aug. 2004.
Deltcheva et al., "CRISPR RNA maturation by trans-encoded small RNA and host factor RNase III," Nature, 471(7340):602-607, Mar. 31, 2011.
DiCarlo et al., "Genome engineering in *Saccharomyces cerevisiae* using CRISPR-Cas systems," Nucleic Acids Research, 41(7):4336-4343, Mar. 4, 2013.
Ferretti et al., "Complete genome sequence of an M1 strain of *Streptococcus pyogenes*," Proc. Nat. Acad. Sci. USA, 98(8):4658-4663, Apr. 10, 2001.
GenBank Accession No. AKP81606.1, "CRISPR-associated endonuclease Cas9/Csn1 [*Streptococcus pyogenes*]," dated Jul. 9, 2015, 2 pages.
GenBank Accession No. NC_015683.1, "*Corynebacterium ulcerans* BR-AD22, complete sequence," dated Jul. 30, 2015, 2 pages.
GenBank Accession No. NC 016782.1, "*Corynebacterium diphtheriae* 241, complete genome," dated Aug. 13, 2015, 2 pages.
GenBank Accession No. NC_016786.1, "*Corynebacterium diphtheriae* HC01, complete genome," dated Aug. 13, 2015, 2 pages.
GenBank Accession No. NC_017053.1, "*Streptococcus pyogenes* MGAS1882, complete genome," dated Aug. 13, 2015, 2 pages.
GenBank Accession No. NC_017317.1, "*Corynebacterium ulcerans* 809, complete genome," dated Aug. 13, 2015, 2 pages.
GenBank Accession No. NC_017861.1, "*Prevotella intermedia* 17 chromosome II, complete sequence," dated Aug. 13, 2015, 2 pages.
GenBank Accession No. NC 018010.1, "*Belliella baltica* DSM 15883, complete genome," dated Aug. 18, 2015, 2 pages.
GenBank Accession No. NC_018721.1, "*Psychroflexus torquis* ATCC 700755, complete genome," dated Aug. 14, 2015, 2 pages.
GenBank Accession No. NC_021284.1, "*Spiroplasma syrphidicola* EA-1, complete genome," dated Aug. 14, 2015, 2 pages.
GenBank Accession No. NC_021314.1, "*Streptococcus iniae* SF1, complete genome," dated Dec. 18, 2014, 1 page.
GenBank Accession No. NC_021846.1, "*Spiroplasma taiwanense* CT-1, complete genome," dated May 12, 2016, 2 pages.
GenBank Accession No. NP_472073.1, "hypothetical protein lin2744 [*Listeria innocua* Clip1262]," dated Dec. 17, 2014, 2 pages.
GenBank Accession No. WP_002864485.1, "type II CRISPR RNA-guided endonuclease Cas9 [*Campylobacter jejuni*]," dated Oct. 7, 2015, 1 page.
GenBank Accession No. YP_002342100.1, "hypothetical protein NMA0631 [*Neisseria meningitidis* Z2491]," dated Dec. 16, 2014, 2 pages.
GenBank Accession No. YP_002344900.1, "CRISPR-associated protein [ *Campylobacter jejuni* subsp. *jejuni* NCTC 11168 = ATCC 700819]," dated Aug. 3, 2016, 2 pages.
GenBank Accession No. YP_820832.1, "CRISPR-system-like protein [ *Streptococcus thermophilus* LMD-9]," dated Dec. 16, 2014, 2 pages.
Gu et al., "R gene expression induced by a type-III effector triggers disease resistance in rice," Nature, 435(7045):1122-1125, Jun. 23, 2005.
Hwang et al., "Efficient genome editing in zebrafish using a CRISPR-Cas system," Nat. Biotechnology, 31(3):227-229, Mar. 2013.
Jao et al., "Efficient multiplex biallelic zebrafish genome editing using a CRISPR nuclease system," Proc. Nat. Acad. Sci. USA, 110(34):13904-13909, Aug. 20, 2013.
Jiang et al., "RNA-guided editing of bacterial genomes using CRISPR-Cas systems," Nat. Biotechnology, 31(3):233-239, Mar. 2013.
Jinek et al., "A Programmable Dual-RNA—Guided DNA Endonuclease in Adaptive Bacterial Immunity," Science, 337(6096):816-821, Aug. 17, 2012.
Kay et al., "A Bacterial Effector Acts as a Plant Transcription Factor and Induces a Cell Size Regulator," Science, 318(5850):648-651, Oct. 26, 2007.
Kim et al., "Hybrid restriction enzymes: Zinc finger fusions to Fok I cleavage domain," Proc. Nat. Acad. Sci. USA, 93(3):1156-1160, Feb. 1996.
Mali et al., "RNA-Guided Human Genome Engineering via Cas9," Science, 339(6121):823-826, Feb. 15, 2013.
McGrail et al., "Somatic Mutagenesis with a Sleeping Beauty Transposon System Leads to Solid Tumor Formation in Zebrafish," PLoS One, 6(4):e18826, Apr. 2011, 14 pages.
McVey et al., "MMEJ repair of double-strand breaks (director's cut): deleted sequences and alternative endings," Trends in Genetics, Nov. 2008, 24(11):529-538.
Moreno-Mateos et al., "CRISPRscan: designing highly efficient sgRNAs for CRISPR-Cas9 targeting in vivo," Nat. Methods, 12(10):982-988, Oct. 2015.
Nakade et al., "Microhomology-mediated end-joining-dependent integration of donor DNA in cells and animals using TALENs and CRISPR/Cas9," Nat. Communications, 5(1):5560, Nov. 2014, 8 pages.
PCT International Preliminary Report on Patentability in International Appln. No. PCT/US2018/041888, dated Jan. 23, 2020, 9 pages.
PCT International Search Report and Written Opinion in International Appln. No. PCT/US2018/041888, dated Oct. 1, 2018, 17 pages.
Römer et al., "Plant Pathogen Recognition Mediated by Promoter Activation of the Pepper Bs3 Resistance Gene," Science, 318(5850):645-648, Oct. 26, 2007.
Sadelain et al., "Safe harbours for the integration of new DNA in the human genome," Nat. Rev, Cancer, 12(1):51-58, Jan. 2012.
Schornack et al., "Gene-for-gene-mediated recognition of nuclear-targeted AvrBs3-like bacterial effector proteins," J. Plant Physiology, 163(3):256-272, Feb. 10, 2006.
Singleton et al., "Structure of the single-strand annealing domain of human RAD52 protein," Proc. Nat. Acad. Sci. USA, 99(21):13492-13497, Oct. 15, 2002.
Stoddard, "Homing endonuclease structure and function," Q. Rev. Biophysics, 38(1):49-95, Feb. 2005.

(56) References Cited

OTHER PUBLICATIONS

Sugio et al., "Two type III effector genes of *Xanthomonas oryzae* pv. oryzae control the induction of the host genes OsTFIIAγ1 and OsTFX1 during bacterial blight of rice," Proc. Nat. Acad, Sci. USA, 104(25):10720-10725, Jun. 19, 2007.

Varshney et al., "High-throughput gene targeting and phenotyping in zebrafish using CRISPR/Cas9," Genome Research, 25(7):1030-1042, Jul. 2015.

Won et al., "PCR artifact in testing for homologous recombination in genomic editing in zebrafish," PLoS One, 12(3):e0172802, Mar. 31, 2017, 10 pages.

Yang et al., "Os8N3 is a host disease-susceptibility gene for bacterial blight of rice," Proc. Nat. Acad. Sci. USA, 103(27):10503-10508, Jul. 5, 2006.

Yang et al., "PAM-Dependent Target DNA Recognition and Cleavage by C2c1 CRISPR-Cas Endonuclease," Cell, 167(7):1814-1828, Dec. 15, 2016.

Zhang et al., "Efficient precise knockin with a double cut HDR donor after CRISPR/Cas9-mediated double-stranded DNA cleavage," Genome Biology, 18(1):35, Feb. 20, 2017, 18 pages.

Zu et al., "Supplementary Information for: TALEN-mediated precise genome modification by homologous recombination in zebrafish," Nat. Methods, Apr. 2013, 33 pages.

Zu et al., "TALEN-mediated precise genome modification by homologous recombination in zebrafish," Nat. Methods, 10(4):329-331, Apr. 2013.

Hisano et al., "Precise in-frame integration of exogenous DNA mediated by CRISPR/Cas9 system in zebrafish," Sci. Reports, 5:8841, Mar. 5, 2015, 28 pages.

Li et al., "Gene replacements and insertions in rice by intron targeting using CRISPR-Cas9," Nat. Plants, 2(10):16139, Sep. 12, 2016, 6 pages.

Nakamae et al., "Establishment of expanded and streamlined pipeline of PITCh knock-in—a web-based design tool for MMEJ-mediated gene knock-in, PITCh designer, and the variations of PITCh, PITCh-TG and PITCh-KIKO," Bioengineered, 8(3):302-308, Apr. 28, 2017.

Sakuma et al., "MMEJ-assisted gene knock-in using TALENs and CRISPR-Cas9 with the PITCh systems," Nat. Protocols, 11(1):118-133, Dec. 17, 2015.

Song et al., "Optimizing the DNA Donor Template for Homology-Directed Repair of Double-Strand Breaks," Mol. Ther. Nucleic Acids, 7:53-60, Feb. 28, 2017.

Yao et al., "Homology-mediated end joining-based targeted integration using CRISPR/Cas9," Cell Research, 27(6):801-814, May 19, 2017.

Hayashi et al., "Short-Homology-Mediated CRISPR/Cas9-Based Method for Genome Editing in Fission Yeast," G3, 9(4):1153-1163, Apr. 9, 2019.

Yang et al., "A CRISPR-Cas9 system constructed using double enzyme digestion," Chinese J. Path. Biology, 13(9):949-952, 957, Sep. 2018 (with English abstract).

Auer et al., "Highly efficient CRISPR/Cas9-mediated knock-in in zebrafish by homology-independent DNA repair," Genome Res., Jan. 2014, 24(1):142-153.

Clark et al., "In vivo protein trapping produces a functional expression codex of the vertebrate proteome," Nat. Methods, Jun. 2011, 8(6):506-515.

Grzesiuk et al., "Recombination of DNAs in Xenopus oocytes based on short homologous overlaps," Nucleic Acids Res., Feb. 1987, 15(3):971-985.

Halene et al., "Improved expression in hematopoietic and lymphoid cells in mice after transplantation of bone marrow transduced with a modified retroviral vector," Blood, Nov. 1999, 94(10):3349-3357.

Ihry et al., "p53 inhibits CRISPR-Cas9 engineering in human pluripotent stem cells," Nat. Med., Jul. 2018, 24(7):939-946.

Kanca et al., "An efficient CRISPR-based strategy to insert small and large fragments of DNA using short homology arms," Elife, Nov. 2019, 8:e51539.

Kotin et al., "Characterization of a preferred site on human chromosome 19q for integration of adeno-associated virus DNA by non-homologous recombination," EMBO J., Dec. 1992, 11(13):5071-5078.

Li et al., "Highly efficient genome editing via CRISPR-Cas9 in human pluripotent stem cells is achieved by transient BCL-XL overexpression," Nucleic Acids Res., Nov. 2018, 46(19):10195-10215.

Luo et al., "CRISPR/Cas9-based genome engineering of zebrafish using a seamless integration strategy," FASEB J., May 2018, 32(9):5132-5142.

Mann et al., "The Gene Sculpt Suite: a set of tools for genome editing," Nucleic Acids Res., Jul. 2019, 47(W1):W175-W182.

Maresca et al., "Obligate Ligation-Gated Recombination (ObLiGaRe): Custom-designed nuclease-mediated targeted integration through nonhomologous end joining," Genome Res., Mar. 2013, 23(3):539-546.

Mehta et al., "Homology Requirements and Competition between Gene Conversion and Break-Induced Replication during Double-Strand Break Repair," Mol. Cell, Feb. 2017, 65(3):515-526.e3.

Solin et al., "Rapid tumor induction in zebrafish by TALEN-mediated somatic inactivation of the retinoblastomal tumor suppressor rb1," Sci. Rep., Sep. 2015, 5:13745.

Suzuki et al., "In vivo genome editing via CRISPR/Cas9 mediated homology-independent targeted integration," Nature, Dec. 2016, 540(7631):144-149.

Wierson et al., "Expanding the CRISPR Toolbox with ErCas12a in Zebrafish and Human Cells," CRISPR J., Dec. 2019, 2(6):417-433.

* cited by examiner

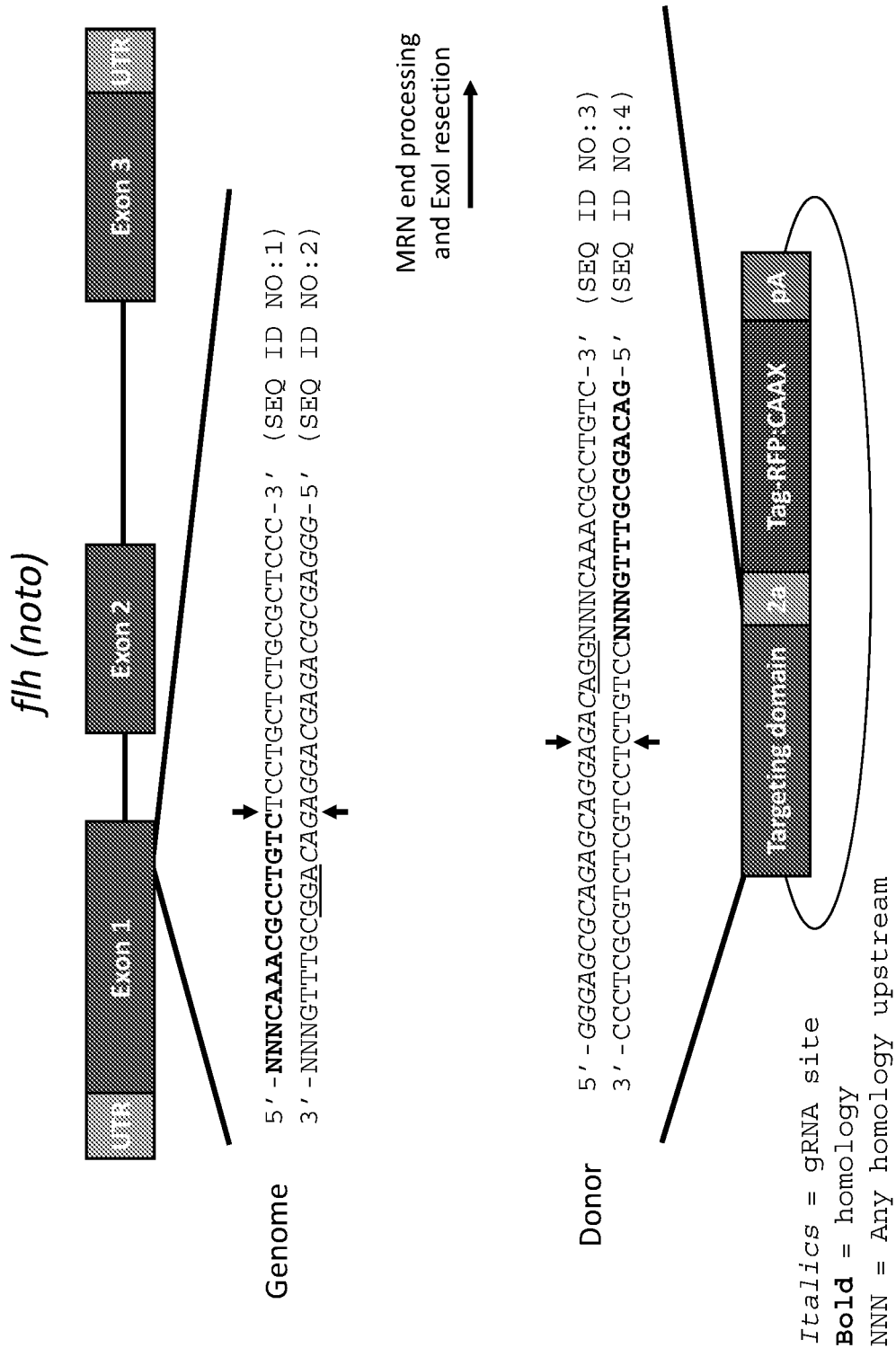

FIG. 5D

12 base pair homology arm (SEQ ID NO:)

```
                       noto <- 12 bp -> 2A
Precise junction  -  ACCAACCAAACGCCTGTCGGATCC       (21)
Emb. 1 allele 1   -  ACCAACCAAACGCCTGTCGGATCC       1/5 clones (21)
Emb. 1 allele 2   -  ACCAACCAAACGCCTGTCGGATCC       4/5 clones (22)
Emb. 2 allele 1   -  ACCAACCAAACGCCTGTCGGATCC       4/4 clones (21)
                                         Total 5/9 clones
```

24 base pair homology arm (SEQ ID NO:)

```
                       noto <- 24 bp -> 2A
Precise junction  -  TACCGGAGCATAACCAACCAAACGCCTGTCGGATCC       (23)
Emb. 1 allele 1   -  TACCGGAGCATAACCAACCAAACGCCTGTCGGATCC       10/10 clones (23)
Emb. 2 allele 1   -  TACCGGAGCATAACCAACCAAACGCCTGTCGGATCC       9/10 clones (23)
Emb. 2 allele 2   -  TACCGGAGCATAACCAACCAAACGCCCTGTCTAGGAGCATAACCAACCAAACGCCTGTCGGATCC  1/10 clones (24)
                                         Total 19/20 clones
```

48 base pair homology arm (SEQ ID NO:)

```
                       noto <----------- 48 bp ------------> 2A
Precise junction  -  GAGATGAGAGAGAACGAACAAACGGTACCGGAGCATAACCAACCAAACGCCTGTCGGATCC (25)
Emb. 1 allele 1   -  GAGATGAGAGAGAACGAACAAACGGTACCGGAGCATAACCAACCAAACGCCTGTCGGATCC 5/9 clones (25)
Emb. 1 allele 2   -  GAGATGAGAGAGAACGAACAAACGAACAAACGGTACCGGAGCATAACCAACCAAACGCCTGTCGGATCC 4/9 clones (26)
Emb. 2 allele 1   -  GAGATGAGAGAGAACGAACAAACGGTACCGGAGCATAACCAACCAAACGCCTGTCGGATCC 9/10 clones (25)
Emb. 2 allele 2   -  GAGATGAGAGAGAACGAACAAACGGTACCGGAGCATAACCAACCAAACGCCTGTCGGATCC 1/10 clones (27)
                                         Total 19/19 clones
```

5'— GGGAGGCGUUCGGGGCCACAGCGG —'3 (SEQ ID NO:28)

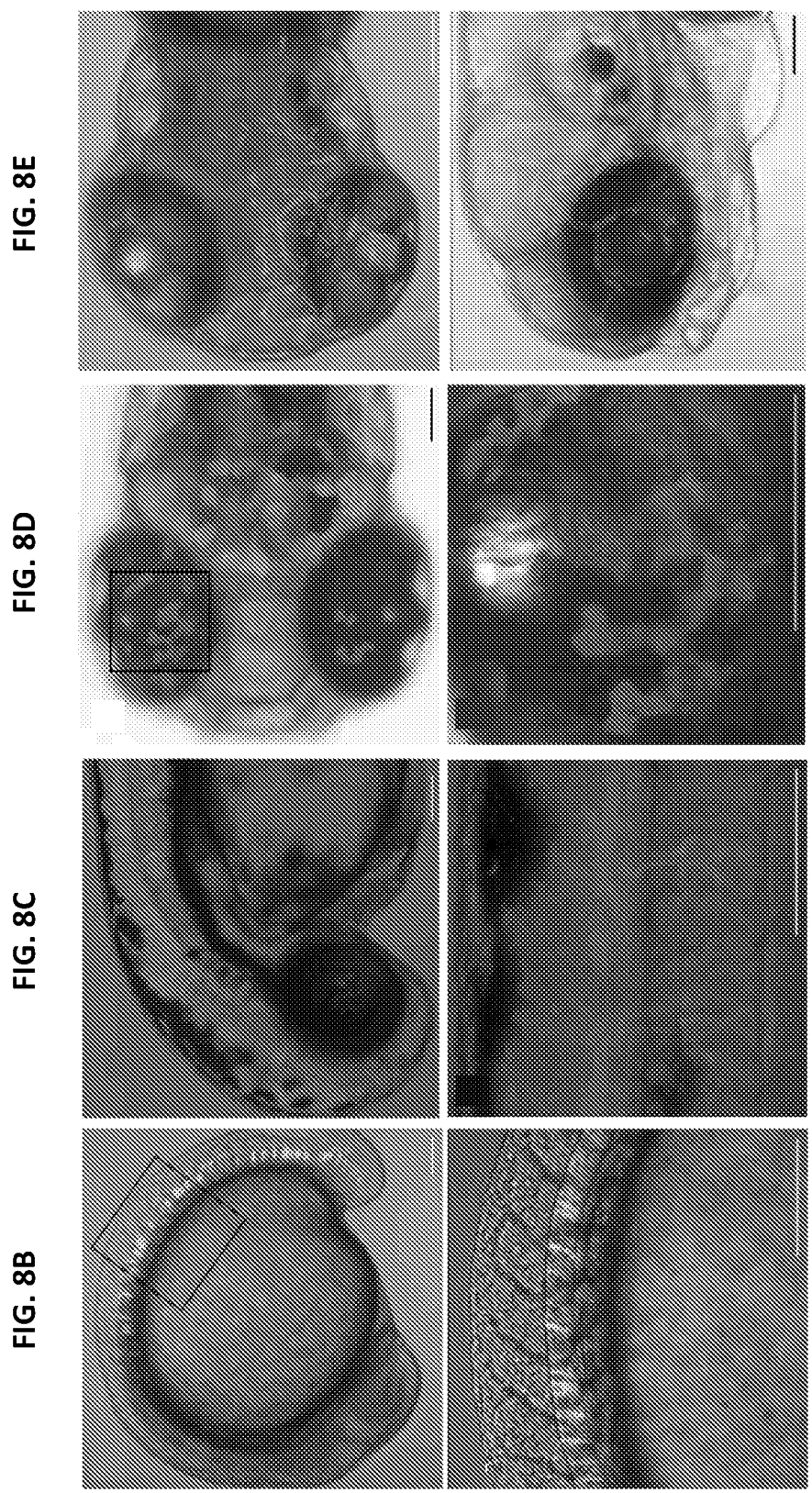

FIG. 9D noto DNA from Southern Blot
24 base pair homology arm - 5' F1 junctions from F0 #1 (SEQ ID NO:)

```
                     noto <----  24 bp domain  ---->Vector
Precise junction   - TACCGGAGCATAACCAACCAAACGCCTGTCGGATCC  (23)
F1 clone #1        - TACCGGAGCATAACCAACCAAACGCCTGTCGGATCC  (23)
F1 clone #2        - TACCGGAGCATAACCAACCAAACGCCTGTCGGATCC  (23)
F1 clone #3        - TACCGGAGCATAACCAACCAAACGCCTGTCGGATCC  (23)
F1 clone #4        - TACCGGAGCATAACCAACCAAACGCCTGTCGGATCC  (23)
```

24 base pair homology arm - 3' F1 junctions from F0 #1

```
                     --24bp homology domain--    Alternate homology
Knock-in alignment - TCCAGCTCTGCGCTCCCGCTTATT------ATCTGCTCTCCAACTCACT  (33)
F1 clone #2        - TCCAGCTCTGCGCTCCCGCTTATTCCGCTTATCTGCTCTCCAACTCACT  (34)
F1 clone #3        - TCCAGCTCTGCGCTCCCGCTTATTCCGCTTATCTGCTCTCCAACTCACT  (34)
F1 clone #4        - TCCAGCTCTGCGCTCCCGCTTATTCCGCTTATCTGCTCTCCAACTCACT  (34)
```

24 base pair homology arm - 5' F1 junctions from F0 #2

```
                     noto <----  24 bp domain  ---->Vector
Precise junction   - TACCGGAGCATAACCAACCAAACGCCTGTCGGATCC  (23)
F1 clone #5        - TACCGGAGCATAACCAACCAAACGCCTGTCGGATCC  (23)
F1 clone #6        - TACCGGAGCATAACCAACCAAACGCCTGTCGGATCC  (23)
F1 clone #7        - TACCGGAGCATAACCAACCAAACGCCTGTCGGATCC  (23)
F1 clone #8        - TACCGGAGCATAACCAACCAAACGCCTGTCGGATCC  (23)
```

24 base pair homology arm - 3' F1 junctions from F0 #2
No junctions obtained

FIG. 10A

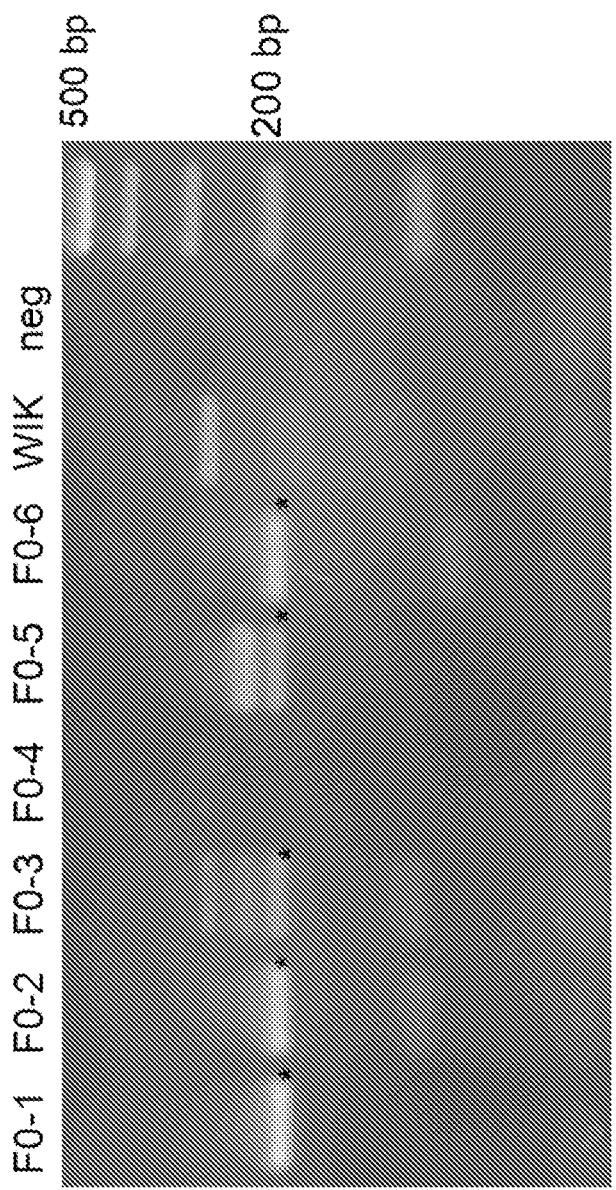

24 base pair homology arm

```
                       Tyr <---    24 bp homology    --->   2a
Perfect junction - ACAACGACGGATACTTCATGGTGCCCTTCATTGGATCC (SEQ ID NO:35)
Emb. 1 allele 1  - ACAACGACGGATACTTCATGGTGCCCTTCATTGGATCC  3/4 clones (SEQ ID NO:35)
Emb. 1 allele 2  - ACAACGACGGATACTTCATGGTGCCCTTCATTGGAcCC  1/4 clones (SEQ ID NO:36)
Emb. 2 allele 1  - ACAACGACGGATACTTCATGGTGCCCTTCATTGGATCC  3/3 clones (SEQ ID NO:35)
                                                Total 7/7 clones precise integration
```

FIG. 11C

F1 junction fragments

Tyrosinase genomic DNA from Southern Blot 24 base pair homology arm - 5' F1 junction (SEQ ID NO:)
                                 Tyr <--- 24 bp domain ---> Vector
Precise junction  — ACAACGACGGATACTTCATGGTGCCCTTCATtGGATCC (37)
F1 clone #1       — ACAACGACGGATACTTCATGGTGCCCTTCATtGGATCC (37)
F1 clone #2       — ACAACGACGGATACTTCATGGTGCCCTTCATtGGATCC (37)
F1 clone #3       — ACAACGACGGATACTTCATGGTGCCCTTCATtGGATCC (37)
F1 clone #4       — ACAACGACGGATACTTCATGGTGCCCTTCATtGGATCC (37)

24 base pair homology arm - 3' F1 junction (SEQ ID NO:)
                                 Vector<--- 24 bp domain ---> Tyr
Precise junction  — CCATGGTCCCTCTCTACAGGAACGGAGACTATTTTC (38)
F1 clone #1       — CCATGGTCCCTCTCTACAGGAACGGAGACTATTTTC (38)
F1 clone #2       — CCATGGTCCCTCTCTACAGGAACGGAGACTATTTTC (38)
F1 clone #3       — CCATGGTCCCTCTCTACAGGAACGGAGACTATTTTC (38)
F1 clone #4       — CCATGGTCCCTCTCTACAGGAACGGAGACTATTTTC (38)

FIG. 12B esama genomic DNA from Southern Blot
24 base pair homology arm - 5' junction (SEQ ID NO:)
esama <---- 24 bp domain ----> Vector

| | |
|---|---|
| Precise junction | CTTATGAAAAATGTGGATGTGATCCAAGGGAttGGATCC (39) |
| F0#4, F1#1 | CTTATGAAAAATGTGGTTGTGATCCAAGGGAttGGATCC (40) |
| F0#4, F1#2 | CTTATGAAAAATGTGGATGTGATCCAAGGGAttGGATCC (39) |
| F0#5, F1#1 | CTTATGAAAAATGTGGATGTGATCCAAGGGAttGGATCC (39) |
| F0#5, F1#2 | CATAAGAAAATGTGGATGTGATCCAAGGGAttGGATCC (41) |
| F0#6, F1#1 | CTTATGAAAAATGTGGATGTGATCCAAGGGAttGGATCC (39) |
| F0#6, F1#2 | CTTATGAAAAATGTGGATGTGATCCAAGGGAttGGATCC (39) |
| F0#7, F1#1 | CTTATGAAAAATGTGGATGTGATCCAAGGGAttGGATCC (39) |
| F0#7, F1#2 | CTTATGAAAAATGTGGATGTGATCCAAGGGAttGGATCC (39) |
| F0#9, F1#1 | CTTATGAAAAATGTGGATGTGATCCAAGGGAttGGATCC (39) |
| F0#11, F1#1 | CTTATGAAAAATGTGGATGTGATCCAAGGGAttGGATCC (39) |

24 base pair homology arm - 3' junction (SEQ ID NO:)
Vector<---- 24 bp domain ----> esama

| | |
|---|---|
| Precise junction | CCATGGAGAGATGGTGGTGCTGCAGGCGTCATATATTCGA (42) |
| F0#4, F1#1 | CCATGGAGAGATGGTGGTGCTGCAGGCTTCATATTCGA (43) |
| F0#4, F1#2 | CCATGGAGAGATGGTGGTGCTGCAGGCTTCATATTCGA (43) |
| F0#5, F1#1 | CCATGGAGAGATGGTGGTGCTGCAGGCTTCATATTCGA (43) |
| F0#5, F1#2 | CCATGGAGAGATGGTGGTGCTGCAGGCTTCATATTCGA (43) |
| F0#6, F1#1 | CCATGGAGAGATGGTGGTGCTGCAGGCTTCATATTCGA (43) |
| F0#6, F1#2 | CCATGGAGAGATGGTGGTGCTGCAGGCTTCATATTCGA (43) |
| F0#7, F1#1 | CCATGGAGAGATGGTGGTGCTGCAGGCTTCATGAAGCTGCTGCAGGCTTCATATTCGA (44) |
| F0#7, F1#2 | CCATGGAGAGATGGTGGTGCTGCAGGCTTCATATTCGA (43) |
| F0#9, F1#1 | CCATGGAGAGATGGTGGTGCTGCAGGCTTCATATTCGA (43) |
| F0#11, F1#1 | CCATGGAGAGATGGTGGTGCTGCAGGCTTCATATTCGA (43) |

MATERIALS AND METHODS FOR EFFICIENT TARGETED KNOCK IN OR GENE REPLACEMENT

CROSS-REFERENCE TO RELATED APPLICATIONS

This application is a National Stage application under 35 U.S.C. § 371 of International Application No. PCT/US2018/041888, having an International Filing Date of Jul. 12, 2018, which claims benefit of priority from U.S. Provisional Application No. 62/531,673, filed Jul. 12, 2017, which is incorporated herein by reference in its entirety.

STATEMENT AS TO FEDERALLY SPONSORED RESEARCH

This invention was made with government support under GM063904 and OD020166 awarded by the National Institutes of Health. The government has certain rights in the invention.

SEQUENCE LISTING

This application contains a Sequence Listing that has been submitted electronically as an ASCII text file named 07039_1713WO1_ST25.txt. The ASCII text file, created on Jul. 12, 2018, is 48,973 bytes in size. The material in the ASCII text file is hereby incorporated by reference in its entirety.

TECHNICAL FIELD

This document relates to materials and methods that can increase the efficiency of targeted knock ins and gene replacements.

BACKGROUND

Targeted integration of exogenous sequences into the genome is significantly more efficient following a double-strand break. Using custom nucleases, such as clustered regularly interspaced short palindromic repeat (CRISPR)/CRISPR-associated-9 (Cas9) systems or transcription activator-like effector (TALE) nucleases, researchers have been able to integrate new DNA into cells or whole organisms using single stranded DNA (ssDNA) oligonucleotides or larger double-stranded donors. The most efficient methods for integration in various cell types or whole animal models, however, have not been identified as such. Traditionally, homologous recombination uses long homology arms with lengths ranging from 500 base pairs to several kilobases of DNA on both sides of an integration donor.

SUMMARY

This document is based, at least in part, on the discovery that integration by short homology arms may be more efficient than integration by longer arms. Microhomology-based integration techniques are described elsewhere (see, e.g., Nakade et al., *Nature Commun* 5:5560, 2014), but it has now been determined that slightly larger homology arms, which likely use single strand annealing (SSA) repair pathways, are significantly more efficient for targeted integration in zebrafish. For example, 24 and 48 bp of homology were more efficient for achieving targeted integration than either 12 or 192 bp of homology. As described herein, studies have been conducted using CRISPR/Cas9 systems, and TAL effector nuclease-based methods are being used in zebrafish and other cultured cells to assess integration as well as whole gene exchange (i.e., deletion of a gene and replacement with another expression cassette). Thus, this document provides a targeted integration strategy, referred to as "GeneWeld," and a vector series for gene tagging ("pGTag"), which can promote highly efficient and precise targeted integration in cells of zebrafish and other vertebrates. This approach establishes an effective genome engineering solution that is suitable for gene therapy and functional genomic applications.

In a first aspect, this document features a nucleic acid construct containing, in order from 5' to 3', a first guide RNA (gRNA) target sequence, a 5' homology sequence that is homologous to a sequence 5' of a selected target sequence, a donor sequence to be inserted into the selected target sequence, and a 3' homology sequence that is homologous to a sequence 3' of the selected target sequence. The nucleic acid construct can further include a second gRNA target sequence, where the second gRNA target sequence is 3' of the 3' homology sequence. The first and second gRNA target sequences can be targets for the same gRNA. The first gRNA target sequence, or the first and second gRNA target sequences, can include the nucleotide sequence set forth in SEQ ID NO: 45. The 5' homology sequence can have a length between 12 bp and 192 bp, where the length of the 5' homology sequence is divisible by 3 or 4. The 3' homology sequence can have a length between 12 bp and 192 bp, where the length of the 3' homology sequence is divisible by 3 or 4. The 5' homology sequence can have a length of 24 bp. The 3' homology sequence can have a length of 24 bp. The 5' homology sequence can have a length of 48 bp. The 3' homology sequence can have a length of 48 bp. The nucleic acid construct can further include, between the 5' homology sequence and the donor sequence, a sequence encoding a peptide that causes translational skipping. The peptide that causes translational skipping can be 2A. The donor sequence to be inserted can encode a reporter (e.g., eGFP, TagRFP, or Gal4VP16). The sequence encoding the reporter can further encode a nuclear localization signal or a membrane localization CAAX sequence. The nucleic acid construct can further include, between the donor sequence and the 3' homology sequence, a polyadenylation sequence (pA). The pA can be zebrafish β-actin pA or SV40 pA. The donor sequence can have a length between about 1 bp and about 12,000 bp (e.g., between about 100 bp and about 1000 bp).

In another aspect, this document features a method for generating a targeted knockin of nucleic acid within the genome of a cell. The method can include introducing into the cell (a) a nucleic acid construct containing, in order from 5' to 3', a first gRNA target sequence, a 5' homology sequence that is homologous to a sequence 5' of a selected target sequence within the genome of the cell, a donor sequence to be inserted into the selected target sequence, and a 3' homology sequence that is homologous to a sequence 3' of the selected target sequence; (b) a Cas9 endonuclease; (c) a gRNA targeted to the first gRNA target sequence; and (d) a second endonuclease targeted to the selected target sequence within the genome of the cell; where the Cas9 endonuclease is directed to the nucleic acid construct by the gRNA targeted to the first gRNA target sequence, and cleaves the nucleic acid construct at the first gRNA target sequence, where the second endonuclease cleaves the genomic DNA at the selected target sequence, and where the donor sequence is inserted into the genomic DNA at the selected target sequence. The nucleic acid construct can further include a second gRNA target sequence, where the second gRNA target sequence is 3' of the 3' homology sequence. The first and second gRNA target sequences can be targets for the same gRNA. The first gRNA target sequence, or the first and second gRNA target sequences, can include the nucleotide sequence set forth in SEQ ID NO:45. The 5' homology sequence can have a length between 12 bp and 192 bp, where the length of the 5' homology sequence is divisible by 3 or 4. The 3' homology sequence can have a length between 12 bp and 192 bp, where the length of the 3' homology sequence is divisible by 3 or 4. The 5' homology sequence can have a length of 24 bp. The 3' homology sequence can have a length of 24 bp. The 5' homology sequence can have a length of 48 bp. The 3' homology sequence can have a length of 48 bp. The nucleic acid construct can further include, between the 5' homology sequence and the donor sequence, a sequence encoding a peptide that causes translational skipping. The peptide that causes translational skipping can be 2A. The donor sequence to be inserted can encode a reporter (e.g., eGFP, TagRFP, or Gal4VP16). The sequence encoding the reporter can further encode a nuclear localization signal or a membrane localization CAAX sequence. The nucleic acid construct can further include, between the donor sequence and the 3' homology sequence, a pA sequence. The pA can be zebrafish β-actin pA or SV40 pA. The donor sequence can have a length between about 1 bp and about 12,000 bp (e.g., between about 100 bp and about 1000 bp). The Cas9 endonuclease can be from *Streptococcus pyogenes*. The second endonuclease can be a Cas9 endonuclease, and the method can further include introducing into the cell (e) a synthetic guide RNA (sgRNA) targeted to the selected target sequence in the genome of the cell. The second endonuclease can be a transcription activator-like effector (TALE) nuclease having a pair of monomers targeted to genomic sequences within the cell near the selected target sequence, where the TALE nuclease monomers bind to their genomic target sequences and dimerize to cleave the genomic DNA at the selected target sequence. The cell can be a eukaryotic cell. The cell can be a vertebrate cell (e.g., a mammalian cell or a fish cell). The cell can be in vitro or in vivo. The introducing can include electroporation, transfection, or microinjection. Cleavage of the first gRNA target sequence by the Cas9 endonuclease and cleavage of the selected genomic target sequence by the second endonuclease can occur simultaneously.

In another aspect, this document features a method for modifying the genetic material of a cell, where the method includes introducing into the cell (a) a nucleic acid construct containing, in order from 5' to 3', a first gRNA target sequence, a 5' homology sequence that is homologous to a sequence 5' of a selected target sequence within the genome of the cell, a donor sequence to be inserted into the selected target sequence, and a 3' homology sequence that is homologous to a sequence 3' of the selected target sequence; (b) a Cas9 endonuclease; (c) a gRNA targeted to the first gRNA target sequence; (d) a second endonuclease targeted to a first target site, wherein the first target site is 5' of the selected target sequence within the genome of the cell but 3' of the genomic sequence homologous to the 5' homology sequence; and (e) a third endonuclease targeted to a second target site, wherein the second target site is 3' of the selected target sequence within the genome of the cell but 5' of the genomic sequence homologous to the 3' homology sequence, where the Cas9 endonuclease is directed to the nucleic acid construct by the gRNA targeted to the first gRNA target sequence, and cleaves the nucleic acid construct at the first gRNA target sequence, where the second endonuclease cleaves the genomic DNA at the first target site and the third endonuclease cleaves the genomic DNA at the second target site, generating a deletion of the selected target sequence within the genome of the cell, and where the donor sequence is inserted into the genomic DNA at the former location of the deleted target sequence. The nucleic acid construct can further include a second gRNA target sequence, where the second gRNA target sequence is 3' of the 3' homology sequence. The first and second gRNA target sequences can be targets for the same gRNA. The gRNA target sequence, or the first and second gRNA target sequences, can include the nucleotide sequence set forth in SEQ ID NO:45. The 5' homology sequence can have a length between 12 bp and 192 bp, where the length of the 5' homology sequence is divisible by 3 or 4. The 3' homology sequence can have a length between 12 bp and 192 bp, where the length of the 3' homology sequence is divisible by 3 or 4. The 5' homology sequence can have a length of 24 bp. The 3' homology sequence can have a length of 24 bp. The 5' homology sequence can have a length of 48 bp. The 3' homology sequence can have a length of 48 bp. The nucleic acid construct can further include, between the 5' homology sequence and the donor sequence, a sequence encoding a peptide that causes translational skipping. The peptide that causes translational skipping can be 2A. The donor sequence to be inserted can encode a reporter (e.g., eGFP, TagRFP, or Gal4VP16). The sequence encoding the reporter can further encode a nuclear localization signal or a membrane localization CAAX sequence. The nucleic acid construct can further include, between the donor sequence and the 3' homology sequence, a pA sequence. The pA can be zebrafish β-actin pA or SV40 pA. The donor sequence can have a length between about 1 bp and about 12,000 bp (e.g., between about 100 bp and about 1000 bp). The Cas9 endonuclease can be from *Streptococcus pyogenes*. The second endonuclease can be a Cas9 endonuclease and the third endonuclease can be a Cas9 endonuclease, and the method can further include introducing into the cell (e) a sgRNA targeted to the first target site in the genome of the cell; and (f) a sgRNA targeted to the second target site in the genome of the cell. The second endonuclease can be a TALE nuclease targeted to the first target site and the third endonuclease can be a TALE nuclease targeted to the second target site, where the TALE nucleases cleave the genomic DNA at the first and second target sites. The cell can be a eukaryotic cell. The cell can be a vertebrate cell (e.g., a mammalian cell or a fish cell). The cell can be in vitro or in vivo. The introducing can include electroporation, transfection, or microinjection. Cleavage of the first gRNA target sequence by the Cas9 endonuclease and cleavage of the selected genomic target sequence by the second endonuclease can occur simultaneously.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic showing a general method for short homology-directed knock-in.

As shown in FIG. 4A, Type IIs restriction endonucleases BfuAI and BspQI create incompatible ends outside of the recognition sequence, allowing digestion and ligation of both homology arms into the vector in a single reaction. Homology arm fragments are formed by annealing complementary oligonucleotides to form dsDNA with sticky ends for directional cloning into the vector. XFP=Green or Red Fluorescent Protein. pA=SV40 or b-actin 3' untranslated region. FIG. 4B shows GeneWeld reagent components for simultaneous genome and donor designer nuclease targeting to reveal short regions of homology. Arrowheads represent in vivo designer nuclease double stranded DNA breaks.

FIGS. 5A-5D show that short homology to the noto gene from a single homology arm 5' to the gRNA target site targets integration in zebrafish embryos. FIG. 5A is a schematic for noto homology arm and donor vector design. gRNA is the noto non-coding template strand. Black bars represent 12, 24, and 48 bp homology arms. Protospacer adjacent motif (PAM) sequences are underlined. FIG. 5B is a graph plotting targeting efficiency of 12, 24, and 48 bp noto 5' bait donors. Data represent mean±s.e.m. of 3 independent targeting experiments. p values were calculated using two-tailed unpaired t-test. FIG. 5C is a live confocal image of a noto-2A-TagRFP-CAAX-SV40 targeted embryo, showing specific RFP expression in the notochord. The scale bar is 100 um. FIG. 5D shows Sanger sequencing of cloned 5' junction fragments from RFP positive F0 embryos, aligned to the expected sequence from a precise integration event. Differences from the expected sequence are boxed. Sequence identifiers are provided in parentheses.

FIG. 6A is a schematic for targeting 2A-TagRFP-CAAXSV40 into noto exon 1 with 5' homology to the Cas9/gRNA cut site containing 47, 48, or 49 bp of homology. FIG. 6B is a graph plotting the frequency of injected zebrafish embryos displaying notochord RFP expression after targeting noto exon 1 with donors containing 47, 48, or 49 bp of 5' homology. Data represent mean±s.e.m. of 3 (47 bp, 49 bp) or 7 (48 bp) independent targeting experiments. p values were calculated using two-tailed unpaired t-test.

FIG. 7A is the Universal gRNA (UgRNA) sequence (SEQ ID NO: 28). The Cas9 PAM is underlined. FIG. 7B is a schematic showing the sequence of UgRNA in the targeting domain of the knock-in cassette. The boxed sequence represents engineered homology. The Cas9 PAM is underlined. FIG. 7C is a graph plotting the frequency of injected embryos displaying RFP expression in the notochord following noto targeting with UgRNA liberating the homology in the donor.

FIGS. 8A-8E show that the HMEJ strategy promotes efficient integration of knock-in cassettes at different zebrafish loci. FIG. 8A is a graph plotting reporter gene targeting with HMEJ at noto, cx43.4, tyr, and esama, which resulted in a high proportion of injected F0 embryos displaying widespread signals. Data represent mean±s.e.m. of 3 independent targeting experiments. p values were calculated using two-tailed unpaired t-test. FIGS. 8B-8E are live confocal images of F0 injected embryos showing fluorescent reporter expression of noto-2A-eGFP-SV40 at the mid somite stage (FIG. 8B), cx43.4-2A-tagRFP-CAAX-SV40 at 31 hours post fertilization (FIG. 8C), tyr-2A-Gal4VP16-bactin at 5 days post fertilization (dpf) (FIG. 8D), and esama-2A-Gal4VP16-bactin at 2 dpf (FIG. 8E, top) and 3 dpf (FIG. 8E, bottom). Scale bars, 100 um.

FIGS. 9A-9D show the results of molecular analysis of Tg(noto-2A-RFP) F1 targeted integration alleles from two independent F0 founders. FIG. 9A is a diagram of a noto gene model with the locations of restriction enzymes used for genomic Southern blot analysis. Location of the 513 bp noto probe is indicated by dark lines. The predicted and recovered alleles also are shown. FIG. 9B is an image of a Southern blot of F1 Tg(noto-2A-RFP) individuals hybridized with an RFP probe. F1 from founder F0 #1 contain a ~2100 bp band corresponding to integration plus deletion of ~400 bp in noto. F1 progeny from founder F0 #2 show two bands: a ~3700 bp band corresponding to integration of the reporter plus 2000 bp of vector backbone, and a ~1500 bp band which may represent an off target integration. Loading controls (10, 1) correspond to 10 copies or 1 copy of RFP containing plasmid. WIK, wild type control DNA. FIG. 9C is an image of the Southern blot from FIG. 9B, stripped and re-hybridized with a noto-specific probe. A 1342 bp band representing the wild type allele was detected in all individuals. The integration allele in F1s from F0 #1 was not detected due to deletion of the region containing the probe. F1s from F0 #2 contain the ~3700 bp band corresponding to the noto-2A-RFP integration allele. FIG. 9D shows the sequences of PCR junction fragments amplified from F1 genomic DNA that was used for Southern blots, indicating precise integration at the 5' end all F1s. 3' junction fragments from F1s derived from F0 #1 showed an alternative homology domain in the noto gene was used, resulting in deletion. The 3' junction fragment in F1s from F0 #2 was not able to be amplified. Sequence identifiers are provided in parentheses.

FIGS. 10A and 10B show that integration of Gal4/VP16 amplifies the signal of targeted tyr. FIG. 10A includes an image of a gel containing PCR amplicons of 5' junction fragments, as well as sequencing results from junction fragments between the pGTAG vector and the tyr locus that were amplified from randomly selected RFP negative embryos after injection with reagents for targeting tyr with 2AtagRFP-CAAX-pA. F0 injected zebrafish contained the expected junction fragments (*), and junction fragments from F0-1 and -2 were isolated for sequencing. RFP expression was not observed. FIG. 10B is a graph plotting the efficiency of 5' homology to the Cas9/UgRNA cut site to target RFP or GAL4/VP16 into tyr and detect RFP expression. Data represent mean±s.e.m. of 3 independent targeting experiments. p values were calculated using two-tailed unpaired t-test.

FIGS. 11A-11C show the results of molecular analysis of Tg(tyr-2A-GAL4/VP16) F1 offspring from a single targeted F0 founder. FIG. 11A is a schematic of the expected integration pattern for tyr targeted with pGTag-2A-GAL4/VP16. The position of the 148 bp tyr probe in Exon 3 is indicated. FIG. 11B is a pair of images showing GAL4/VP16 (top) and tyr probed Southern blots of genomic DNA from wild type (WIK) and 4 individual GAL4/VP16 positive F1s. The expected 7400 bp band was detected with both probes, suggesting a single copy integration. FIG. 11C shows the sequences of PCR junction fragments amplified from F1 genomic DNA, indicating precise integration at both 5' and 3' ends. Sequence identifiers are provided in parentheses.

FIGS. 12A and 12B show molecular analysis of Tg(esama-2A-GAL4/VP16) F1 offspring from 6 independent F0 founders. FIG. 12A is a schematic of the expected integration pattern for esama targeted with pGTag-2AGAL4/VP16 into exon 2. FIG. 12B shows the sequence of PCR amplified and cloned 5' and 3' junction fragments from genomic DNA from F1 Tg(esama-2A-Gal4VP16); Tg(UAS:mRFP)$^{tp12}$ individuals. Differences from the expected sequence are boxed. Sequence identifiers are provided in parentheses. Strikethrough indicates an insertion.

FIG. 13A is a schematic for Gal4VP16 reporter integration to tag a deletion allele of rb1 exons 2-4 (top) and rb1 exons 2-25 (bottom). Arrowheads designate CRISPR/Cas9 double-strand DNA breaks. CRISPR gRNAs in two exons are expected to delete the intervening genomic DNA. The targeting vector contains a 5' homology arm from the upstream exon, and a second homology arm from the downstream targeted exon. FIG. 13B includes live confocal images of an F0 Tg(UAS:mRFP)$^{tp12}$ embryo with tagged rb1 exons 2-4 deletion by integration of 2A-Gal4VP16-bactin. FIG. 13C is a schematic for Gal4VP16 deletion tagging of msna exons 2-6. FIG. 13D includes live confocal image of an F0 Tg(UAS:mRFP)$^{tp12}$ embryo with tagged msna exons 2-6 deletion replaced by 2A-Gal4VP16-bactin. FIG. 13E is a graph plotting the efficiency of targeted deletion tagging using 48 bp homology arms for rb1 exons 2-4, rb1 exons 2-25, and msna exons 2-6. Data represent mean #s.e.m. of 4 (rb1) and 5 (msna) independent targeting experiments. p values were calculated using two-tailed unpaired t-test. Scale bars in the left panels of FIGS. 13B and 13D are 200 um; scale bars in the right panels of FIGS. 13B and 13D are 100 um.

FIG. 14A includes images of a Tg(noto-2A-TagRFP-CAAX-SV40) embryo at the mid somite stage. FIG. 14B includes images of a 5 dpf Tg(tyr-2A-Gal4Vp16-bactin); Tg(UAS:mRFP)$^{tp12}$ larva. FIG. 14C includes images of dorsal (top) and lateral (bottom) views of a 3 dpf Tg(esama-2AGal4Vp16-bactin); Tg(UAS:mRFP)$^{tp12}$ larva. The scale bar is 100 um.

DETAILED DESCRIPTION

Figure 1B:
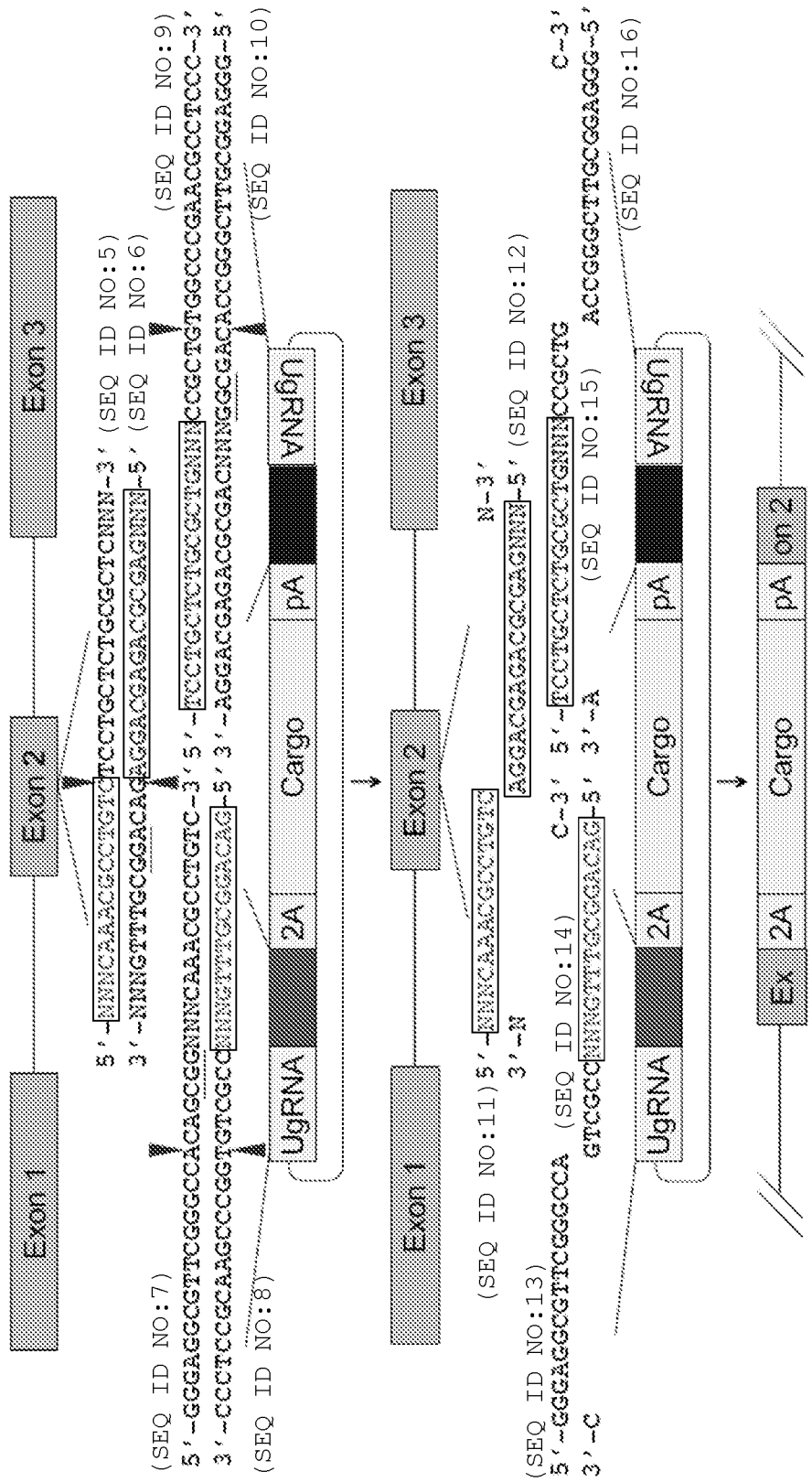
FIG. 1B is a diagram depicting a method for targeting integration of the pGTag vectors into the 5' region of a gene via dual UgRNA-mediated liberation of short homology donor cargo. Upon CRISPR/Cas9 targeting and cutting of both the genome (with a sgRNA) and plasmid donor (with UgRNA), the genomic and plasmid DNA can undergo end resection mediated by the MRN complex and ExoI, resulting in annealing of complementary homology arms. This promotes precise homology-directed integration of cargo DNA at the CRISPR/Cas9 double-strand break. Arrowheads mark CRISPR/Cas9 double-strand DNA breaks. Boxes indicate homology arms containing sequences upstream and downstream flanking the genomic CRISPR cut site.

This document provides materials and methods that can be used to efficiently achieve precise editing events in genomic DNA. In some embodiments, the materials and methods described herein can be particularly useful for obtaining targeted insertions, or targeted gene replacements (deletions combined with insertions) in any of a variety of cell types in culture or in vivo, including cells of vertebrates such as mammals (e.g., humans, non-human primates, pigs, rats, mice, rabbits, dogs, cats, sheep, and cows) and fish (e.g., zebrafish).

As described herein, donor nucleic acid constructs (containing a donor sequence to be integrated at the targeted sequence within the cell) can include two regions of homology to a targeted sequence within a cell, where the regions of homology are relatively short (e.g., 12 to 99 bp), and are positioned on either side of the donor sequence within the construct. The use of homology sequences of such lengths can be more efficient than longer or shorter sequences at achieving targeted integration of donor sequences. The methods provided herein include using a targeted endonuclease to cleave the DNA being targeted for insertion, as well as cleaving the donor construct adjacent to one or both homology sequences. As described herein cleaving the donor construct in addition to the target can even more effectively lead to generation of targeted insertions or gene replacements.

Thus, this document provides nucleic acids, polypeptides, and methods for their use in targeted insertion and gene replacement.

The terms "nucleic acid" and "polynucleotide" are used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An "isolated" nucleic acid is a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, e.g., *Short Protocols in Molecular Biology*, Chapter 8, Green Publishing Associates and John Wiley & Sons, edited by Ausubel et al., 1992.

Recombinant nucleic acid constructs (e.g., vectors) also are provided herein. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. In some cases, a vector can include an "expression control sequence"—a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, nuclear localization sequences (NLS), and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 1000 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically includes at least a core (basal) promoter. A promoter also may include at least one control element such as an upstream element. Such elements include upstream activation regions (UARs) and, optionally, other DNA sequences that affect transcription of a polynucleotide such as a synthetic upstream element.

In some cases, the nucleic acid and amino acid molecules provided herein can have a particular percentage of identity to a reference sequence. For example, a Cas9 coding sequence used in the methods provided herein can have at least 90% (e.g., at least 95%, at least 98%, at least 99%, or 100%) identity to a reference Cas9 sequence (e.g., the Cas9 coding sequence set forth in SEQ ID NO:155).

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq -i c:\seq1.txt-j c:\seq2.txt -p blastn -o c:\output-.txt -q −1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:155), or by an articulated length (e.g., 100 consecutive nucleotides or amino acid residues from a sequence set forth in an identified sequence), followed by multiplying the resulting value by 100. For example, a nucleotide sequence that has 4054 matches when aligned with the Cas9 coding sequence set forth in SEQ ID NO:155 is 98.8 percent identical to the sequence set forth in SEQ ID NO:155 (i.e., 4054/4104× 100=98.8%). It is noted that the percent sequence identity value is rounded to the nearest tenth. For example, 75.11, 75.12, 75.13, and 75.14 is rounded down to 75.1, while 75.15, 75.16, 7.17, 75.18, and 7.19 is rounded up to 7.2. It also is noted that the length value will always be an integer.

In some cases, the methods provided herein can include introducing a polypeptide (e.g., an endonuclease polypeptide) into a cell. The term "polypeptide" as used herein refers to a compound of two or more subunit amino acids regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

An "isolated" or "purified" polypeptide is a polypeptide that is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

In some embodiments, this document provides nucleic acid constructs (e.g., vectors) that include a donor sequence to be integrated into a genomic target sequence, where the donor is flanked by 5' and 3' homology sequences that are homologous to sequences within the targeted cellular DNA.

The donor sequence to be integrated can have a length from about 1 to about 12,000 bp (e.g., 1 to 10 bp, 10 to 50 bp, 50 to 100 bp, 100 to 250 bp, 100 to 1000 bp, 250 to 500 bp, 250 to 1000 bp, 500 to 750 bp, 500 to 1000 bp, 750 to 1000 bp, 1000 to 2000 bp, 2000 to 3000 bp, 3000 to 5000 bp, 5000 to 7500 bp, 7500 to 10,000 bp, or 10,000 to 12,000 bp). Examples of donor sequences include, without limitation, sequences encoding reporters such as green fluorescent protein (GFP or eGFP), yellow fluorescent protein (YFP), red fluorescent protein (RFP), luciferase, CRE, and CRE-ER™, or sequences encoding another polypeptide of interest, such as a therapeutic polypeptide or a polypeptide that may be lacking in the recipient cell due to a genetic mutation, for example. In some cases, the coding sequence in the donor can be operably linked to a promoter that controls expression of the coding sequence. Suitable promoters include constitutive promoters that allow for continual transcription of the coding sequence [e.g., the CaMV 35S promoter, the plant ubiquitin promoter (Ubi), the rice actin 1 promoter (Act-1), the maize alcohol dehydrogenase 1 promoter (Adh-1), and the CMV Ubi and β-actin ef1a promoters], and inducible promoters that can be turned on or off based on the presence or absence of various chemical or physical factors. Examples of useful inducible promoters include the heat shock 70 (HSP70) promoter, CRE inducible or floxed promoters, and Tet on Tet off or ecdysone inducible promoters.

The 5' and 3' homology sequences can independently have lengths from about 12 to about 192 nucleotides, typically where each length is divisible by 3 or by 4. For example, the 5' homology sequence can have a length of 12, 15, 16, 18, 20, 21, 24, 27, 28, 30, 32, 33, 36, 39, 40, 42, 44, 45, 48, 51, 52, 54, 56, 57, 60, 63, 64, 66, 68, 69, 72, 75, 76, 78, 80, 81, 84, 87, 88, 90, 92, 93, 96, 99, 100, 102, 104, 105, 108, 111, 112, 114, 116, 117, 120, 123, 124, 126, 128, 129, 132, 135, 136, 138, 140, 141, 144, 147, 148, 150, 152, 153, 156, 159, 160, 162, 164, 165, 168, 171, 172, 174, 176, 177, 180, 183, 184, 186, 188, 189, or 192 bp, and the 3' homology sequence (independently from the 5' homology sequence) can have a length of 12, 15, 16, 18, 20, 21, 24, 27, 28, 30, 32, 33, 36, 39, 40, 42, 44, 45, 48, 51, 52, 54, 56, 57, 60, 63, 64, 66, 68, 69, 72, 75, 76, 78, 80, 81, 84, 87, 88, 90, 92, 93, 96, 99, 100, 102, 104, 105, 108, 111, 112, 114, 116, 117, 120, 123, 124, 126, 128, 129, 132, 135, 136, 138, 140, 141, 144, 147, 148, 150, 152, 153, 156, 159, 160, 162, 164, 165, 168, 171, 172, 174, 176, 177, 180, 183, 184, 186, 188, 189, or 192 bp. In some cases, the 5' homology sequence can have a length of 12, 24, 36, 48, 60, 72, 84, or 96 bp, and the 3' homology sequence can independently have a length of 12, 24, 36, 48, 60, 72, 84, or 96 bp.

The 5' and 3' homology sequences can be selected using, for example, the methods described herein. In some cases, the homology sequences can be selected to cause a targeted insertion within a genomic "safe harbor" sequence—a chromosomal location at which transgenes (e.g., therapeutic transgenes) can integrate and function in a predictable manner, without disturbing endogenous gene activity or promoting adverse effects within the cell. See, e.g., Saledain et al., *Nature Rev Cancer* 12:51-58, 2012.

The donor constructs provided herein also can include one or more endonuclease cleavage sites that permit the construct to be cleaved on one or both sides of the donor sequence to be integrated. As described herein, cleaving both the donor construct and the targeted genomic sequence can increase the frequency and efficiency of targeted insertion. In some cases, therefore, a donor construct can have a cleavage site for a first targeted endonuclease on the 5' side of the 5' homology sequence. For example, a donor construct can include a target sequence for a first gRNA, where the target sequence is located 5' of the 5' homology sequence. In some cases, a donor construct also can have a cleavage site for a second targeted endonuclease on the 3' side of the 3' homology sequence. For example, a donor construct can include a target sequence for a second gRNA, where the target sequence is 3' to the 3' homology sequence. When two cleavage target sites are included, they can be the same, such that they are targeted by the same endonuclease, or they can be different, such that they are targeted by different endonucleases. In some cases, a donor construct can include the same gRNA target site in both locations (i.e., 5' of the 5' homology sequence and 3' of the 3' homology sequence), such that both sites can be cleaved by Cas9 when the appropriate gRNA is present. The cleavage site can be selected or engineered such that it is unique, and is not found elsewhere in the donor construct or in the genome of the cell to be targeted for insertion. As described herein, for example, a "universal" UgRNA target can be identified and included in the donor construct on one or both sides of the donor sequence to be inserted into the genome of a cell (e.g., outside the 5' and 3' homology sequences). A non-limiting example of a UgRNA target sequence that is not present in the zebrafish, pig, or human genome is set forth in SEQ ID NO:58 (without a PAM sequence) and SEQ ID NO:45 (with a PAM sequence at the 3' end).

The donor nucleic acid construct can include other sequences in addition to the donor, the 5' and 3' homology sequences, and the cleavage target sequence(s). For example, in some cases, a nucleic acid construct can include a coding sequence for a polypeptide that causes translational skipping. The presence of a translational skipping sequence between the 5' homology sequence and the donor coding sequence can allow the encoded polypeptide to dissociate from the polypeptide encoded by the genomic locus into which the donor sequence is inserted. Suitable translational skipping polypeptides include, for example, 2A.

In some cases, the coding sequence within a donor nucleic acid construct can include a sequence encoding a localization domain. For example, a donor nucleic acid can include a sequence encoding a nuclear localization signal (NLS) or a membrane localization CAAX sequence.

In some cases, the coding sequence within a donor nucleic acid construct can include a polyadenylation sequence (pA). The pA can be located within the 3' portion of the coding sequence, typically between the coding sequence and the 3' homology sequence. Any suitable pA can be included, such as a zebrafish pA (e.g., the zebrafish β-actin pA) or a viral pA (e.g., the SV40 pA).

The components of a donor nucleic acid construct can be contained within any suitable vector backbone, including those of the vectors listed herein.

This document also provides methods for using the donor nucleic acid constructs described herein to modify genomic DNA by, for example, generating a targeted insertion or a gene replacement within a cell. The methods can include introducing into a cell (e.g., a vertebrate cell, such as a mammalian or fish cell, either in vivo or in vitro in culture) a donor nucleic acid construct as described herein, together with a rare-cutting endonuclease targeted to a selected sequence in the genome, and a rare-cutting endonuclease targeted to the donor nucleic acid sequence, such that the rare-cutting endonuclease targeted to the donor nucleic acid construct cleaves the nucleic acid construct at a target sequence therein, the rare-cutting endonuclease targeted to the selected genomic sequence cleaves the genomic DNA at the target sequence therein, and the donor sequence is inserted into the genomic DNA at the selected target sequence.

A "rare-cutting endonuclease" is a natural or engineered protein that has endonuclease activity and is directed to a nucleic acid sequence with a recognition sequence (target sequence) that typically is about 12-40 bp in length (e.g., 14-40, 15-30 or 14-20 bp in length). Typical rare-cutting endonucleases cause cleavage inside their recognition site, leaving 4 nt staggered cut with 3'OH or 5'OH overhangs.

Any suitable rare-cutting endonuclease, or combination of rare-cutting endonucleases, can be used in the methods described herein. In some cases, the endonuclease that cleaves both the genomic DNA and the donor nucleic acid construct can be a Cas9 endonuclease (e.g., a Cas9 nuclease from *Streptococcus pyogenes*, having the amino acid sequence set forth in SEQ ID NO:156 and encoded by the nucleotide sequence set forth in SEQ ID NO:155). Cas9 endonucleases from other organisms (e.g., *Corynebacterium ulcerans* (NCBI Refs: NC_015683.1 and NC_017317.1), *C. diphtheria* (NCBI Refs: NC_016782.1 and NC_016786.1), *Spiroplasma syrphidicola* (NCBI Ref: NC_021284.1), *Prevotella intermedia* (NCBI Ref: NC_017861.1), *Spiroplasma taiwanense* (NCBI Ref: NC_021846.1), *Streptococcus iniae* (NCBI Ref: NC_021314.1), *Belliella baltica* (NCBI Ref: NC_018010.1), *Psychroflexus torquis* (NCBI Ref: NC_018721.1), *Streptococcus thermophilus* (NCBI Ref: YP_820832.1), *Listeria innocua* (NCBI Ref: NP_472073.1), *Campylobacter jejuni* (NCBI Ref: YP_002344900.1), *Neisseria meningitidis* (NCBI Ref: YP_002342100.1), and *Francisella novicida*, also can be used.

When a Cas9 endonuclease is used in a method as provided herein, the method also can include introducing into the cells one or more gRNA molecules to target the Cas9 enzyme to the desired sequence(s) in the genomic DNA and/or the donor nucleic acid construct. In some cases, one or more synthetic gRNA (sgRNA) molecules can be used. sgRNA is a chimera, and consists of (1) a 20 to 25 nt base-pairing region for specific DNA binding, (2) a 42 nt dCas9 handle hairpin for Cas9 protein binding, and (3) a 40 nt transcription terminator hairpin derived from *S. pyogenes*.

The CRISPR/Cas system includes components of a prokaryotic adaptive immune system that is functionally analogous to eukaryotic RNA interference, using RNA base pairing to direct DNA or RNA cleavage. The Cas9 protein functions as an endonuclease, and CRISPR RNA (crRNA) and tracer RNA (tracrRNA) sequences complex with the Cas9 enzyme and direct it to a target DNA sequence (Makarova et al., *Nat Rev Microbiol* 9 (6): 467-477, 2011). The modification of a single targeting RNA can be sufficient to alter the nucleotide target of a Cas protein. In some cases, crRNA and tracrRNA can be engineered as a single cr/tracrRNA hybrid (also referred to as a "guide RNA" or "gRNA") to direct Cas9 cleavage activity (Jinek et al., *Science,* 337 (6096): 816-821, 2012). The CRISPR/Cas system can be used in a variety of prokaryotic and eukaryotic organisms (see, e.g., Jiang et al., *Nat Biotechnol,* 31 (3): 233-239, 2013; Dicarlo et al., *Nucleic Acids Res,* doi: 10.1093/nar/gkt135, 2013; Cong et al., *Science,* 339 (6121): 819-823, 2013; Mali et al., *Science,* 339 (6121): 823-826, 2013; Cho et al., *Nat Biotechnol,* 31 (3): 230-232, 2013; and Hwang et al., *Nat Biotechnol,* 31 (3): 227-229, 2013).

CRISPR clusters are transcribed and processed into crRNA; the correct processing into crRNA requires a trans-encoded small tracrRNA. The combination of Cas9, crRNA, and tracrRNA can then cleave linear or circular dsDNA targets that are complementary to a spacer within the CRISPR cluster. Cas9 recognizes a short protospacer adjacent motif (PAM) in the CRISPR repeat sequences, which aids in distinguishing self from non-self. Cas9 nuclease sequences and structures are well known to those of skill in the art (see, e.g., Ferretti et al., *Proc Natl Acad Sci USA* 98:4658-4663, 2001; Deltcheva et al., *Nature* 471:602-607, 2011; and Jinek *Science* 337:816-821, 2012). Cas9 orthologs also have been described in species such as *S. pyogenes* and *S. thermophilus*.

The homology region within the crRNA sequence (the sequence that targets the crRNA to the desired DNA sequence) can be between about 10 and about 40 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40) nucleotides in length. The tracrRNA hybridizing region within each crRNA sequence can be between about 8 and about 20 (e.g., 8, 9, 10, 11, 12, 13, 14, 15, 16, 17, 18, 19, or 20) nucleotides in length. The overall length of a crRNA sequence can be, for example, between about 20 and about 80 (e.g., 20, 25, 30, 35, 40, 45, 50, 55, 60, 65, 70, 75, or 80) nucleotides, while the overall length of a tracrRNA can be, for example, between about 10 and about 30 (e.g., 10, 12, 14, 16, 18, 20, 22, 24, 26, 28, or 30) nucleotides. The overall length of a gRNA sequence, which includes a homology region and a stem loop region that contains a crRNA/tracrRNA hybridizing region and a linker-loop sequence, can be between about 30 and about 110 (e.g., 30, 35, 40, 45, 50, 55, 60, 65, 70, 75, 80, 85, 90, 95, 100, 105, 110, 115, 120, 125, or 130) nucleotides.

A representative Cas9 nucleic acid sequence is set forth in SEQ ID NO:155, and a representative Cas9 amino acid sequence is set forth in SEQ ID NO:156.

```
Streptococcus pyogenes Cas9 (NCBI Ref. NC_017053.1):
                                                    (SEQ ID NO: 155)
ATGGATAAGAAATACTCAATAGGCTTAGATATCGGCACAAATAGCGTCGGAT

GGGCGGTGATCACTGATGATTATAAGGTTCCGTCTAAAAAGTTCAAGGTTCT

GGGAAATACAGACCGCCACAGTATCAAAAAAAATCTTATAGGGGCTCTTTTA

TTTGGCAGTGGAGAGACAGCGGAAGCGACTCGTCTCAAACGGACAGCTCGTA

GAAGGTATACACGTCGGAAGAATCGTATTTGTTATCTACAGGAGATTTTTCA

AATGAGATGGCGAAAGTAGATGATAGTTTCTTTCATCGACTTGAAGAGTCTTT

TTTGGTGGAAGAAGACAAGAAGCATGAACGTCATCCTATTTTTGGAAATATA

GTAGATGAAGTTGCTTATCATGAGAAATATCCAACTATCTATCATCTGCGAAA

AAAATTGGCAGATTCTACTGATAAAGCGGATTTGCGCTTAATCTATTTGGCCT

TAGCGCATATGATTAAGTTTCGTGGTCATTTTTTGATTGAGGGAGATTTAAAT

CCTGATAATAGTGATGTGGACAAACTATTTATCCAGTTGGTACAATCTACAA

TCAATTATTTGAAGAAACCCTATTAACGCAAGTAGAGTAGATGCTAAAGCG

ATTCTTTCTGCACGATTGAGTAAATCAAGACGATTAGAAAATCTCATTGCTCA

GCTCCCCGGTGAGAAGAGAAATGGCTTGTTTGGGAATCTCATTGCTTTGTCAT

TGGGATTGACCCCTAATTTTAAATCAAATTTTGATTTGGCAGAAGATGCTAAA

TTACAGCTTTCAAAAGATACTTACGATGATGATTTAGATAATTTATTGGCGCA

AATTGGAGATCAATATGCTGATTTGTTTTTGGCAGCTAAGAATTTATCAGATG

CTATTTTACTTTCAGATATCCTAAGAGTAAATAGTGAAATAACTAAGGCTCCC

CTATCAGCTTCAATGATTAAGCGCTACGATGAACATCATCAAGACTTGACTCT

TTTAAAAGCTTTAGTTCGACAACAACTTCCAGAAAAGTATAAAGAAATCTTTT

TTGATCAATCAAAAAACGGATATGCAGGTTATATTGATGGGGGAGCTAGCCA

AGAAGAATTTTATAAATTTATCAAACCAATTTTAGAAAAAATGGATGGTACT

GAGGAATTATTGGTGAAACTAAATCGTGAAGATTTGCTGCGCAAGCAACGGA

CCTTTGACAACGGCTCTATTCCCCATCAAATTCACTTGGGTGAGCTGCATGCT

ATTTTGAGAAGACAAGAAGACTTTTATCCATTTTTAAAAGACAATCGTGAGA

AGATTGAAAAAATCTTGACTTTTCGAATTCCTTATTATGTTGGTCCATTGGCG

CGTGGCAATAGTCGTTTTGCATGGATGACTCGGAAGTCTGAAGAAACAATTA

CCCCATGGAATTTTGAAGAAGTTGTCGATAAAGGTGCTTCAGCTCAATCATTT

ATTGAACGCATGACAAACTTTGATAAAAATCTTCCAAATGAAAAAGTACTAC

CAAAACATAGTTTGCTTTATGAGTATTTTACGGTTTATAACGAATTGACAAAG
```

-continued

```
GTCAAATATGTTACTGAGGGAATGCGAAAACCAGCATTTCTTTCAGGTGAAC

AGAAGAAAGCCATTGTTGATTTACTCTTCAAAACAAATCGAAAAGTAACCGT

TAAGCAATTAAAAGAAGATTATTTCAAAAAAATAGAATGTTTTGATAGTGTT

GAAATTTCAGGAGTTGAAGATAGATTTAATGCTTCATTAGGCGCCTACCATG

ATTTGCTAAAAATTATTAAAGATAAAGATTTTTTGGATAATGAAGAAAATGA

AGATATCTTAGAGGATATTGTTTTAACATTGACCTTATTTGAAGATAGGGGA

TGATTGAGGAAAGACTTAAAACATATGCTCACCTCTTTGATGATAAGGTGAT

GAAACAGCTTAAACGTCGCCGTTATACTGGTTGGGGACGTTTGTCTCGAAAA

TTGATTAATGGTATTAGGGATAAGCAATCTGGCAAAACAATATTAGATTTTTT

GAAATCAGATGGTTTTGCCAATCGCAATTTTATGCAGCTGATCCATGATGATA

GTTTGACATTTAAAGAAGATATTCAAAAAGCACAGGTGTCTGGACAAGGCCA

TAGTTTACATGAACAGATTGCTAACTTAGCTGGCAGTCCTGCTATTAAAAAG

GTATTTTACAGACTGTAAAAATTGTTGATGAACTGGTCAAAGTAATGGGGCA

TAAGCCAGAAAATATCGTTATTGAAATGGCACGTGAAAATCAGACAACTCAA

AAGGGCCAGAAAAATTCGCGAGAGCGTATGAAACGAATCGAAGAAGGTATC

AAAGAATTAGGAAGTCAGATTCTTAAAGAGCATCCTGTTGAAAATACTCAAT

TGCAAAATGAAAAGCTCTATCTCTATTATCTACAAAATGGAAGAGACATGTA

TGTGGACCAAGAATTAGATATTAATCGTTTAAGTGATTATGATGTCGATCACA

TTGTTCCACAAAGTTTCATTAAAGACGATTCAATAGACAATAAGGTACTAAC

GCGTTCTGATAAAAATCGTGGTAAATCGGATAACGTTCCAAGTGAAGAAGTA

GTCAAAAAGATGAAAAACTATTGGAGACAACTTCTAAACGCCAAGTTAATCA

CTCAACGTAAGTTTGATAATTTAACGAAAGCTGAACGTGGAGGTTTGAGTGA

ACTTGATAAAGCTGGTTTTATCAAACGCCAATTGGTTGAAACTCGCCAAATCA

CTAAGCATGTGGCACAAATTTTGGATAGTCGCATGAATACTAAATACGATGA

AAATGATAAACTTATTCGAGAGGTTAAAGTGATTACCTTAAAATCTAAATTA

GTTTCTGACTTCCGAAAAGATTTCCAATTCTATAAAGTACGTGAGATTAACAA

TTACCATCATGCCCATGATGCGTATCTAAATGCCGTCGTTGGAACTGCTTTGA

TTAAGAAATATCCAAAACTTGAATCGGAGTTTGTCTATGGTGATTATAAAGTT

TATGATGTTCGTAAAATGATTGCTAAGTCTGAGCAAGAAATAGGCAAAGCAA

CCGCAAAATATTTCTTTTACTCTAATATCATGAACTTCTTCAAAACAGAAATT

ACACTTGCAAATGGAGAGATTCGCAAACGCCCTCTAATCGAAACTAATGGGG

AAACTGGAGAAATTGTCTGGGATAAAGGGCGAGATTTTGCCACAGTGCGCAA

AGTATTGTCCATGCCCCAAGTCAATATTGTCAAGAAAACAGAAGTACAGACA

GGCGGATTCTCCAAGGAGTCAATTTTACCAAAAAGAAATTCGGACAAGCTTA

TTGCTCGTAAAAAAGACTGGGATCCAAAAAAATATGGTGGTTTTGATAGTCC

AACGGTAGCTTATTCAGTCCTAGTGGTTGCTAAGGTGGAAAAAGGGAAATCG

AAGAAGTTAAAATCCGTTAAAGAGTTACTAGGGATCACAATTATGGAAAGAA

GTTCCTTTGAAAAAAATCCGATTGACTTTTTAGAAGCTAAAGGATATAAGGA

AGTTAAAAAAGACTTAATCATTAAACTACCTAAATATAGTCTTTTTGAGTTAG

AAAACGGTCGTAAACGGATGCTGGCTAGTGCCGGAGAATTACAAAAAGGAA

ATGAGCTGGCTCTGCCAAGCAAATATGTGAATTTTTTATATTTAGCTAGTCAT
```

-continued

```
TATGAAAAGTTGAAGGGTAGTCCAGAAGATAACGAACAAAAACAATTGTTTG

TGGAGCAGCATAAGCATTATTTAGATGAGATTATTGAGCAAATCAGTGAATT

TTCTAAGCGTGTTATTTTAGCAGATGCCAATTTAGATAAAGTTCTTAGTGCAT

ATAACAAACATAGAGACAAACCAATACGTGAACAAGCAGAAAATATTATTC

ATTTATTTACGTTGACGAATCTTGGAGCTCCCGCTGCTTTTAAATATTTTGATA

CAACAATTGATCGTAAACGATATACGTCTACAAAAGAAGTTTTAGATGCCAC

TCTTATCCATCAATCCATCACTGGTCTTTATGAAACACGCATTGATTTGAGTC

AGCTAGGAGGTGACTGA
```

S. pyogenes Cas9 protein (GENBANK ® accession no. AKP81606.1):
(SEQ ID NO: 156)

```
MDKKYSIGLDIGTNSVGWAVITDDYKVPSKKFKVLGNTDRHSIKKNLIGALLFDS

GETAEATRLKRTARRRYTRRKNRICYLQEIFSNEMAKVDDSFFHRLEESFLVEED

KKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRR

LENLIAQLPGEKKNSLFGNLIALSLGLTPNFKSNFDLAEDAKLQLSKDTYDDDLD

NLLAQIGDQYADLFLAAKNLSDAILLSDILRVNTEITKAPLSASMIKRYDEHHQDL

TLLKALVRQQLPEKYKEIFFDQSKNGYAGYIDGGASQEEFYKFIKPILEKMDGTE

ELLVKLNREDLLRKQRTFDNGSIPHQIHLGELHAILRRQEDFYPFLKDNREKIEKIL

TFRIPYYVGPLARGNSRFAWMTRKSEETITPWNFEEVVDKGASAQSFIERMTNFD

KNLPNEKVLPKHSLLYEYFTVYNELTKVKYVTEGMRKPAFLSGEQKKAIVDLLF

KTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRL

SRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQK

GQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQIL

DSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSLFELENGR

KRMLASAGELQKGNELALPSKYVNFLYLASHYEKLKGSPEDNEQKQLFVEQHK

HYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD.
```

In some cases, the methods provided herein can utilize one or more transcription activator-like effector (TALE) nucleases targeted to the genomic sequence of interest and/or to the donor nucleic acid construct. TAL effectors of plant pathogenic bacteria in the genus *Xanthomonas* play important roles in disease and trigger defense by binding to host DNA and activating effector-specific host genes (see, e.g., Gu et al., *Nature* 435:1122, 2005; Yang et al., *Proc Natl Acad Sci USA* 103:10503, 2006; Kay et al., *Science* 318:648, 2007; Sugio et al., *Proc Natl Acad Sci USA* 104:10720, 2007; and Römer et al., *Science* 318:645, 2007). Specificity depends on an effector-variable number of imperfect, typically 34 amino acid repeats (Schornack et al., *J Plant Physiol* 163:256, 2006). Polymorphisms are present primarily at repeat positions 12 and 13, which are referred to herein as the repeat variable-diresidue (RVD). TALE nucleases contain (1) a DNA binding domain derived from a TAL effector, where the domain can be engineered to bind to a specific sequence based on the RVDs included in the repeats, and (2) an endonuclease domain, typically from a type II restriction endonuclease such as FokI (Kim et al., *Proc Natl Acad Sci USA* 93:1156-1160, 1996). Other useful endonucleases include, for example, HhaI, HindIII, NotI, BbvCI, EcoRI, Bg/I, and AlwI. The fact that some endonucleases (e.g., FokI) only function as dimers can be capitalized upon to enhance the target specificity of the TALE nuclease. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created. Thus, TALE nucleases can function as heterodimers, where each monomer of the pair is targeted to a selected target sequence, and when the monomers are bound to their targets, the nuclease dimerizes and cleaves the DNA at the target sequence between the monomer binding sites. See, e.g., U.S. Pat. No. 8,586,363.

Other rare-cutting endonucleases that can be used in the methods described herein include, without limitation, Cas12a, Mad7, zinc finger nucleases (ZFNs), and meganucleases. Examples of such rare-cutting endonucleases are described elsewhere (see, e.g., Yang et al., Cell, 167:1814-1828, 2016; Carroll, Genetics 188 (4): 773-782, 2011; Stoddard, *Quarterly Rev Biophys* 38 (1): 49-95, 2006).

In some embodiments, the methods provided herein can further include introducing into the cell one or more agents that can facilitate or stimulate DNA cleavage, resection at the cleavage sites to generate ssDNA, integration of the donor sequence, and repair. Such agents can be introduced as RNA, DNA, or polypeptide components, and can act as overexpressed polypeptides or dominant negative molecules to achieve their effect.

In some cases, for example, an agent that assists in DNA resection (e.g., Mre11), can be introduced to stimulate integration and repair. Although not described in the Examples below, an Mre11 overexpression experiment in zebrafish embryos resulted in an estimated percentage of RFP+ notochords of 85% (36 of 42 notochords) when embryos injected with Cas9/UgRNA/Mre11 overexpression, as compared to an estimated 34% (12 of 35) RFP+ notochords with Cas9/UgRNA alone.

Agents that modulate DNA repair by inhibiting non-homologous end joining (NHEJ) also can stimulate integration and repair. Useful NHEJ inhibitors include, without limitation, i53 and dominant negative Ku80. Agents that stimulate single strand annealing/microhomology-mediated end joining (SSA/MMEJ) also can be used in the methods provided herein to stimulate integration and repair. Examples of agents that stimulate SSA/MMEJ include, for example, i53, RPA D215Y, Rad52, Mre11 WT, Mre11 S676A/S678A, LigIII, PolQ, Rad51 K133A, and Rad51 K133R. In addition, agents that stimulate DNA repair can also promote integration donor nucleic acids and repair of DNA breaks. Non-limiting examples of such agents include p53, Rad51, Rad51 K342E, Rad51 I345T, and Rad54. One or more of the foregoing can be introduced into a cell in the methods described herein, in order to facilitate targeted insertion or gene replacement by a donor nucleic acid molecule.

In some cases, in order to facilitate gene replacement, two sequences in the genomic DNA-one on either side of a sequence to be removed—can be targeted for endonuclease cleavage. For example, a first target sequence adjacent to the 5' end of a sequence to be removed, and a second target sequence adjacent to the 3' end of the sequence to be removed, can be targeted by gRNAs to enable Cas9 cleavage, or can be targeted by TALE nucleases designed to specifically recognize those targets. Introduction of (1) a donor nucleic acid construct, along with (2) endonucleases targeted to the donor and to the genomic DNA, (3) one or more gRNA molecules if a Cas9 endonuclease is being used, and (4) any other optional agents being used, can allow cleavage at both genomic targets, removal of the sequence between the genomic targets, and insertion of the donor sequence into the deletion. The resulting sequence can be referred to as a "deletion tagged" allele. The two genomic sequences targeted in such "deletion tagging" methods can be relatively close together (e.g., separated by a few hundred bp, such as 100 to 300 bp, 200 to 500 bp, or 300 to 600 bp), or can be relatively far apart (e.g., separated by 1 kb or more, such as 1 to 5 kb, 5 to 10 kb, 10 to 20 kb, 20 to 30 kb, 30 to 40 kb, 40 to 50 kb, 50 to 100 kb, 100 to 500 kb, 500 to 1000 kb, 1000 to 1500 kb, or 1500 to 2000 kb).

The donor nucleic acid sequence, the rare-cutting endonuclease(s), and any other components used (e.g., gRNA or cleavage/resection/integration/repair promoting agents) can be introduced into the cells as RNA, DNA, polypeptide, or a combination thereof. Further, the donor nucleic acid construct, rare-cutting endonuclease(s), and other components can be introduced into cells by any suitable method. In some cases, for example, microinjection can be used to introduce a donor DNA molecule, one or more gRNA molecules, and a Cas9 mRNA molecule into a cell. Alternatively, electroporation or transfection can be used to introduce a donor DNA molecule, one or more gRNA molecules, and a Cas9 DNA molecule into a population of cells.

As described in the Examples below, the methods described herein can be used to achieve precise genomic modifications that are transmissible to offspring. In some cases, precise targeted modifications can be achieved in at least 20% (e.g., at least 30%, at least 40%, at least 50%, at least 60%, at least 70%, or at least 80% of the cells into which the donor nucleic acid construct and the endonuclease(s) are introduced.

The invention will be further described in the following examples, which do not limit the scope of the invention described in the claims.

EXAMPLES

Example 1—Materials and Methods

Zebrafish husbandry and strains: Zebrafish were maintained in Aquatic Habitats (Pentair) housing on a 14 hour light/10 hour dark cycle. Wild-type WIK were obtained from the Zebrafish International Resource Center. The Tg(mini-Tol2/14XUAS:mRFP, γCry:GFP)$^{tp/2}$, shortened to Tg(UAS:mRFP)$^{tp/2}$, is described elsewhere (Balciuniene et al., *BMC Genomics*, 14:619, 2013).

pGTag series vectors: To build the pGTag vector series, 2A-TagRFP, 2A-eGFP, and 2A-Gal4/VP16 cassettes were assembled from a 2A-TagRFP-CAAX construct, p494 (obtained from the Chi-Bin Chien laboratory at the University of Utah). To clone the eGFP cassette, the plasmid p494 was amplified with primers F-p494-XhoI and R-p494-SpeI to generate unique enzyme sites in the backbone. The eGFP coding sequence (Clontech Inc.) was amplified with the primers F-eGFP-SpeI and R-eGFP-XhoI to generate the corresponding enzyme sites on the eGFP coding sequence. Fragments were digested with SpeI-HF and XhoI (NEB) and following column purification with the Qiagen miniprep protocol, were ligated to the plasmid backbone with T4 ligase (Fisher).

The Gal4/VP16 coding sequence and zebrafish β-actin 3' untranslated region was amplified from vector pDB783 (Balciuniene et al., supra) with primers F-2A-Gal4-BamHI and R-Gal4-NcoI to add a 2A peptide to the 5' end of the Gav4Vp16 cDNA. The resulting PCR product was then cloned into the intermediate Topo Zero Blunt vector (Invitrogen) and used for mutagenesis PCR with primers F and R '-gal4-Ecofix' to disrupt the internal EcoRI restriction site. The resulting Gal4/VP16 sequence was cloned into the BamHI and NcoI sites in the p494 backbone.

The 5' universal/optimal guide site and lacZ cassette were added to pC-2A-TagRFP-CAAX-SV40, pC-2A-eGFP-SV40, and pC-2A-Gal4VP16-β-actin with the following steps. The lacZ was first amplified with primers F-lacZ and R-lacZ, which added the type IIS enzyme sites to either end of the lacZ. The resulting PCR product was then cloned into an intermediate vector with the ZERO BLUNT® TOPO® PCR Cloning Kit (Invitrogen). This intermediate was used as a template in a nested PCR to add the Universal guide sequence GGGAGGCGTTCGGGCCACAGCGG (SEQ ID NO:45; underlining indicates the PAM sequence) to the end of the lacZ sequence. The nested PCR used primers F-lacZ-universal-1 and R-lacZ-universal-BamHI to add the first part of the universal guide to one end and a BamHI site to the other. This was used as template for PCR with the primers F-lacZ-universal-EcoRI and R-lacZ-universal-BamHI to add the remainder of the universal guide and an EcoRI site. The fragment was column purified as above, digested with EcoRI-HF and BamHI-HF and cloned into the appropriate sites in the three vectors.

The 3' universal guide and type 2 restriction enzyme sites were cloned into each vector in two steps. A segment from a Carp beta-actin intron containing a 99 bp spacer flanked by two BspQI sites was amplified using the primers F-3'-uni-1 and R-3'-uni-1 to add the universal site to one side of the spacer. This product was column purified as above and used as template for the second amplification with primers F-3'-uniNco1 and R-3'-uniEagI to add cloning sites. The product was column purified and cloned using the TOPO® ZERO BLUNT® kit. This intermediate was digested with NcoI-HF and EagI, and the BspQI fragment was purified and cloned into the three vectors as above. Ligations were grown at 30° C. to reduce the possibility of recombination between the two universal guide sites.

Correct clones for pU-2A-TagRFP-CAAX-U, pU-2A-eGFP-U, and pU-2A-Gal4/VP16-U were selected and used as templates for mutagenesis PCR with KOD to remove extra BspQI sites from the backbone with primers F/R-BBfix, digested with DpnI (NEB), and ligated with T4 ligase. A correct pU-2A-TagRFP-CAAX-U clone was used as template for PCR with F/R-TagRFPfix to interrupt the BspQI site in the TagRFP coding sequence as above. A correct clone of pU-2A-Gal4/VP16-U was selected and used as template with primers F/R-Bactfix to remove the BspQI site in the Beta-actin terminator, the product was re-cloned as above. All constructs were sequence verified.

Homology arm design and donor vector construction: Detailed methods are provided in Example 2 (Supplementary Gene Targeting Protocol) below. In brief, however, homology arms of specified length directly flanking a genomic targeted double strand break were cloned into the pGTag vector, between the UgRNA sequence and the cargo. A three-nucleotide buffer sequence lacking homology to the genomic target site was engineered between the donor UgRNA PAM and the homology arms, in order to maintain the specified homology arm length. See TABLE 1 for sequences of homology arms, gRNA target sites, and spacers.

GTagHD website development: The webtool GTagHD was developed to assist users in designing oligonucleotides for targeted integration using the pGTag vector suite. GTagHD guides users through entering: (1) the guide RNA for cutting their cargo-containing plasmid; (2) the guide RNA for cutting their genomic DNA sequence; (3) the genomic DNA sequence, in the form of a GenBank accession number or copy/pasted DNA sequence; and (4) the length of microhomology to be used in integrating the plasmid cargo. If the user is utilizing one of the pGTag series plasmids, GTagHD also can generate a GenBank/ApE formatted file for that plasmid, which includes the user's incorporated oligonucleotide sequences. GTagHD is freely available online at genesculpt.org/gtaghd/and for download at github.com/Dobbs-Lab/GTagHD.

Zebrafish embryo injection: pT3TS-nCas9n was a gift from Wenbiao Chen (Addgene plasmid #46757). XbaI linearized pT3TS-nCas9n was purified under RNase-free conditions with the Promega Pure Yield Plasmid Miniprep System. Linear, purified pT3TS-nCas9n was used as template for in vitro transcription of capped, polyadenylated mRNA with the Ambion T3TS mMessage mMachine Kit. mRNA was purified using the Qiagen miRNeasy Kit. Genomic and universal sgRNAs were generated using cloning free sgRNA synthesis as described elsewhere (Varshney et al., Genome Res, 25 (7): 1030-1042, 2015) and purified using Qiagen miRNeasy Kit. Donor vector plasmid DNA was purified with the Promega PureYield Plasmid Miniprep System. noto, cx43.4, tyrosinase, and moesina, were targeted by co-injection of 150 pg of nCas9n mRNA, 25 pg of genomic sgRNA, 25 pg of UgRNA (when utilized), and 10 pg of donor DNA diluted in RNAse free ddH$_2$O. The rb1 targeting mixture contained 300 pg nCas9n mRNA. 2 nl was delivered to each embryo.

Recovery of zebrafish germline knock-in alleles: Injected animals were screened for fluorescence reporter expression on a Zeiss Discovery dissection microscope and live images captured on a Zeiss LSM 700 laser scanning confocal microscope. RFP/GFP positive embryos were raised to adulthood and outcrossed to wildtype WIK adults to test for germline transmission of fluorescence in F1 progeny. tyr, esama, rb1 and msna embryos targeted with Gal4VP16 were crossed to Tg(UAS:mRFP)$^{tp12}$.

DNA isolation and PCR genotyping: Genomic DNA for PCR was extracted by digestion of single embryos in 50 mM NaOH at 95° C. for 30 minutes and neutralized by addition of $\frac{1}{10}^{th}$ volume 1M Tris-HCl pH 8.0. Junction fragments were PCR-amplified with primers listed in TABLE 5, and the products were TOPO-TA cloned before sequencing.

Southern blot analysis: Genomic Southern blot and copy number analysis was performed as described elsewhere (McGrail et al., PLoS One, 6 (4): e18826, 2011). PCR primers used for genomic and donor specific probes are listed in TABLE 5.

Example 2—Supplementary Gene Targeting Protocol for Integrations with pGTag Vectors Using CRISPR/Cas9

To carry out a gene targeting strategy (FIGS. 1A and 1B), one can use methods that include the following steps:
(A) select a CRISPR/spCas9 (Streptococcus pyogenes Cas9) target site downstream of the first AUG in the gene of interest;

(B) synthesize sgRNA and spCas9 mRNA;
(C) inject sgRNA and spCas9 mRNA;
(D) test for indel production/mutagenesis;
(E) design short homology arms;
(F) one pot cloning of homology arms into pGTag vectors;
(G) inject GeneWeld reagents (spCas9 mRNA, Universal sgRNA (UgRNA), genomic sgRNA, and pGTag homology vector) into 1-cell zebrafish embryos; and
(H) examine embryos for fluorescence and junction fragments.

Instructions for these steps are further described below.

A. Selection of a CRISPR/spCas9 Target Site Downstream of the First AUG in the Gene of Interest (1) To select a CRISPR/Cas9 target site in a 5' exon, find and download the targeted gene's genomic and coding sequences.
  (a) At <ensemble.org> Search for the gene name of interest for the species of interest and open the Transcript page.
  (b) In the left-hand side bar click on "Exons" to find the first coding exon and initiation ATG. If there are alternative transcripts for the gene, make sure there are not alternative initiation ATGs. If there are alternative start codons, target the first 5' exon that is conserved in all transcripts to generate a strong allele.
  (c) Download the transcript and 5' exon to be targeted as separate sequence files.
  (d) Using ApE (biologylabs.utah.edu/jorgensen/wayned/ape/), annotate the coding sequence with the exons.

Figure 2:
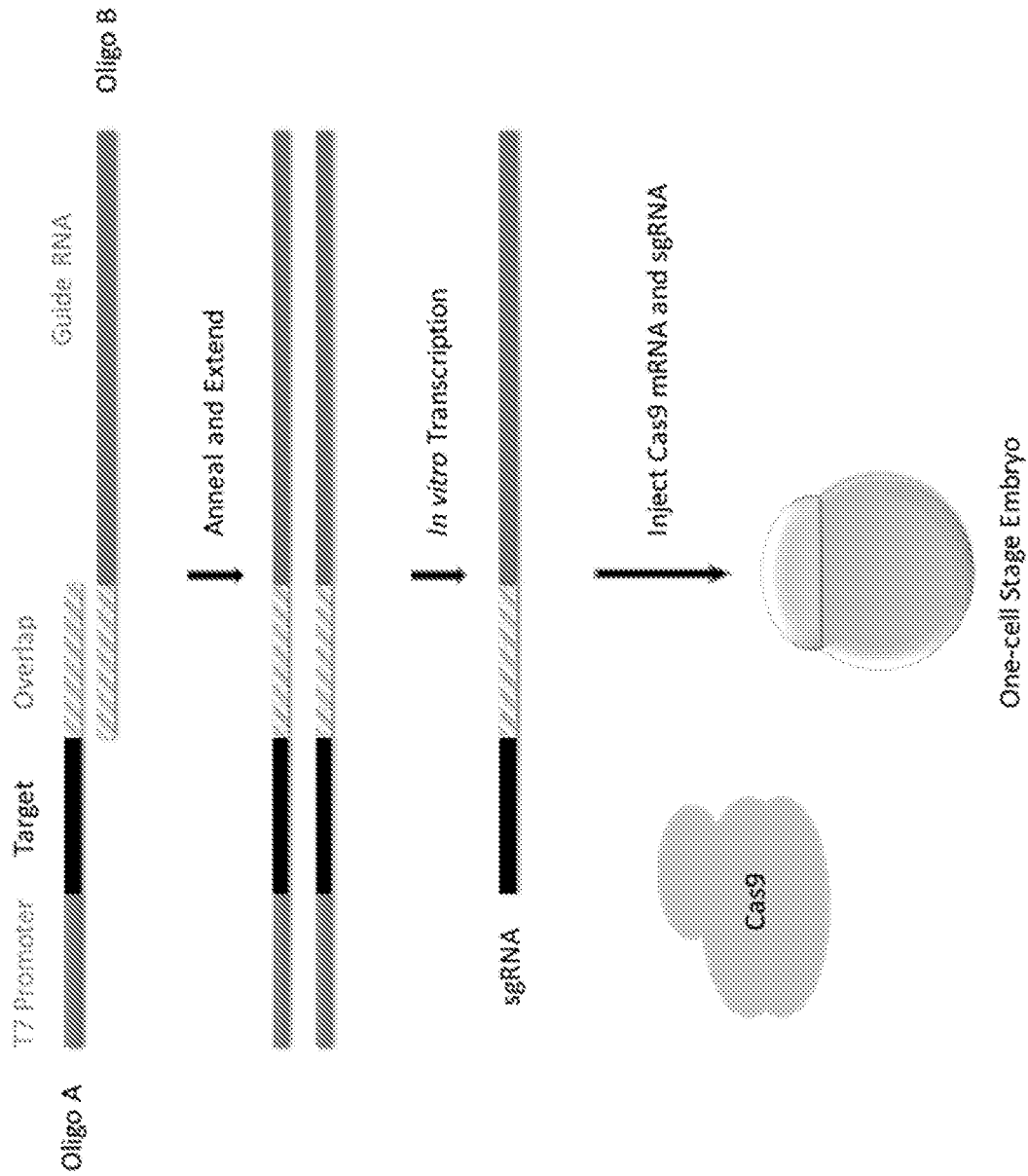
FIG. 2 is diagram of a method for cloning-free gRNA synthesis. Oligo A is composed of the T7 promoter at the 5' end, target sequence for gRNA, and gRNA overlap sequence for gRNA synthesis. CRISPRScan can provide a direct output for Oligo A.

(2) Use CRISPRScan (crisprscan.org/; Moreno-Mateos et al., *Nat Methods,* 12 (10): 982-988, 2015) to identify target sites and generate oligos for sgRNA synthesis for the target gene.
  (a) Select "Predict gRNAs" on the lower right-hand side of the home page of the CRISPRScan website.
  (b) Paste the 5' exon sequence into the indicated box. If the exon is very large, start with a small amount of sequence. Ideally, use an exon sequence of ~200 bp near the desired target site. Do not design CRISPRs to intron/exon borders. If there are problems with the copy and pasting of exon sequence, first paste the sequence into a new ape file, save, then copy and paste from the new file.
  (c) Select "Zebrafish (*Danio rerio*)" as the species.
  (d) Select "Cas9—nGG" as the enzyme.
  (e) Select "In vitro T7 promoter".
  (f) Click on "Get sgRNAs." Examine the output. The generated targets are ranked by CRISPRScan from high to low. Select a target site (the 20 bp that are capitalized in the oligo column) from those given by CRISPRScan using the following criteria (The best gRNAs will have all of these):
    (i) An exact match to the genomic locus. When an oligo is clicked on, the page displays additional information to the right. Any mismatches in the oligo are displayed in the section called "Site Type." Exact matches including 5'GG- are ideal for in vitro transcription and 100% genomic target match.
    (ii) The target is in the desired location of the gene.
    (iii) The Target is on the reverse (template) strand. Reverse strand guides are more favorable, but either will work.
    (iv) A high CRISPRScan score, and a lower CFD score. However, lower score sgRNA targets may work fine.
  (g) Annotate the selected target sequence in the transcript sequence files.
  (h) For sgRNA synthesis, the entire oligo sequence from CRISPRscan containing the selected target will need to be synthesized. This oligo is represented as "Oligo A" in FIG. 2.

(3) Alternative to CRISPRScan: Designing "CRISPR Oligo A" from a genomic target sequence. Do not use this section if Oligo A was designed with CRISPRScan. If the target sequence was identified using tools other than CRISPRScan, Oligo A can be designed manually. (Note: CRISPRScan will use a shorter overlap region but this does not affect template production.) Add T7 and Overlap sequences (see FIG. 2) to the 20 bp of target sequence without the PAM. Oligo A for the targeted gene will look like:

(SEQ ID NO: 46)
5'-<u>TAATACGACTCACTATAGG</u>NNNNNNNNNNNNNNNNNNNNGTTTTAGA

GCTAGAAATAGC-3'

The first 19 nucleotides (underlined) are the T7 promoter, nucleotides 18 and 19 (GG) are part of the T7 promoter and ideally are part of the target sequence (see below), the Ns are the target sequence, and the last 20 nucleotides (bold) are the overlap region to synthesize the non-variable part of the sgRNA. The T7 promoter works optimally with the GG dinucleotide shown at positions 18 and 19, but these bases will be transcribed by T7 and thus become a part of the sgRNA. Target sequences that contain the GG sequence may work better, but there are differing reports on the importance of this (Moreno-Mateos et al., supra). If possible, select a target that starts with GG. Refer to Moreno-Mateos et al. (supra) for other gRNA architectures with variations on the 5'GG motif.
  (a) If the target sequence does not have two Gs at the beginning, add G's to the start of the target sequence for most efficient transcription, as follows. The lower case 'g' in the following sequences is an extra 'G' not in the genomic sequence; the upper-case G is in the genomic sequence. Lower case g's will not base pair with the genomic target.
    (i) without GG: ggNNNNNNNNNNNNNNNNNNNN (22 bp; SEQ ID NO:47)—2 bases are added.
    (ii) with one G: gGNNNNNNNNNNNNNNNNNNNN (21 bp; SEQ ID NO:47)—one base is added, G is part of the target sequence.
    (iii) with GG: GGNNNNNNNNNNNNNNNNNNNN (20 bp; SEQ ID NO: 47)—no bases are added; GG is part of the target sequence.
  Oligo A is made by taking this target sequence with 5'-GG and pasting it into a clean file.
  (b) Copy and paste the T7 promoter sequence to the 5' end of the target sequence: TAATACGACTCACTATA (SEQ ID NO:48).
  (c) Copy and paste the Overlap sequence to the 3' end of the target sequence: GTTTTAGAGCTAGAAATAGC (SEQ ID NO:49).
  (d) Check the sequences to ensure they are correct and that the PAM is NOT present in this oligo.

(4) Oligo B (FIG. 2) contains the conserved guide RNA sequence. All Oligo Bs will be the same and can be ordered in large quantities. The sequence is 5'-GATCCGCACCGACTCGGTGCCACTTTTTCAAGTTGATAACGGACTA GCCTTATTTTAACTTGCTATTTCTAGCTCTAAAAC-3' (SEQ ID NO:50).

(5) To increase yield of the sgRNA synthesis, the primers "T7 primer" (5'-TAATACGACTCACTATA-3'; SEQ ID NO:48) and "3'gRNA primer" (5'-GATCCGCACCGACTCGGTG-3'; SEQ ID NO:51) also are required.

(6) For checking for mutagenesis at the target site, design ~20 bp DNA primers for PCR amplification to amplify at least 130 bp of DNA surrounding the target site. Mutagenesis is estimated through comparison of PCR products from injected and uninjected embryos, by visualizing small insertions and/or deletions (indels) using electrophoresis, or by sequencing.

(a) Primer3 is used for primer design (biotools.umassmed.edu/bioapps/primer3_www.cgi).
(b) Paste DNA sequence surrounding the target site into the web interface. It is recommended to use 160-300 bp of exon sequence centered on the cut site for primer design. Intron sequence can be used, but this often contains polymorphisms that can lead to amplification failure.
(c) Locate the target sequence, including the PAM sequence (italicized below), and predict the cut site (3 bp into the target sequence upstream from the PAM sequence, represented here by the '|'). Mark the targeted exon sequence about 65-150 bp on both sides of the cut site by putting [square brackets] around it. Primer3 will design primers outside this sequence. This design allows the primers to be used for both checking of mutagenesis and for junction fragment analysis when checking for integration.

Example (SEQ ID NO: 52)
CGGCCTCGGGATCCACCGGCC[AGAATCGATATACTACGATGAA

CAGAGCAAATTTGTGTGTAATACGGTCGCCACCATGGCCT|CCT

*CGGTTTGCTACGATGCATTTGCACCACTCTCTCATGTCCGGTTCT*

GGG]AGGACGTCATCAAGGAGTTCATGCGCTTCAAGGTGCGCAT

GGAGGGCTCCGTGAAC.

(d) Set the "Primer Size" variables to Min=130, Opt=170, and Max=300. Everything else can be left at the defaults.
(e) Click on "Pick Primers."
(f) Select primers from the output. Note the "product size" expected and the "tm" or melting temperature of each primer/pair. Smaller product sizes are easier for visualizing mutagenesis.

B. Synthesize the sgRNA

Use general guidelines and good laboratory practices for working with DNA and RNA, since DNA, RNA and the enzymes are sensitive to contamination from dust and skin. Following these guidelines will prevent the degradation of DNA and RNA.

Clean the workbench, pipetmen, racks, and centrifuges with RNase Away or something equivalent.
Wear gloves and change when contaminated. Contamination will occur when gloves contact hair, face, skin, or the floor.
Keep everything on ice unless the protocol indicates otherwise.
Centrifuge components to the bottom of the tube before use, after mixing, after use, and after incubation steps.
Do not vortex enzymes. Gently flick the tube or pipet up and down to mix samples.
Avoid touching the walls of the tube when pipetting.
Use a new pipette tip for each new dip.
Dispense solutions from a pipet to the bottom of the tube, or into the liquid at the bottom of the tube when setting up reactions.
Only remove 1.5 ml centrifuge tube and PCR tubes from their package while wearing gloves. Reseal the tube package after tubes are removed.

Assembly of CRISPR Oligos A+B into a Transcription Template (1) For synthesis of the gRNA from Oligo A and B, make a 100 µM freezer stock and 1 µM working stock for each oligo. All oligos are described in Section A above.
(2) Centrifuge ordered oligos briefly before opening, to move all dried DNA flakes to the bottom of the tube.
(3) Add a volume (x µL) of RNase-free water to make a 100 µM stock. The tubes should be labeled with the gene name as well as the number of nmol in the tube. The amount of water to be added will need to calculated based on the nanomoles of material contained within.
(4) Vortex for 30 seconds.
(5) Centrifuge briefly.
(6) Make a 100-fold dilution of each 100 µM stock Oligo A and B in separate 1.5 ml tubes.
  (a) Label one 1.5 mL centrifuge tube per Oligo A with name of oligo, date, and "1 µM" to indicate working stocks. Add 1 µL of 100 µM Oligo A stock or Oligo B and 99 µL of RNF-water for a total of 100 µL.
  (b) Vortex.
  (c) Briefly centrifuge.
  (d) Store all stocks at −20° C. for long-term storage.
(7) Set up the following reaction in PCR tubes. The next two steps will generate a short segment of DNA (gDNA or guideDNA Template) which will be used as a template for synthesis of RNA:
  12.5 µL 2×KOD Master Mix
  1 µL Oligo A (1 µM)
  1 µL Oligo B (1 µM)
  1 µL T7 primer (10 µM)
  1 µL gRNA 3' primer (10 µM)
  8.5 µL RNF-water
  25 µL total
(8) Run PCR under the following conditions:
  denature at 98° C. for 2 minutes;
  denature at 98° C. for 30 seconds;
  anneal at 50° C. 30 seconds;
  extend at 70° C. 30 seconds;
  repeat steps 2-4 (the 30 second steps) nine times;
  extend at 70° C. 2 minutes; and
  hold at 4° C.
(9) Run a 1.2% agarose gel in 1×TAE to check that the template was synthesized.
  (a) Remove 3 µL of the reaction and place in a 1.5 ml tube.
  (b) Mix in 1 µL of 6× loading buffer.
  (c) Load all 4 µL of the sample on the gel. Run the gel at 125 V for 30 minutes. Include a molecular weight marker.
  (d) Check on the transilluminator and image the gel.
  (e) A single 120 bp band should be detected when 3 µL is loaded on gel.

In Vitro Transcription (IVT) Using the gRNA Template (1) Use the Ambion T7 Megascript Kit for transcription reagents, following the below instructions.
(2) Thaw the T7 10× Reaction Buffer and RNF-water at room temperature, and thaw the ribonucleotides solutions on ice.

(3) Vortex the T7 10× Reaction Buffer to make sure all DTT is solubilized. No white flecks should be visible.

(4) Microcentrifuge all reagents briefly before opening to prevent loss of reagents and/or contamination by materials that may be present around the rim of the tube(s).

(5) Keep the T7 Enzyme Mix on ice or in a −20° C. block during assembly of the reaction.

(6) Make a master mix for each reaction. Assemble the reaction at room temperature on the bench. Add reagents from largest to smallest volume, adding the 10× Reaction Buffer second to last and the T7 Enzyme Mix last.

Note: Components in the transcription buffer can lead to precipitation of the template DNA if the reaction is assembled on ice. If the reaction precipitates, the synthesis reaction will not fully occur.

(7) Reagent list:
10 µL of RNF-water
5 µL of gDNA template (100 to 500 ng total)
4 µL of NTP (1 µl of each; A, U, C, G)
1 µL of 10× transcription buffer-must be fully resuspended at room temp
1 µL of T7 polymerase enzyme mix (8) Incubate at 37° C. for 4 to 16 hours. Longer incubations result in considerably better yields.

(9) Add 1 µL of Turbo DNAse and incubate for 15 min at 37° C. This will digest the template DNA in the sample.

(10) Optional quality control step: Run 2 µL of sample on a 1.2% gel in 1× TAE.
  (a) Clean the gel box, comb and tray with RNase Away, rinse with DI water.
  (b) Remove 2 µl of sample into a clean 1.5 ml (keep RNA on ice).
  (c) Add 3 µL of RNF-water and 5 µL of Ambion RNA loading buffer with formamide.
  (d) Vortex briefly.
  (e) Spin down samples briefly.
  (f) Run the entire mixture on a 1.2% agarose gel/1×TAE, at 100 V for 1 hour.
  (g) Image the gel. Two bands should be visible at ~100 and 120 bp.

Purification of Guide RNA (1) Use the miRNeasy Qiagen kit for purification of gRNAs according to the manufacturer's instructions.

(2) After purification, verify the presence of RNA by running a 1.2% gel in 1×TAE.

(3) Clean the gel box, comb and tray with RNase Away, rinse with DI water. Run on a 1.5% agarose gel/1×TAE, at 100 V for 1 hour as above.

(4) Image the gel. Two bands should be visible at ~100 and 120 bp.

(5) Nanodrop the RNA sample to determine the concentration.

(6) Store RNA at −20° C.

Preparation of SpCas9 mRNA (1). Digest ~5-10 µg pT3TS-nCas9n plasmid with Xba1 (plasmid Addgene #46757; Jao et al., *Proc Natl Acad Sci USA*, 110 (34): 13904-13909, 2013).

(2) Purify digested DNA with Qiagen PCR cleanup kit or Promega Pure Yield Plasmid Miniprep System. Elute in RNF-water.

(3) Run 100-500 ng on 1.2% agarose gel in 1×TAE to confirm the plasmid is linearized.

(4) Use 100 ng to 1 µg DNA as template for in vitro transcription reaction.

(5) Use mMESSAGE mMACHINE T3 kit Life Technologies (AM1348) and follow the instructions in the manual.

(6) Use the miRNeasy Qiagen kit for purification of nCas9n mRNA according to the manufacturer's instructions.

(7) Verify mRNA integrity by mixing 1 µL of purified Cas9, 4 µL of RNF water, 5 µL glyoxl dye (Ambion).

(8) Heat mixture at 50° C. for 30 minutes, then place on ice.

(9) Clean the gel box, comb and tray with RNase Away, rinse with DI water.

(10) Run all 10 µL of RNA mixture on 1.2% agarose gel in 1×TAE at 100 V for 1 hour as above. One band should be visible at 4.5 kb.

(11) Nanodrop the RNA sample to determine the concentration. Concentrations between 0.45 and 1 µg/µL are expected.

(12) Aliquot and store RNA at −80° C.

C. Injection of sgRNA and spCas9 mRNA

The injections are designed to deliver 25 pg of gRNA and 300 pg of Cas9 mRNA in 2 nL of fluid to embryos at the one-cell stage. Injection trays are cast with 1.2% agarose with 1× embryo media (Zebrafish Book; zfin.org) in polystyrene petri dishes (Fisher No. FB0875713). Injection trays can be used multiple times and stored at 4*C for up to three weeks between use.

(1) Trays are pre-warmed to 28.5° C. prior to injection by placing them in a 28.5° C. incubator. Mitigate tray cooling while not in use.

(2) Glass needles are pulled from Kwik-Fil borosilicate glass capillaries (No. 1B100-4) on a Flaming/Brown Micropipette puller (Model P-97). Injection samples are made to contain the following diluted in RNF water or injection buffer (final concentration: 12.5 mM HEPES pH 7.5, 25 mM Potassium Acetate, 37.5 mM Potassium Chloride, 0.0125% glycerol, 0.025 mM DTT pH 7.5)
  (a) 12.5 ng/µL of genomic gRNA
  (b) 150 ng/µL of mRNA for Cas9

(3) Needles are loaded with 1.5 to 2.5 µL of sample, and then loaded onto a micro-manipulator attached to a micro injector (Harvard Apparatus PLI-90) set to 30-40 PSI with an injection time of 200 msec.

(4) Needles are calibrated by breaking the end of the tip off with sterile tweezers, ejecting 10 times to produce a droplet of fluid, collecting the droplet into a 1 µL capillary tube (Drummond No. 1-000-0010), and measuring the distance from the end of the capillary to the meniscus of the droplet. This distance is converted to volume (where 1 mm=30 nL) and adjusted to achieve an effective injection volume of 2 nL. Volumes are adjusted by changing the injection time. There is a linear relationship between volume and time at a set pressure. Avoid injection times less than 100 msec and over 400 msec.

(5) One cell embryos that have been collected from mating cages are pipetted from collection petri dishes to the wells on the injection tray.

(6) Use the micro-manipulator and microscope to pierce the one-cell embryos on the injection tray at an angle of 30° with the needle, and inject 2 nL of sample near the center of the cell-yolk boundary.

(7) After embryos have been injected, wash them from the injection tray into a clean petri dish with embryo media.

(8) Keep 20 to 40 embryos separate as uninjected controls. Treat and score the control embryos in the same way as the injected embryos.

(9) At 3 to 5 hours post injection, remove any unfertilized or dead embryos from the dishes. This will prevent death of the still developing embryos.

D. Test for Indel Production/Mutagenesis
Phenotypic Scoring of Embryos (1) The gRNA itself may be toxic to the developing embryos. Injection toxicity can be estimated by the number dead embryos from a round of injection compared to the un-injected control dish. Count and remove any brown/dead embryos from injected and un-injected dishes. If there are significantly more dead embryos in the injected dish then the guide may be toxic, impure, or very effective at disrupting a required gene. Reducing the amount of guide or Cas9 mRNA injected may help reduce toxicity.

(2) Score and document embryonic phenotypes on days 1-4 post fertilization (dpf). Under a dissection microscope examine the un-injected controls and injected embryos, and sort the embryos into categories.

(3) Scoring categories

Severe: These embryos have some parts that look like a control embryos, but are missing key features. Examples: embryos that lack their head, eyes, or tail, or embryos that have an unnaturally contorted shape or are asymmetric.

Mild: These embryos appear mostly normal, but have slight defects such as small eyes, pericardial edema, shortened trunk/tail, or curled/twisted tails.

Normal: Embryos appear normal and similar to controls.

Digestion of Embryos for Isolation of Genomic DNA for Mutagenesis Analysis

Genomic DNA (GDNA) can be isolated from zebrafish embryos aged between 1 and 5 dpf using this protocol. Embryos can be analyzed as individuals or as pools (maximum 5) from the same injection.

(1) Dechorionate embryos, if they have not emerged from the chorion.

(2) It is recommended to screen a minimum of 3 embryos from each scoring category for mutagenesis. Place each embryo, including controls, into separate PCR tubes. Remove as much of the fish water as possible. If needed, spin briefly and remove additional water.

(3) Add 20 μL of 50 mM NaOH per embryo.

(4) Heat the embryos at 95° C. in a thermocycler for 15 minutes.

(5) Vortex samples for 10 seconds. Be sure that the tubes are sealed to prevent sample loss while vortexing.

(6) Spin samples down and heat for an additional 15 min at 95° C. in a thermocycler.

(7) Vortex samples and then spin the tubes down again. The embryos should be completely dissolved.

(8) Neutralize the samples by adding 1 μL of 1 M Tris pH 8.0 per 10 μL NaOH. Mix by vortexing then spin down.

(9) Genomic DNA should be kept at 4° C. while in use and stored at −20° C.

Analysis of CRISPR/Cas9 Mutagenesis Efficiency at Targeted Gene Locus.

(1) Set up the following PCR reactions for each tube of digested embryos using the primers designed at the end of section A.

12.5 μL of 2× GoTaq Mastermix
1 μL of Forward Primer (10 μM)
1 μL of Reverse Primer (10 μM)
1 μL of gDNA template (digested embryos)
9.5 μL of nuclease-free water
25 μL total (2) Vortex and briefly spin down the PCR reactions.

(3) Run the following PCR program to amplify the targeted locus.

| 95° C. | 2 minutes | |
| 95° C. | 30 seconds | |
| 55° C.* | 30 seconds | × 35 cycles |
| 72° C. | 30 seconds | |
| 72° C. | 5 minutes | |
| 4° C. | hold | |

*If the primers were designed with higher or lower melting temperatures (tm's) than the annealing temperature in line three (the 55° C. step), then that temperature will need to be adjusted to 2° C. below the designed primer tm.

(4) Run up to 7 μL of PCR product on a 3.0% agarose gel, 1×TAE, for 1 hour at 80-100V.

(5) Analyze the gel for DNA bands that appear diffuse or different in size from the control lane. This indicates that the presence of indels in the gene of interest.

(6) Alternatively, clone and sequence PCR products or sequence them directly to verify the presence of indels.

E. Design Short Homology Arms

Figure 3:
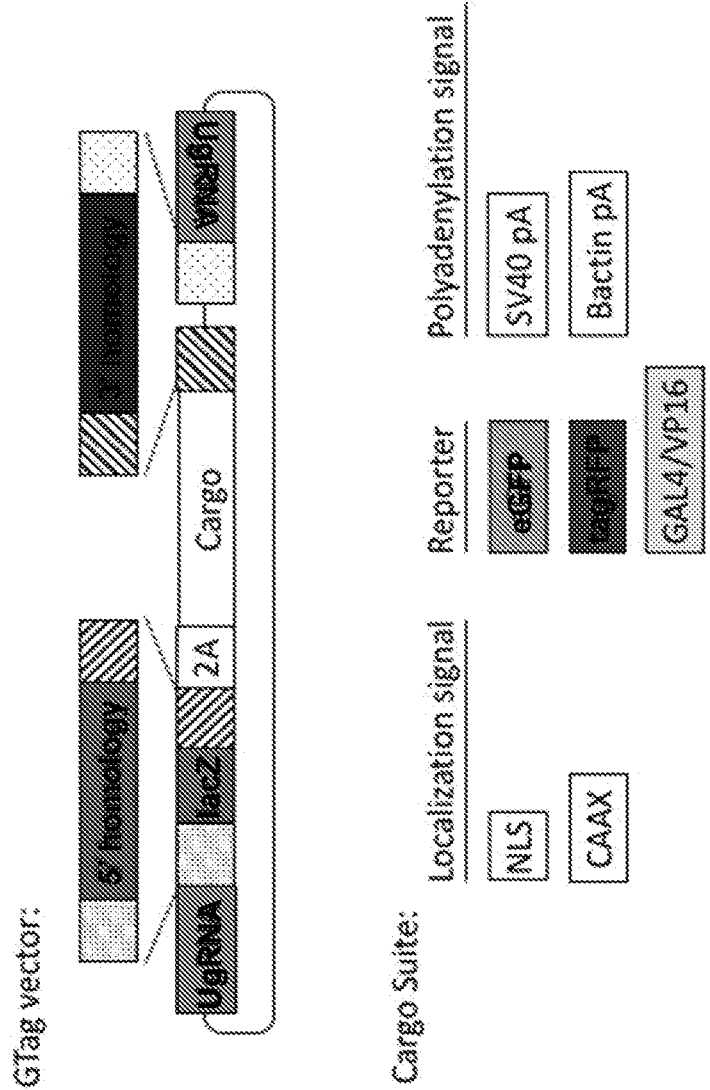
FIG. 3 is a schematic of pGTag vectors that can allow one step cloning of homology arms.

Homology directed gene targeting allows the integration of exogenous DNA into the genome with precision to the base pair level. However, designing and cloning individual targeting vectors and homology arms for each gene of interest can be time consuming. The pGTag vector series provides versatility for ease of generation of knockout alleles (FIG. 3). The vectors contain BfuAI and BspQI type II restriction enzymes for cloning of short homology arms (24 or 48 bp) using Golden Gate cloning. The pGTag vectors require in-frame integration for proper reporter gene function. The reporter gene consists of several parts. First, a 2A peptide sequence causes translational skipping, allowing the following protein to dissociate from the locus peptide. Second and third, eGFP, TagRFP, or Gal4VP16 coding sequences for the reporter protein have a choice of sequence for localization domains, including cytosolic (no) localization, a NLS, or a membrane localization CAAX sequence. Finally translation is terminated by one of two different pA sequences; a β-actin pA from zebrafish or the SV40 pA.

For many genes, the signal from integration of the report protein is too weak to observe. In these cases the Gal4VP16 vector allows for amplification of the report to observable expression levels in FOs and subsequent generations. A 14XUAS/RFP Tol2 plasmid is provided to make a transgenic line for use with the Gal4VP16 vector. Sequence maps for these plasmids can be downloaded at genesculpt.org/gtaghd/.

Because the pGTag plasmids contain repeated sequences, they may be subject to recombination in certain strains of bacteria. It is strongly recommended that they are propagated at 30° C. to reduce the possibility recombination.

The web tool, GTagHD <http://genesculpt.org/gtaghd/>, allows for quick design of cloning ready homology arm oligos for a gene of interest. To use the tool, choose the "Submit Single Job" tab. Follow the instructions in the tab.

There should be four oligos (two pairs that will be annealed) generated for cloning. If there are any problems with the sequences and values that were entered, the web page will display the errors and give advice on how to fix them.

The following protocol describes how to design homology arm oligos manually. When orientation words are used, they are used in the context of the reading frame of the genetic locus of interest. For example, the phrase "5' template strand CRISPR" means that the target site for the CRISPR is on the template strand at the locus and is toward the 5' end of the gene. Upstream homology domains are 5' of the CRISPR cut and downstream homology domains are 3' of the cut with respect to the gene being targeted. Also of note, upper case and lower case bases are not specially modified; they are merely shown the way they are as a visual marker of the different parts of the homology arms.

For the Upstream Homology Domain (1) Open the sequence file for the gene of interest and identify the CRISPR site. Copy the 48 bp 5' of the CRISPR cut into a new sequence file; this is the upstream homology.

(2) Observe the next three bases immediately upstream of the 48 bp of homology, and pick a base not present to be the 3 bp spacer between the homology and the Universal PAM in the vector. For example, if the three bases are GGA, the spacer could be CCC. Add the spacer to the new file 5' (in front) of the homology. The spacer acts a non-homologous buffer between the homology and the eventual 6 bp flap from the universal guide sequence that will occur when the cassette is liberated and may improve intended integration rates over MMEJ events.

(3) Determine where the last codon is in the homology. Complete the codon as needed by adding the remaining bases (called padding on GTagHD) for that codon from the sequence, to ensure that the integration event will be in frame.

(4) Add the BfuAI enzyme overhang sequences for cloning, to the ends of the homology domain (5'-GCGG and 3'-GGAT).

5) The Upstream Homology Oligo A will be this sequence, from the beginning to the end of the last codon. Copy and paste this sequence into a new file and save it.

(6) The Upstream Homology Oligo B will be the reverse compliment of this sequence from beginning of the spacer to the end of the sequence. Copy the reverse compliment, paste it into a new file, and save it.

For the Downstream Homology Domain (7) Open sequence file for the gene of interest and identify the CRISPR site. Copy the 48 bp 3' of the CRISPR cut into a new sequence file; this is the downstream homology.

(8) Observe the next three bases downstream of the 48 bp of homology, and pick a base not present to be the 3 bp spacer between the homology and the Universal PAM in the vector. For example, if the bases are CTG, AAA could be chosen as the spacer. Add the spacer to the new file 3' of (after) the homology.

(10) Add the BspQI enzyme overhang sequences for cloning to the ends of the homology domain (5'-AAG and 3'-CCG).

(11) The Downstream Homology Oligo A will be this sequence, from the beginning of the sequence to the end of the spacer.

(12) The Downstream Homology Oligo B will be the reverse compliment of this sequence, from the beginning of the homology to the end of the sequence.

F. One Pot Cloning of Homology Arms into pGTag Vectors

Note that if the homology arm oligos contain either the sequence 5'-ACCTGC-3 or 5'-GAAGAGC-3 (or their compliment), the cloning reaction will be less efficient. Also note that some sequences do not work very well. Ligation also is possible with annealed homology arms and the purified ~1.2 kb and ~2.4 kb fragments from vectors that have been digested with BfuAI and BspQI.

(1) Homology Arm Annealing

Anneal upstream and downstream homology oligo pairs separately:
 4.5 µL oligo A at 10 µM
 4.5 µL oligo B at 10 µM
 4 µL 10× Buffer 3.1 from NEB
 27 µL dH$_2$O
 total=40 µL Incubate at 98° C. for 4 minutes, and 98° C. 45 seconds× 90 steps decrementing temp 1° C./cycle, 4° C. hold. (Alternatively, heat in 95-98° C. water for 5 minutes, and then remove the boiling beaker from the heat source and allow it to cool to room temp for 2 hours, before placing samples on ice.)

(2) One-Pot Digest

Assemble the following:
 4.0 µL dH$_2$O
 2 µL Plasmid at 50 ng/µL
 1 µL 10× Buffer 3.1 from NEB
 1 µL 5' annealed homology arm
 1 µL 3' annealed homology arm
 0.5 µL BfuAI enzyme from NEB
 0.5 µL BspQI enzyme from NEB
 10 µL total Incubate at 50° C. for 1 hour and place on ice.

(3) Ligation

Add the following:
 3 µL 5× T4 quick ligase buffer
 1.5 µL dH$_2$O
 0.5 µL T4 quick ligase
 15 µL total Incubate 8-10 minutes to overnight at room temperature. Store at −20° C.

(4) Transformation (a) On ice, thaw 1 (one) vial competent cells (50 µL) for every 2 ligation reactions (about 5 minutes). It is recommended to use NEB Stable Competent *E. coli* (C3040H) cells to limit recombination.

(b) While cells are thawing, label the microcentrifuge tubes for each ligation and put on ice.

(c) Once the cells are thawed, use a pipette to transfer 25 µL of the competent cells into each labeled tube.

(d) Add 1.5 µL of a ligation reaction into competent cells to transform. The amount of ligation reaction added should be less than 5% of the volume of competent cells.

(e) Mix by tapping the tube several times or gently mixing with the pipet tip. Do not mix by pipetting, as this can lyse the cells.

(f) Incubate on ice for 5 to 20 minutes.

(g) Heat shock the cells by submerging the portion of the tube containing the cells in a 42° C. water bath for 40-50 seconds.

(h) Incubate cells on ice for 2 minutes.

(i) Add 125 µL of room temperature LB to each transformation.

(j) Incubate cells at 30° C. for 1-1.5 hours in a shaking incubator.

(k) While the transformed cells are recovering, spread 40 µL of X-Gal solution, and 40 µL IPTG 0.8 M on LB Kanamycin selection plates. Since X-Gal is lethal to cells while wet, it is recommended to first label the plates and then place them in a 30° C. incubator to dry.

(l) After recovery and X-Gal drying, plate 150 µL of each transformation on the corresponding correctly labeled plate.

(m) Incubate plates overnight at 30° C.

(5) To Grow Colonies, Pick 3 White Colonies from Each Plate and Grow in Separate Glass Culture Tubes with 3 mL LB/Kanamycin. Alternatively, Pre-Screen Colonies by Colony PCR.

(a) Pick up to 8 colonies with a pipet tip and resuspend them in separate aliquots of 5 µL dH$_2$O. Place the tip in 3 ml of LB/Kan, label, and store at 4° C.

(b) Make a master mix for the PCR reactions containing the following amounts times the number of colonies picked.

7.5 μL 2× Gotaq mastermix
5.5 μL dH$_2$O
0.5 μL primer at 10 μM "F3'-check"

5'-GGCGTTGTCTAGCAAGGAAG-3' (SEQ ID NO: 53)

0.5 μL primer at 10 μM "3'_pgtag_seq"

5'-ATGGCTCATAACACCCCTTG-3' (SEQ ID NO: 54)

14 μL total (c) Aliquot 14 μL of mixed master mix into separate labeled PCR tubes.
(d) Add 1 μL of colony to each reaction as template.
(e) Alternatively, add 20 ng purified plasmid as control.
(f) Cycle in a thermocycler

| | | |
|---|---|---|
| 95° C. | 2 minutes | |
| 95° C. | 30 seconds | |
| 57° C. | 30 seconds | × 35 cycles |
| 72° C. | 30 seconds | |
| 72° C. | 5 minutes | |
| 4° C. | hold | |

(g) Run 5 μL of PCR product on a 1% agarose gel. Bands should be of different sizes than the control.
(6) Mini Prep Cultures Following the Qiagen Protocol.
(7) Sequencing of Plasmids The 5' homology arm can be sequenced using the 5'_pgtag_seq primer: 5'-GCATGGATGTTTTCCCAGTC-3' (SEQ ID NO:55). The 3' homology arm can be sequenced with the "3'_pgtag_seq" primer: 5'-ATGGCTCATAACACCCCTTG-3' (SEQ ID NO:56).

G. Injection of GeneWeld Reagents (spCas9 mRNA, Universal sgRNA (UgRNA), Genomic sgRNA and pGTag Homology Vector) into 1-Cell Zebrafish Embryos (1) Prepare nCas9n mRNA from pT3TS-nCas9n (Addgene #46757 from Jao et al., supra) as described above.

(2) Synthesize UgRNA and purify as described above using oligo A: 5'-TAATACGACTCACTATAGG-GAGGCGTTCGGGCCACAGGTTTT AGAGCTAGAAATAGC-3' (SEQ ID NO:57)

Corresponding to the universal target sequence: GGGAGGCGTTCGGGCCA CAG (SEQ ID NO:58)

Alternatively, the UgRNA can be commercially obtained (e.g., from IDT) and resuspended in RNF water.

5'-GGGAGGCGUUCGGGCCACAGGUUUUAGAGCUAGAAAUAGCAAGU UAAAAUAAGGCUAGUCCGUUAUCAACUUGAAAAAGUGGCACCGAGU CGGUGCGGAUC-3' (SEQ ID NO: 59)

(3) The pGTag homology vectors can be purified a second time prior to microinjection under RNase free conditions with the Promega Pure Yield Plasmid Miniprep System beginning at the endotoxin removal wash and eluted in RNF water.

Embryo Injections for Integration of pGTag Vectors

Injections are performed as described above, in 2 nl per embryo with the addition of the UgRNA and targeting pGTag DNA.

| Final per embryo: | Injection mixture: |
|---|---|
| 150 pg of nCas9n mRNA | 75 pg/nl of nCas9n mRNA |
| 25 pg of genomic gRNA | 12.5 pg/nl of genomic gRNA |
| 25 pg of UgRNA | 12.5 pg/nl of UgRNA |
| 10 pg of pGTag DNA | 5 pg/nl of pGTag DNA |

H. Examine Embryos for Fluorescence and Junction Fragments

Embryos are examined for fluorescence under a Zeiss Discovery dissecting microscope with a 1× objective at 70-100× magnification. If weak signals are observed, embryos are manually dechorionated, and viewed on glass depression well slides. If no or weak signals were observed, Gal4VP16 integrations are attempted in a 14XUAS-RFP background. Embryos displaying widespread fluorescence in expression domains consistent with the targeted gene are examined for junction fragments or raised to adulthood for outcrossing.

F0 Junction fragment analysis between the genomic locus and the targeting vector is carried out by isolating DNA from embryos followed by PCR. The following primers are used for junction fragment analysis and must be paired with gene specific primers (5' to 3').

5' pGTag Junctions:

R-Gal4-5'juncM (SEQ ID NO: 60)
GCCTTGATTCCACTTCTGTCA with a gene specific forward primer R-RFP-5'junc (SEQ ID NO: 61)
CCTTAATCAGTTCCTCGCCCTTAGA R-eGFP-5'-junc (SEQ ID NO: 62)
GCTGAACTTGTGGCCGTTTA 3' pGTag Junctions:

F-Gal4-3'juncM (SEQ ID NO: 63)
GCAAACGGCCTTAACTTTCC with a gene specific reverse primer F-Gal4-3'juncJ (SEQ ID NO: 64)
CTACGGCGCTCTGGATATGT F-RFP-3'junc (SEQ ID NO: 65)
CGACCTCCCTAGCAAACTGGGG F-eGFP-3'junc (SEQ ID NO: 66)
ACATGGTCCTGCTGGAGTTC PCR amplification of junction fragments can be a result of artifacts (Won and Dawid, *PLoS One,* 12 (3): e0172802, 2017), so it is important to carryout control amplifications with injected embryos that lack the genomic gRNA. F0 analysis by PCR of junction fragments is carried out to examine correct targeting. F-Gal4-3'juncM and F-Gal4-

3'juncJ are two alternate primers for amplification of junction fragments from the Gal4 cassette due to gene specific mis-priming depending on the target loci.

7.5 µL 2× Gotaq mastermix
5.5 µL dH$_2$O
0.5 µL primer at 10 µM genomic primer
0.5 µL primer at 10 µM pGTag primer
14 µL total (1) Aliquot 14 µL of mixed master mix into separate labeled PCR tubes.
(2) Add 1 µL of genomic DNA to each reaction as template.
(3) Cycle in a thermocycler with the following steps:

| | | |
|---|---|---|
| 95° C. | 2 minutes | |
| 95° C. | 30 seconds | |
| 55° C. | 30 seconds | × 35 cycles |
| 72° C. | 30 seconds | |
| 72° C. | 5 minutes | |
| 4° C. | hold | |

(4) Run 5 µL of PCR product on a 1.2% agarose gel in 1×TAE. Putative junction fragments should give bands that are of predicted size.

F0 animals that are positive for the reporter gene are raised to adults then outcrossed and examined for fluorescence as above. The Gal4VP16 system can lead to silencing, resulting in mosaic patterns in F1 embryos. F1 embryos displaying fluorescence are examined for junction fragments as above, raised to outcross to make F2 families or sacrificed at 3 weeks post fertilization for Southern-Blot analysis of integrations. F0 and F1 identified fish can be incrossed or backcrossed to get an initial impression of the homozygous phenotypes. It is recommended that lines are continuously outcrossed once established.

Example 3—Efficient Targeted Integration Directed by Short Homology

A suite of targeting vectors, called pGTag (FIG. 4A), was engineered to provide homologous ends for gene targeting with the CRISPR/Cas9 system and a web interface for designing homology arms (genesculpt.org/gtaghd/). The pGTag vectors take advantage of two simultaneous actions to initiate targeted repair (FIGS. 1A and 1B). First, a highly efficient targeted nuclease introduces a double-strand break in the chromosomal target. Simultaneously, a second and parallel nuclease releases the integration cassette to expose the short homology ends. The complementarity between the chromosomal double-strand break and the arms activates a single strand annealing or other non-NHEJ DNA repair mechanism, referred to as homology-mediated end joining (HMEJ). The reagents needed for this gene targeting strategy are referred to herein as GeneWeld and include a genomic double strand break editor, a guide RNA that directs cuts near the short homology to expose the homologous DNA ends, Cas9, and the short homology containing donor plasmid (FIG. 4B). The results presented below demonstrate the use of GeneWeld reagents widespread reporter gene expression in injected F0 zebrafish and targeted integration into zebrafish embryos (FIGS. 8A-8E), indicating efficient and precise in-frame integration in multiple species and cell systems.

Figure 5A:
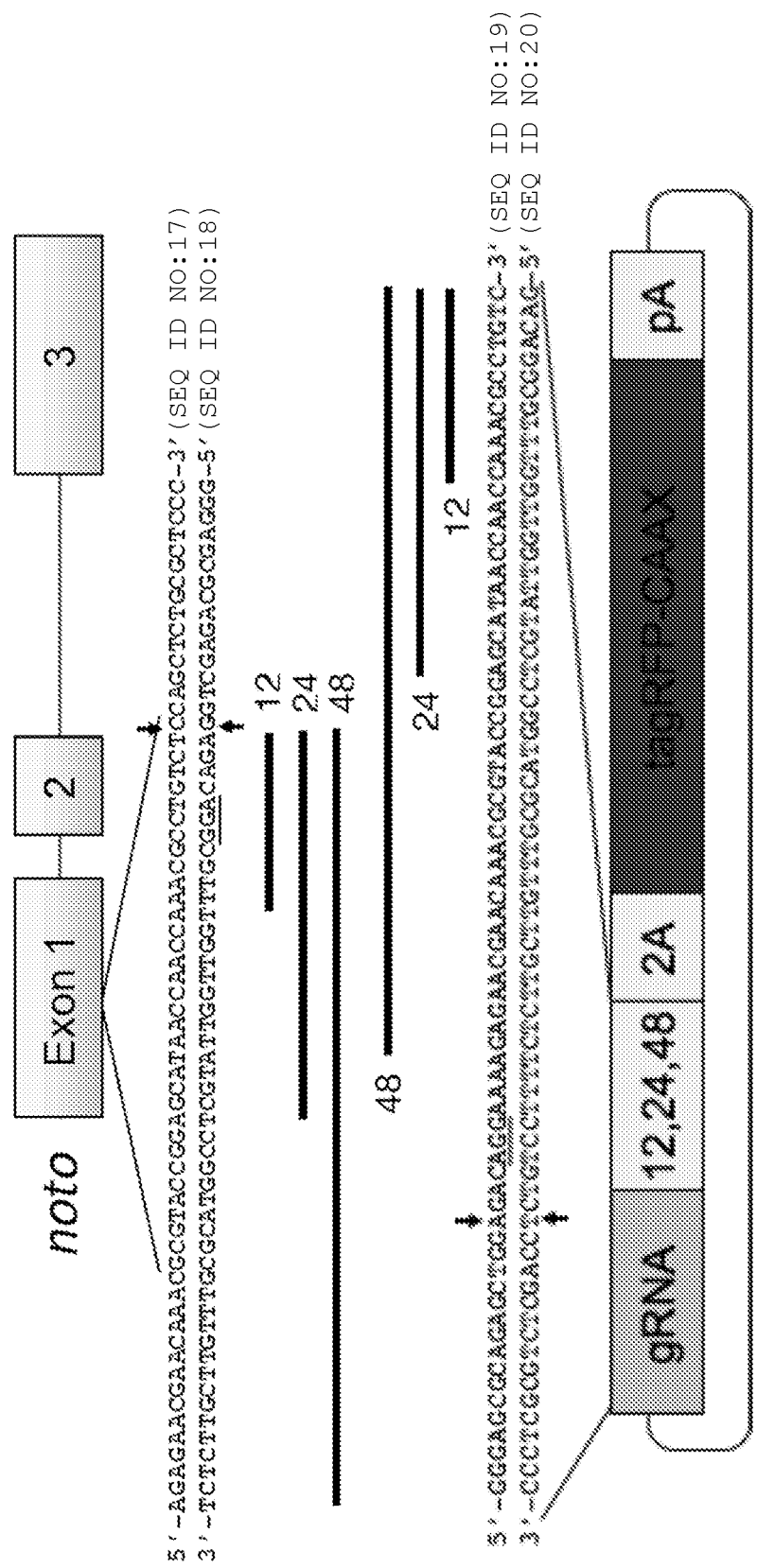
Figure 5B:
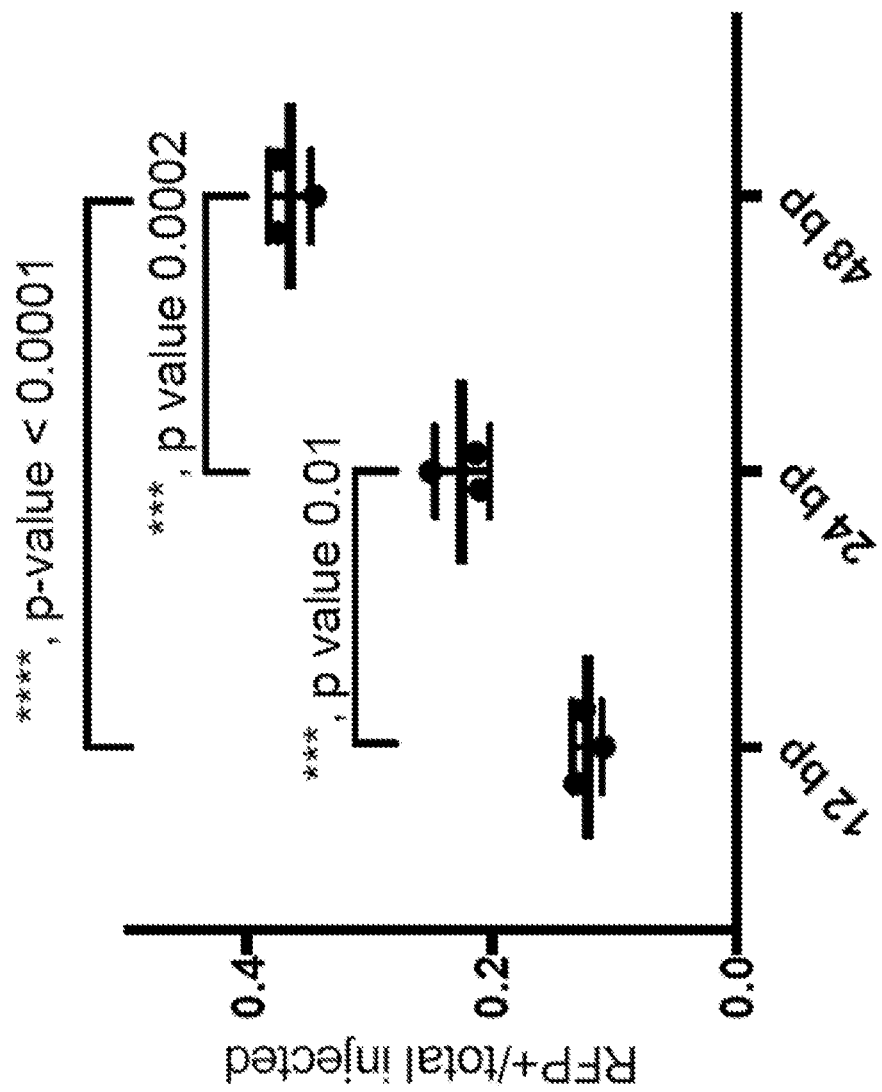
Figure 5C:
Figure 6A:
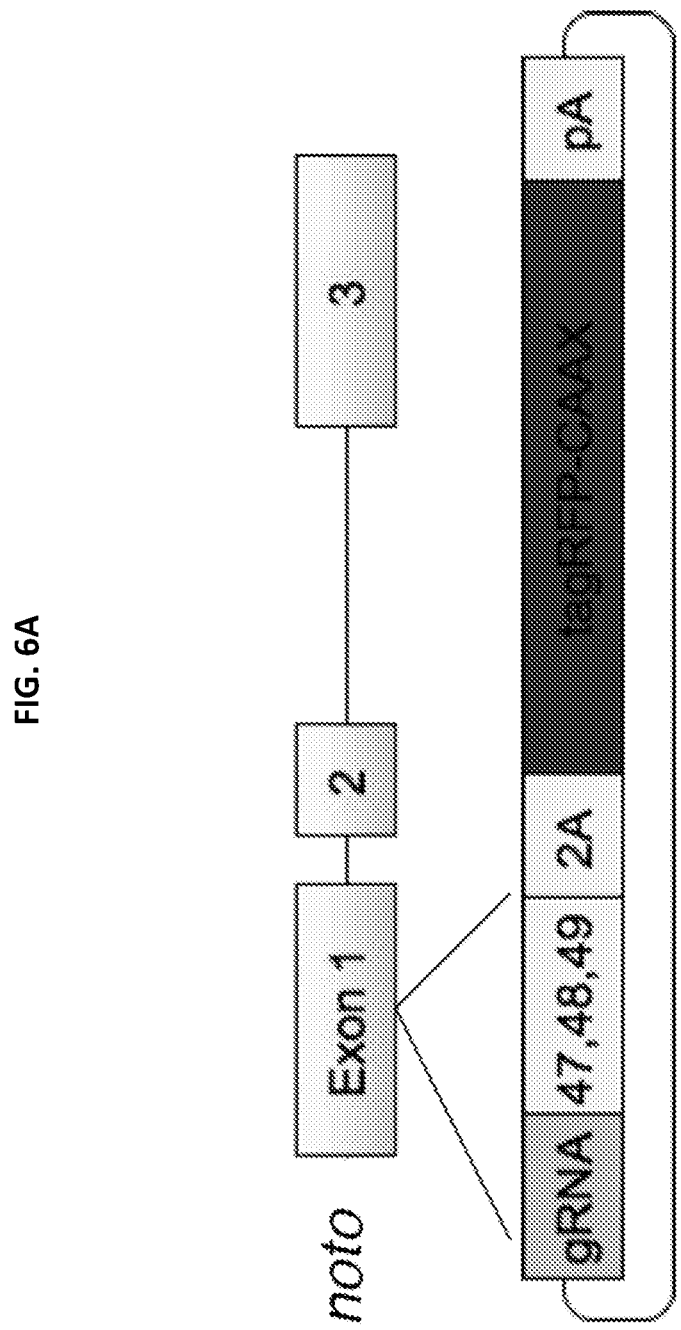
FIGS. 6A and 6B show that single base pair differences in homology arm length 5' to the Cas9/gRNA cut site can influence integration frequencies in zebrafish embryos.
Figure 6B:
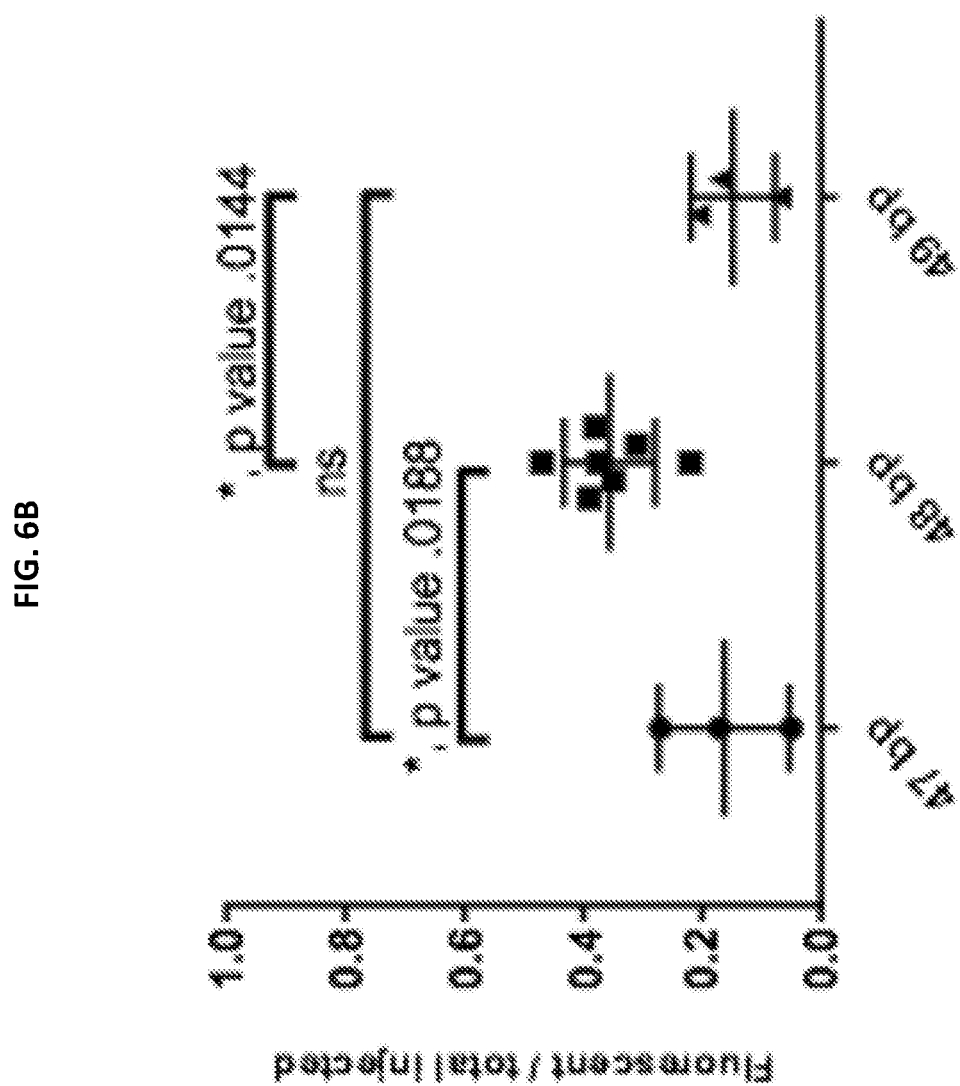
Figures 7A, 7B:
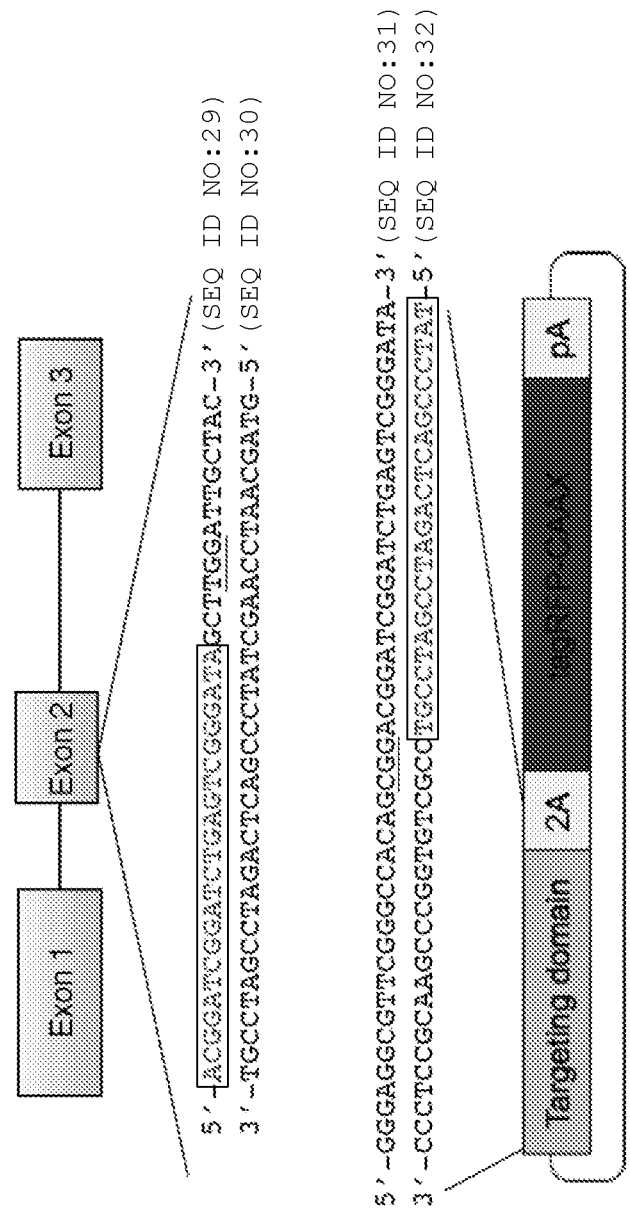
FIGS. 7A-7C show that the Universal gRNA (UgRNA) promotes high efficiency targeted integration.
Figure 7C:
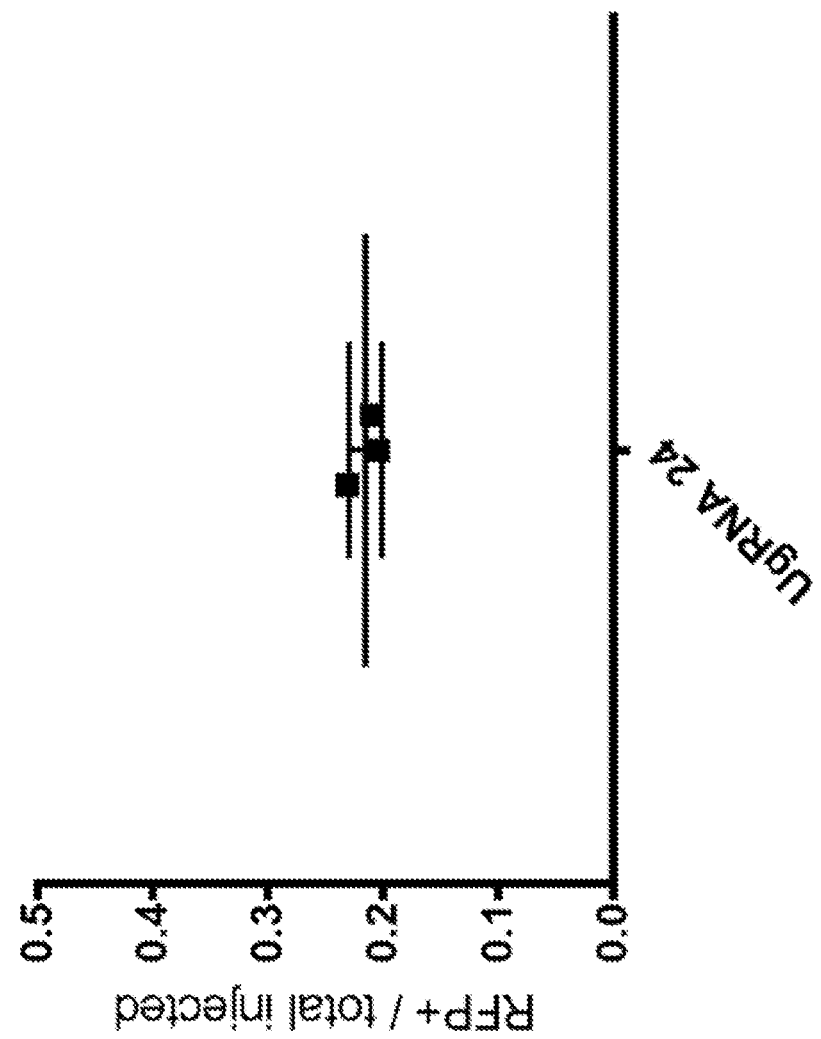

To develop baseline gene targeting data, variable length homology domains were engineered to target noto based on observations that DNA repair enzymes bind DNA and search for homology in 3 or 4 base pair lengths (FIG. 5A) (Conway et al., Nat Struct Mol Biol, 11 (8): 791-796, 2004; and Singleton et al., Proc Natl Acad Sci USA, 99 (21): 13492-13497, 2002). Upon injection of a noto sgRNA to target both the genome and one homology domain of a 2A-TagRFP-CAAX-SV40 donor vector, efficient integration was observed as notochord specific RFP (FIGS. 5B and 5C, and TABLES 2A and 2B). The frequency of RFP expression increased as the homology domain was increased to 48 bp (FIG. 5B), but 192 bp of homology displayed reduced integration activity (not shown). Somatic junction fragment analysis showed precise integration efficiencies reaching 95% of sequenced alleles (FIG. 5D). Following these initial experiments, a 3 bp spacer sequence was included in all arm designs to separate the donor CRISPR/Cas9 target PAM and the homology domain to not arbitrarily increase targeting domain length, as single base pair alterations in the homology region can affect knock-in efficiency up to 2-fold (FIGS. 6A and 6B). To streamline donor design and liberate donor cargo in vivo with repeatable efficiency, a universal gRNA (UgRNA) sequence, with no predicted targets in zebrafish, pig, or human cells, was designed based on optimal base composition (FIG. 7A) (Moreno-Mateos, et al., supra) and cloned adjacent to the homology in the targeting vector. Experiments targeting noto with the UgRNA resulted in RFP expression in the notochord in 21% of injected embryos, indicating correct targeting of noto and demonstrating the efficacy of Cas9/UgRNA to expose the single 5' homology arm in the targeting construct for driving precise integration (FIGS. 7A and 7B). The high frequency of RFP+ cells following injection of GeneWeld reagents suggested that repair of the double strand break preferentially utilizes the homology in the targeting construct over the NHEJ pathway.

Figure 4A:
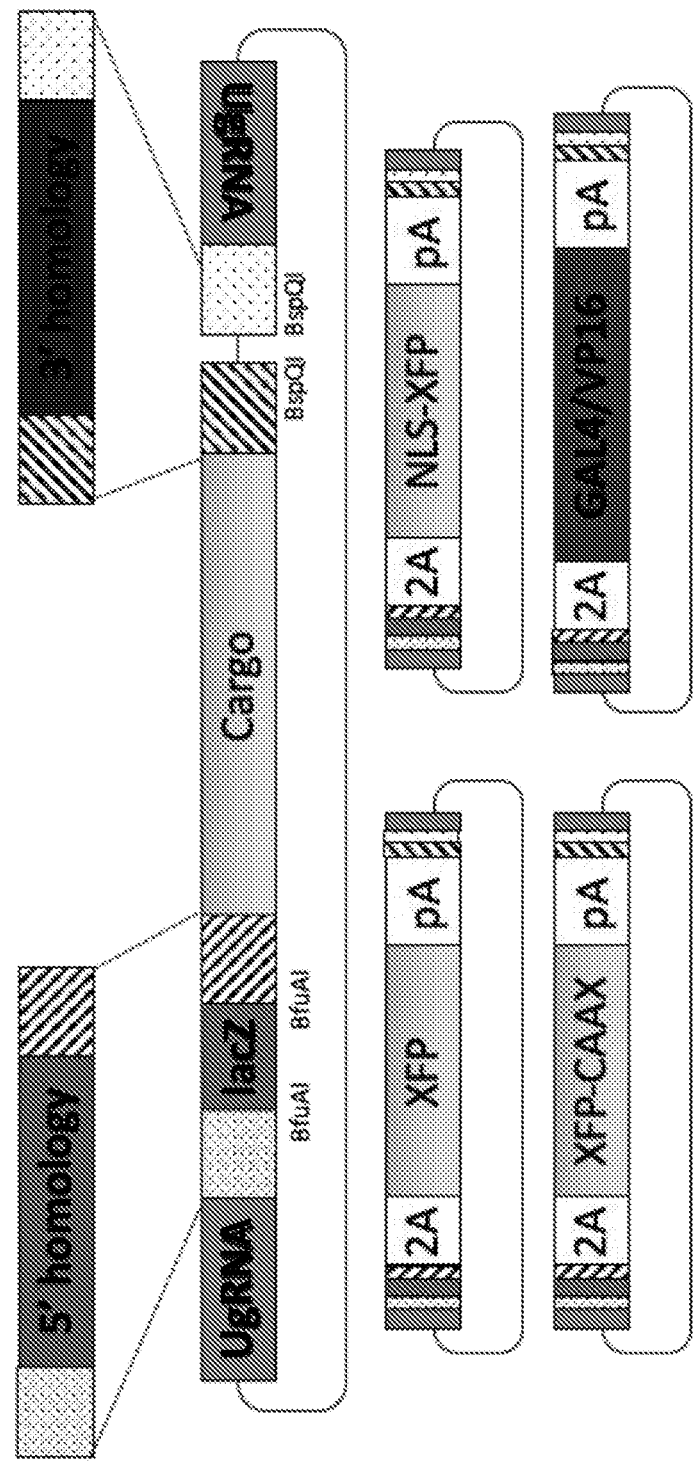
FIGS. 4A and 4B are diagrams depicting the pGTag vector series and the GeneWeld gene targeting reagents.
Figure 4B:
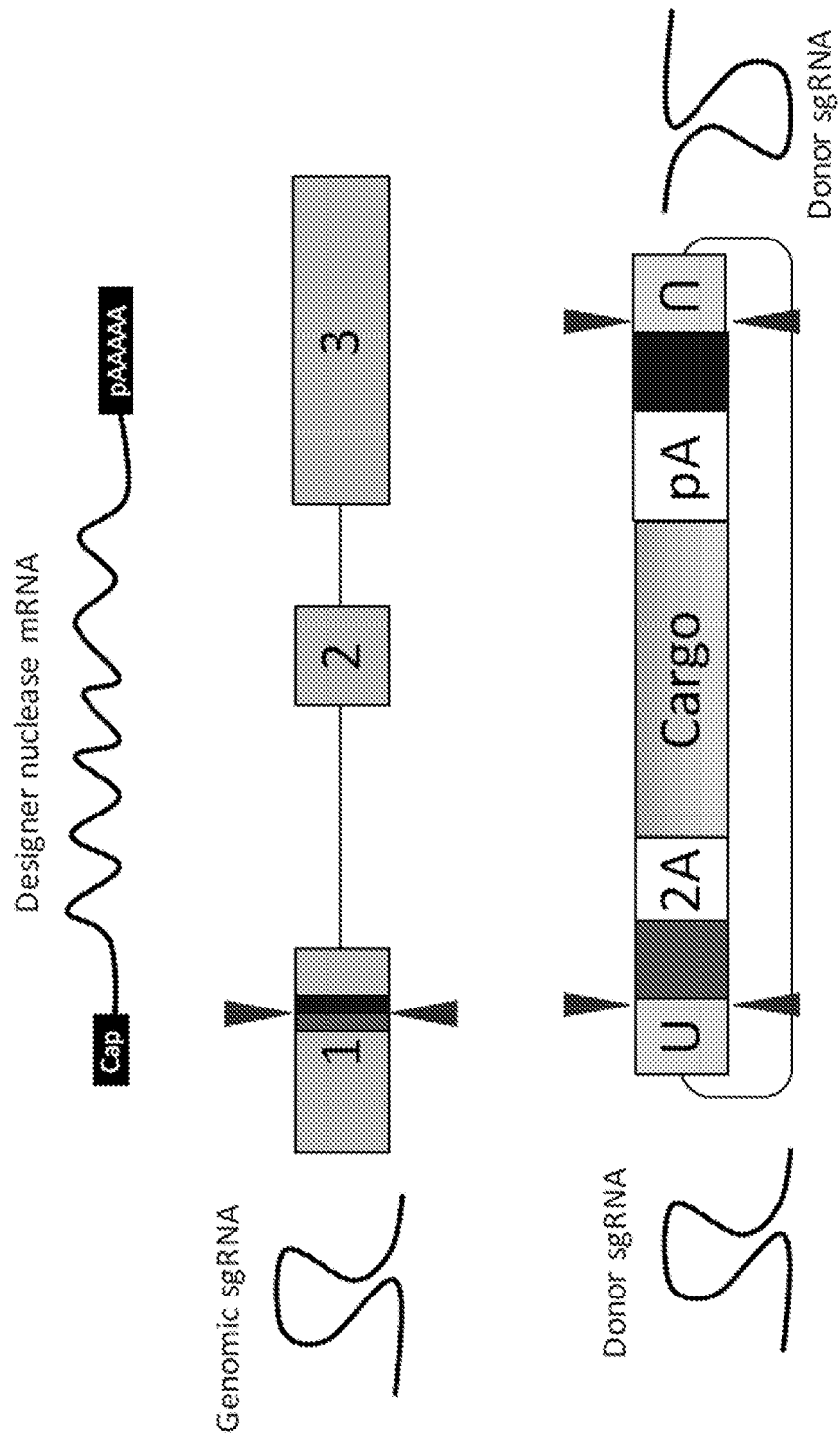

The activity of the UgRNA was leveraged in the design of the pGTag series of Golden Gate cloning compatible targeting vectors, by including UgRNA target sites on both sides of the cargo (FIG. 4A). Cleavage by Cas9 at the UgRNA sites liberates the DNA cargo from the backbone and exposes both 5' and 3' short homology domains for interaction with DNA on either side of the genomic double strand break (FIG. 1B). Injection of GeneWeld reagents containing either 2A-TagRFP-CAAX-SV40 or 2A-eGFP-SV40 donors targeting noto resulted in 24% of embryos showing extensive notochord expression of the reporter, indicating a similar targeting efficiency compared to targeting with 5' homology alone (FIGS. 5A-5D, 8A, and 8B). Two out of five (40%) 2A-TagRFP-CAAX-SV40 injected founder fish raised to adulthood transmitted noto-2A-TagRFP-CAAX-SV40 tagged alleles through the germline (TABLES 3 and 4). Genomic Southern blot analysis of four F1s from each founder confirmed a single copy integration of 2A-TagRFP-CAAX-SV40 in noto exon 1 (FIGS. 9A-9D). Progeny from the first founder had precise integrations at the 5' end of the target site but contained an ~400 bp deletion downstream extending into exon 2. The second founder produced offspring with a precise 5' integration allele but also included insertion of a segment of the vector backbone at the 3' end. Sequencing of junction fragments from the first founder confirmed that NHEJ drove integration at the 3' end rather than a homology-based mechanism (FIG. 9D). Together, these results indicate that GeneWeld reagents can promote precise single copy integration at a genomic cut site without vector sequences, although events involving NHEJ at the at the 3' end are also recovered.

To extend these results to other loci in zebrafish, cx43.4, tyr, and esama were targeted with 2A-TagRFP-CAAX-SV40 and varying homologies (FIGS. 8A and 8C-8E; TABLE 1).

Figure 8A:
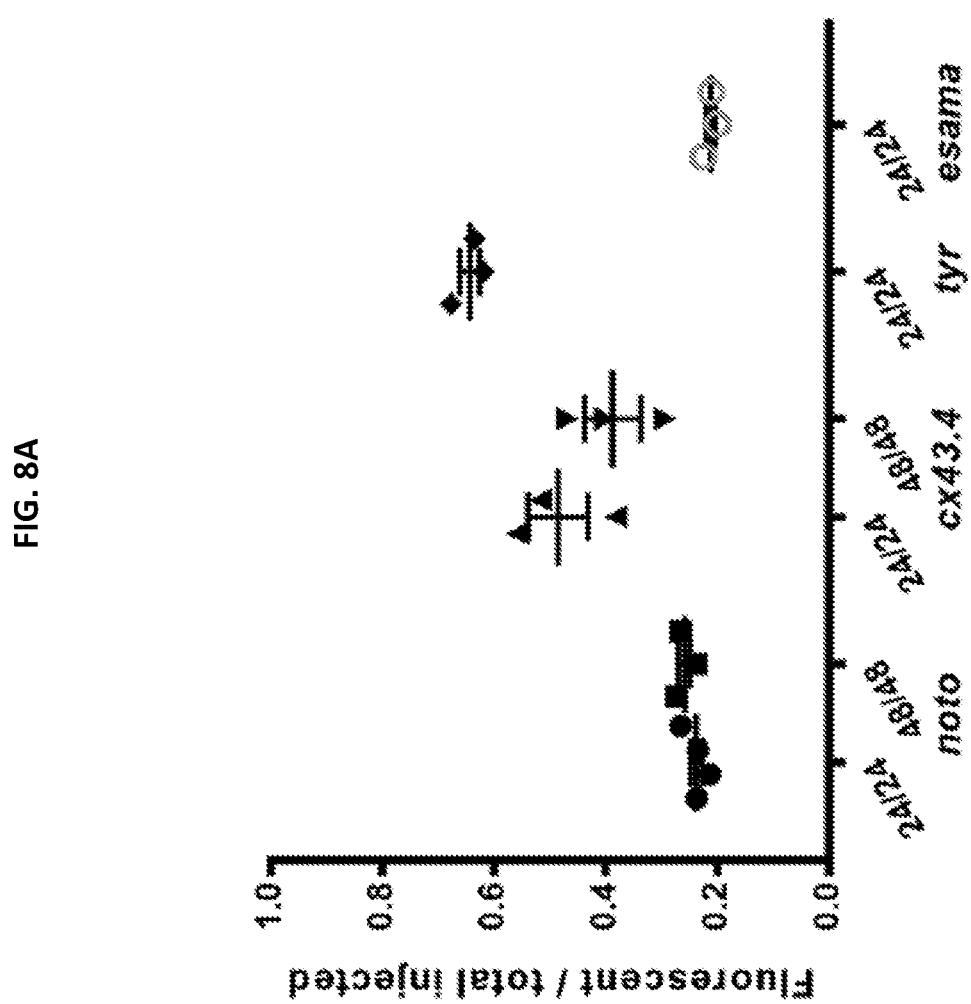
Figure 9A:
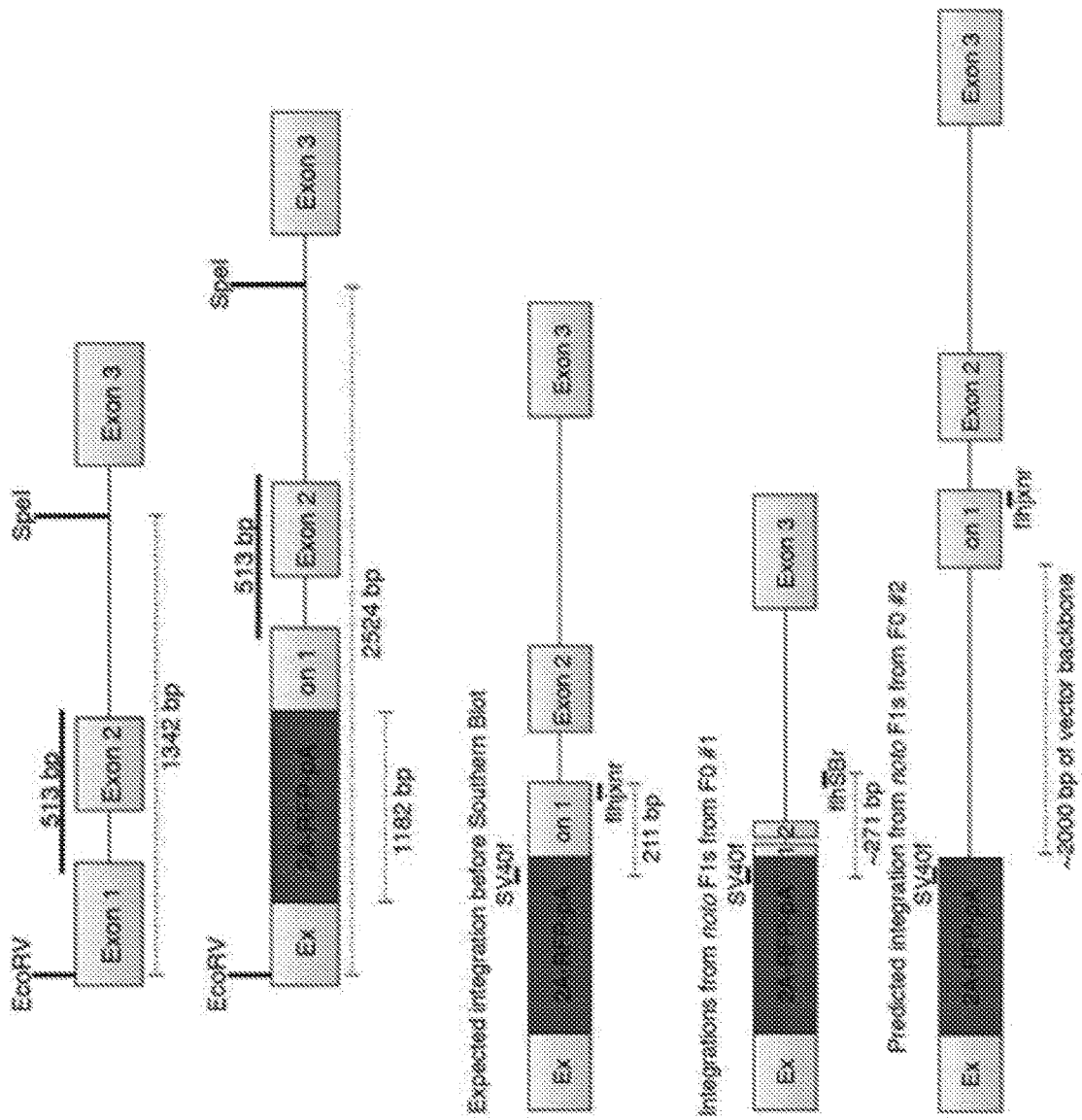
Figure 9B:
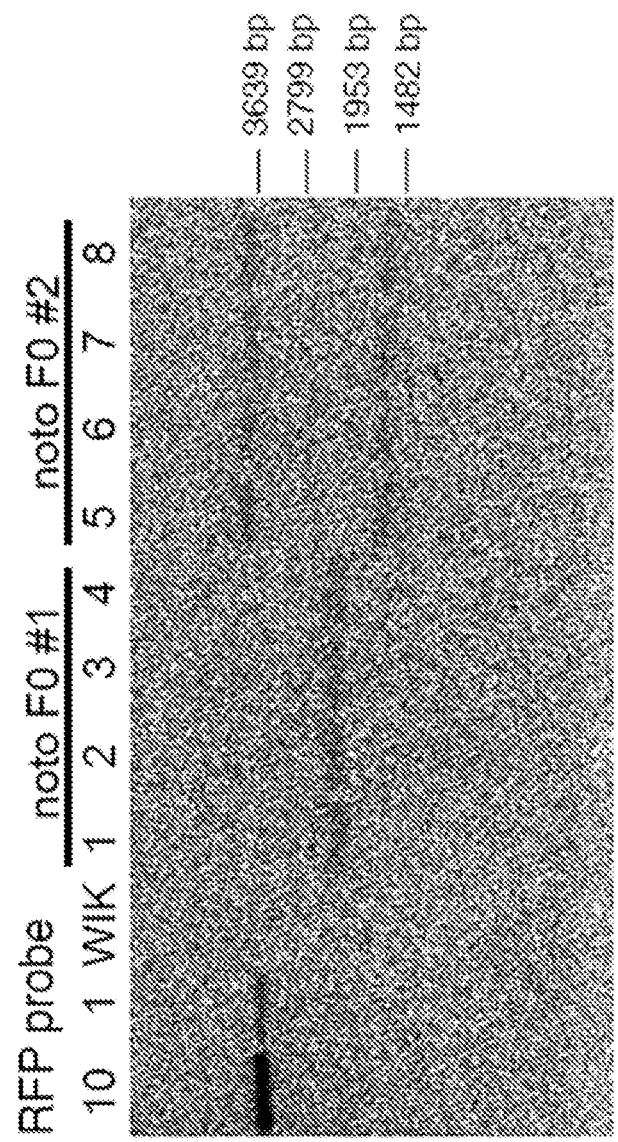
Figure 9C:
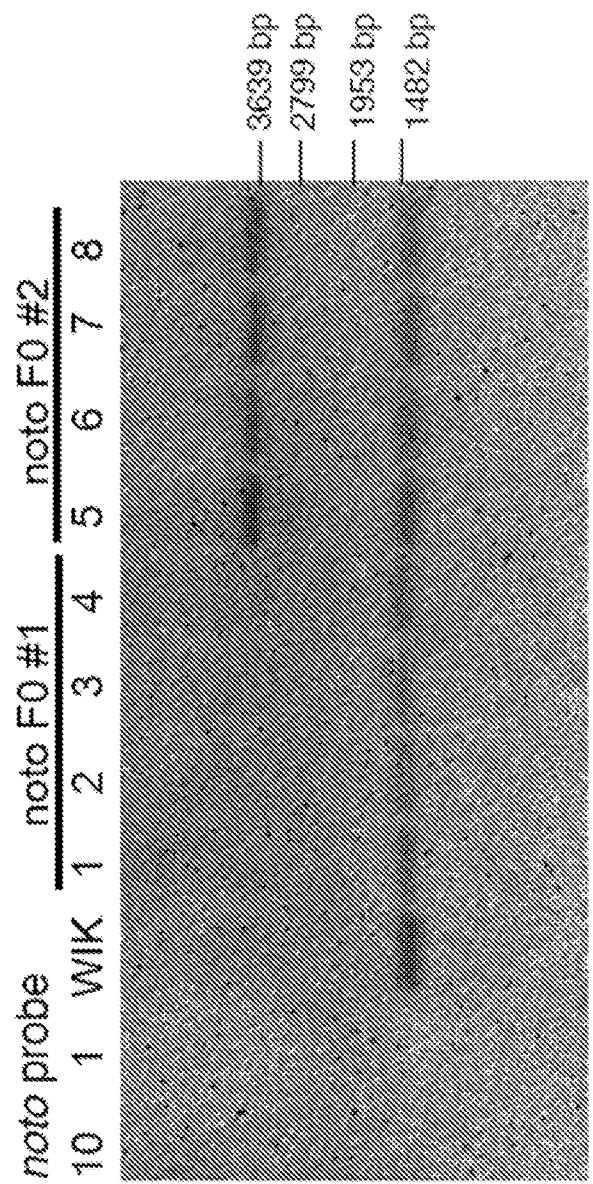
Figure 10B:
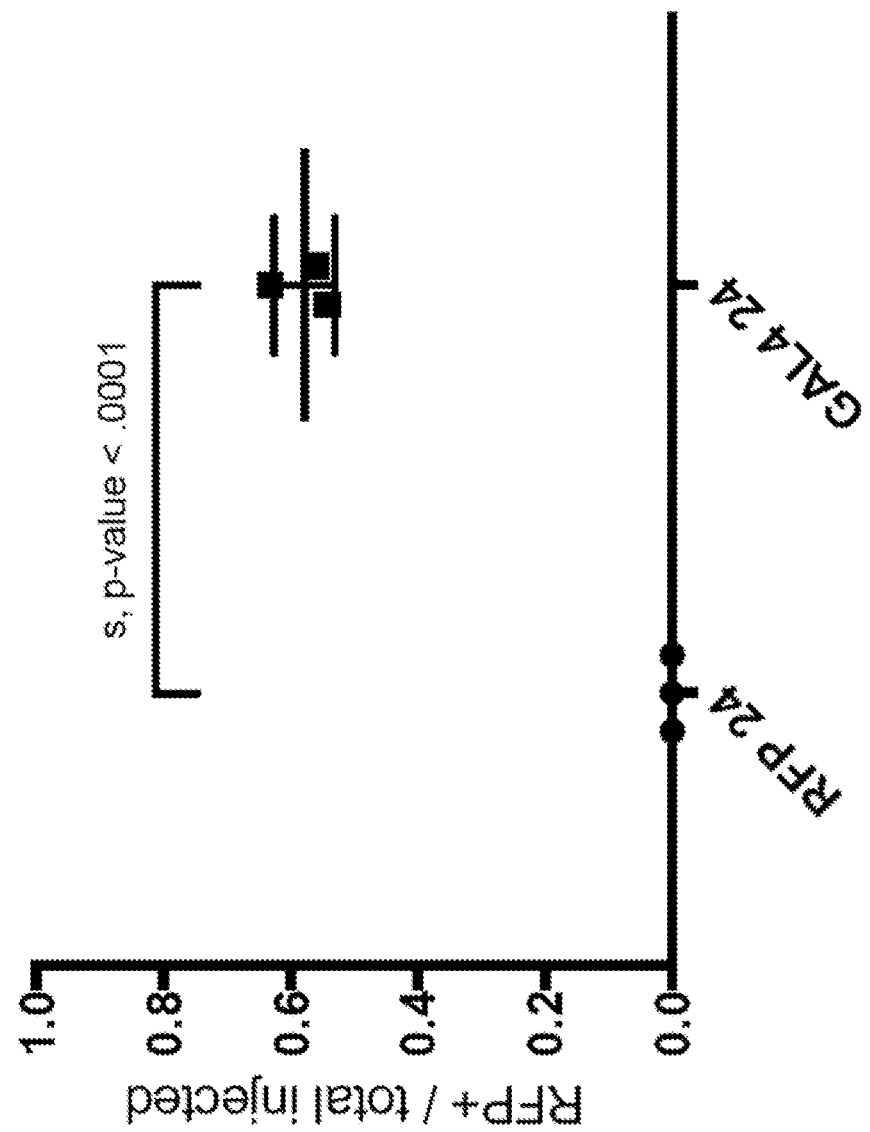
Figure 11A:
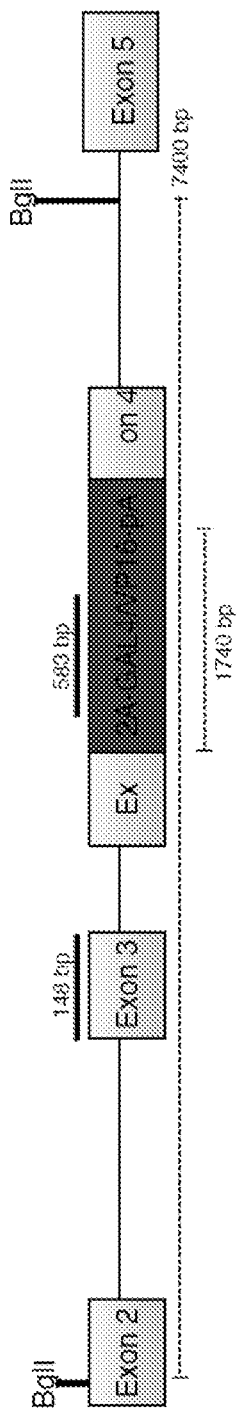
Figure 11B:
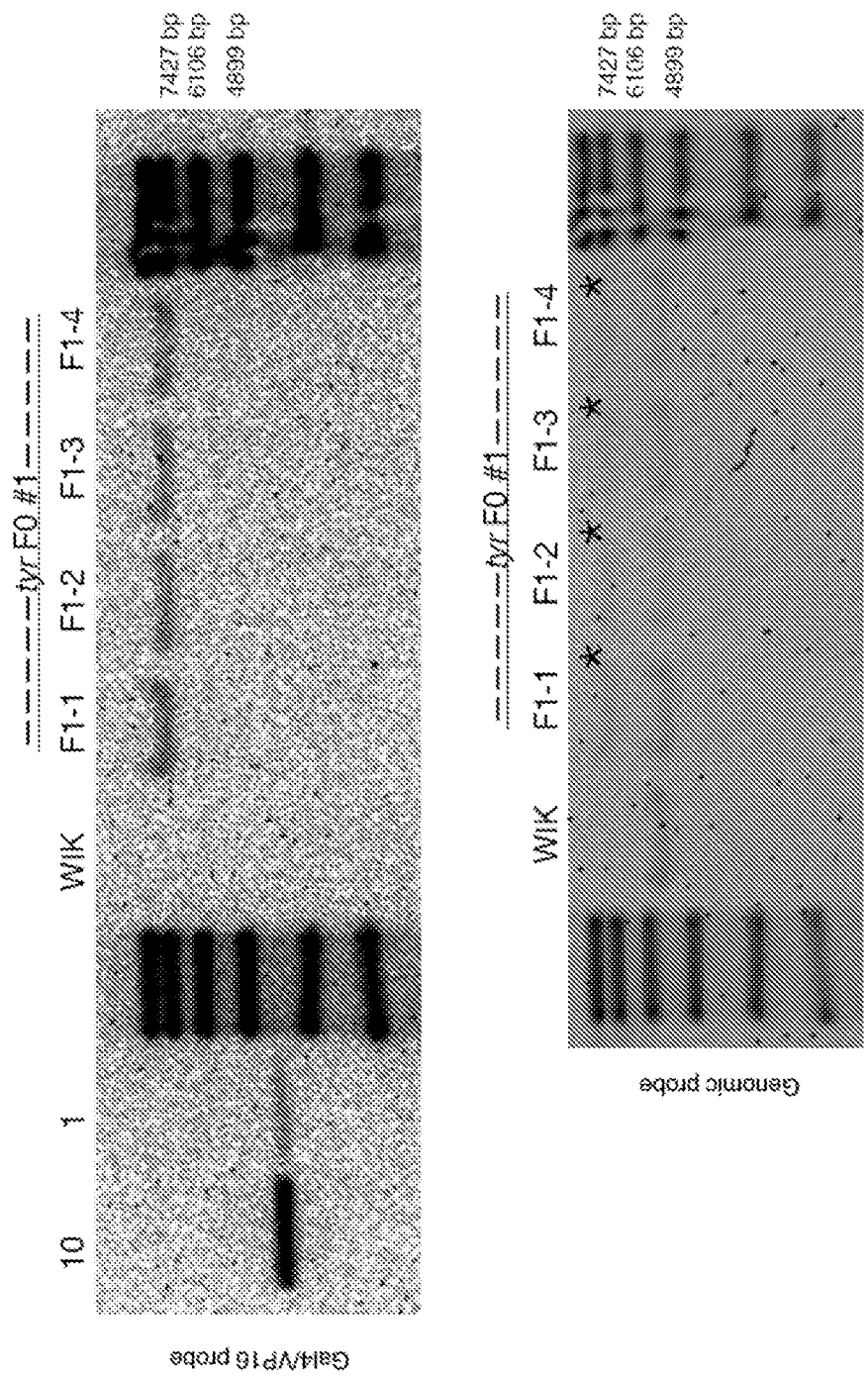
Figure 12A:
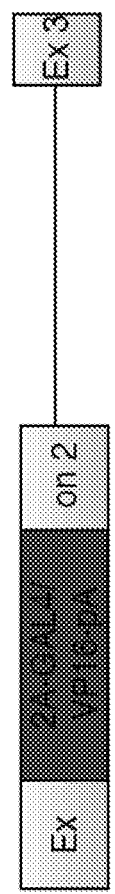

GeneWeld reagents targeting cx43.4 resulted in broad RFP expression throughout the nervous system and vasculature in 29% to 56% of the injected embryos (FIGS. 8A and 8C). GeneWeld reagents targeting exon 4 of tyrosinase (tyr) did not result in detectable RFP signal, similar to reports published elsewhere (Hisano et al., Sci Rep, 5:8841, 2015). However, PCR junction fragments from injected larvae showed the donor was precisely integrated in frame into tyr exon 4 (FIGS. 10 and 10B), suggesting RFP expression was below the threshold of detection. To amplify the fluorescent signal, pGTag-2A-Gal4VP16-bactin was used to integrate the transactivator Gal4VP16 at the tyr exon 4 target site in transgenic embryos carrying a 14×UAS-RFP reporter, called Tg(UAS:mRFP)$^{tpl2}$ (Balciuniene et al., supra). This resulted in a strong RFP signal in 64% of injected animals, but the embryos were highly mosaic compared to targeting 2A-TagRFP-CAAX-SV40 into noto and cx43.4, with only 9% of RFP embryos displaying extensive expression in pigmented cells (FIGS. 8A and 8D). Seven embryos with moderate to broad expression in the retinal pigmented epithelia were raised to adulthood and outcrossed. Of those, one transmitted tagged alleles to the next generation (14%; TABLE 4). Southern blot analysis and sequencing of tyr-2A-Gal4VP16 F1 progeny demonstrated a single copy integration of the Gal4VP16 cassette with precise integration at both 5' and 3' ends (FIGS. 11A-11C). Similar to tyr, GeneWeld reagents targeting 2A-TagRFP-SV40 into exon 2 of the esama gene did not result in detectable RFP expression. GeneWeld reagents targeting pGTag-2A-Gal4VP16 in the Tg(UAS:mRFP)$^{tpl2}$ transgenic background resulted in 21% of embryos displaying extensive RFP expression specifically in the vasculature (FIGS. 8A and 8E). Twelve FOs displaying widespread vasculature RFP expression were raised to adulthood and seven (58%) transmitted esama-2A-Gal4VP16-bactin alleles to the F1 generation with precise 5' and 3' junctions (FIGS. 12A and 12B). Taken together, these results indicated that GeneWeld reagents efficiently promote targeted integration in zebrafish, with many recovered alleles in the F1 generation having precise repair events at both the 5' and 3' sides of the target site.

Figure 13A:
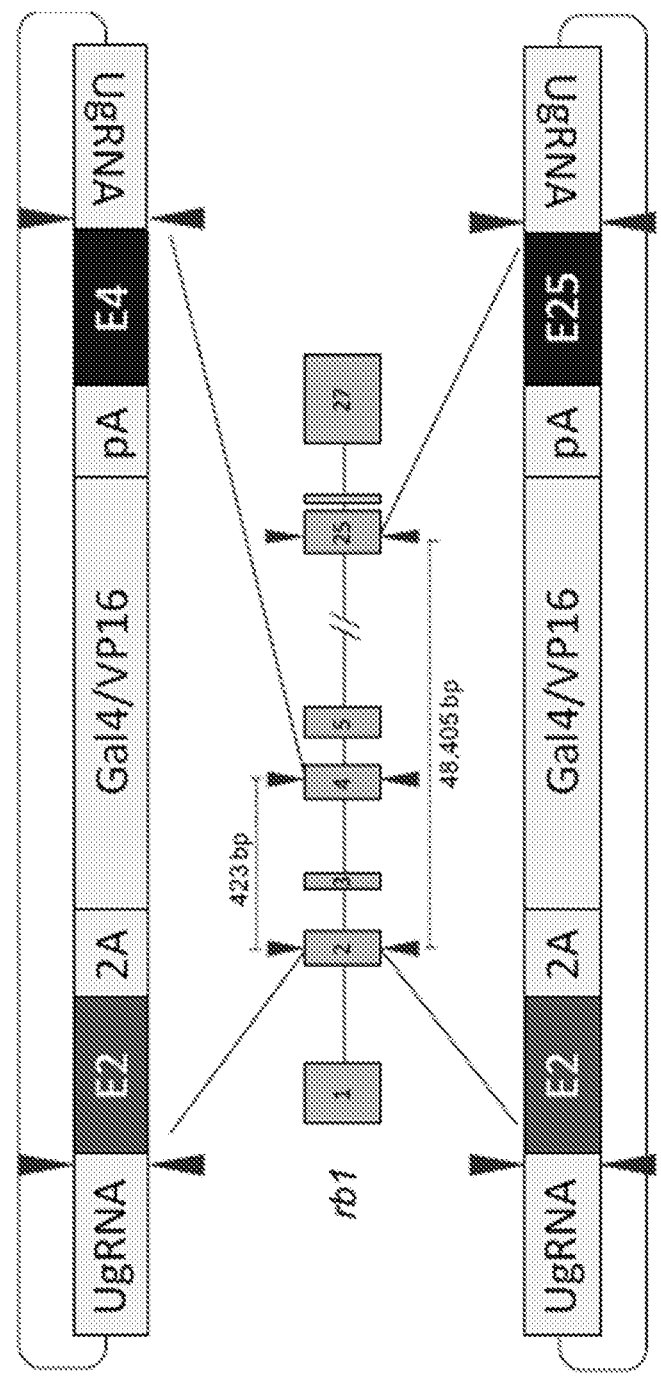
FIGS. 13A-13E show deletion tagged alleles created with the HMEJ strategy during zebrafish embryogenesis.
Figure 13B:
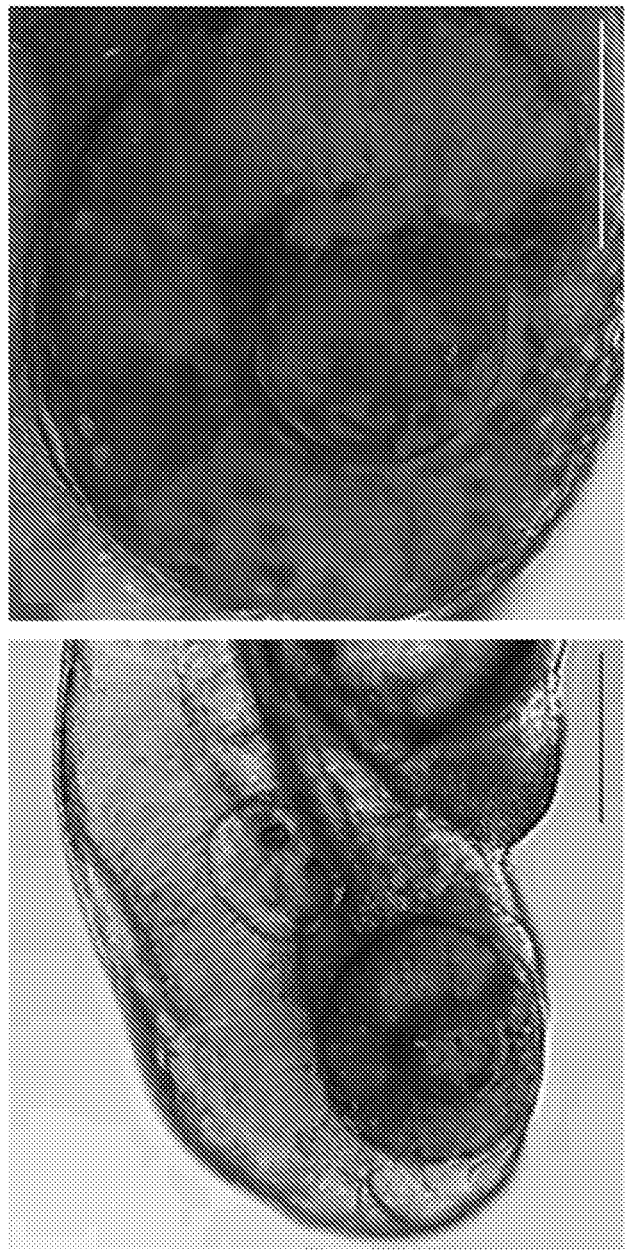
Figure 13C:
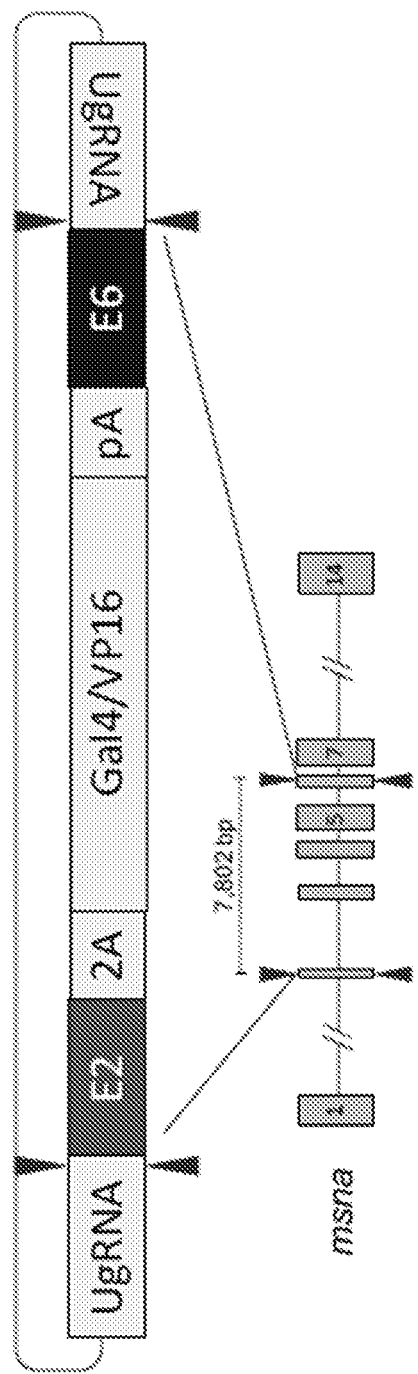
Figure 13D:
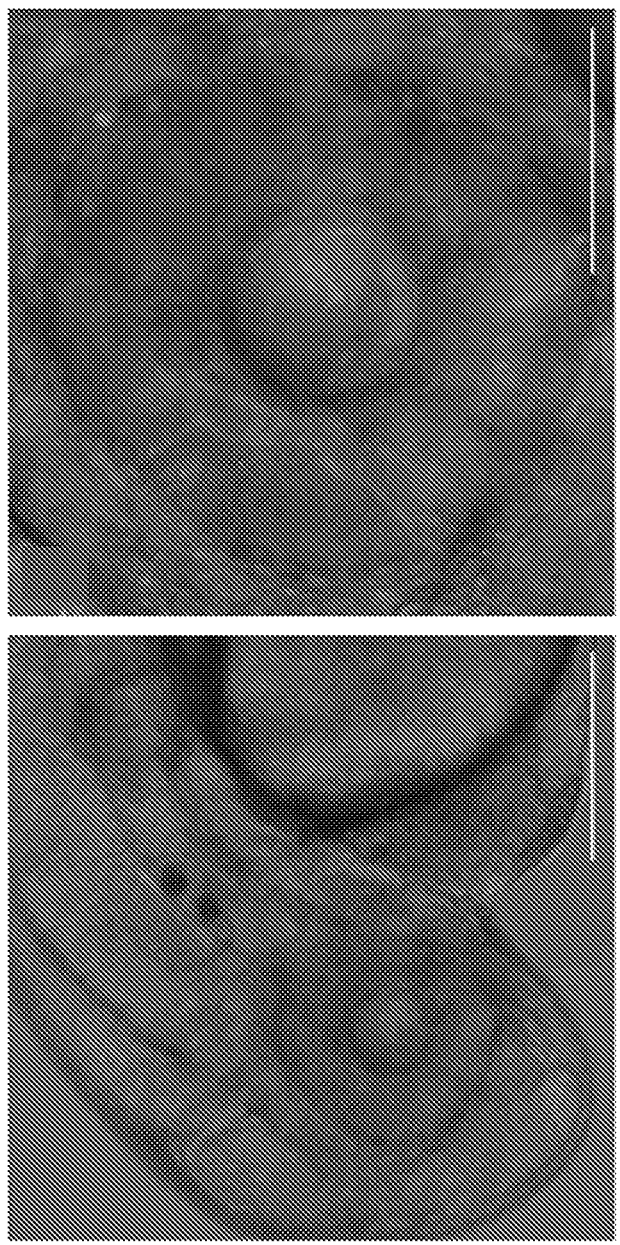
Figure 13E:
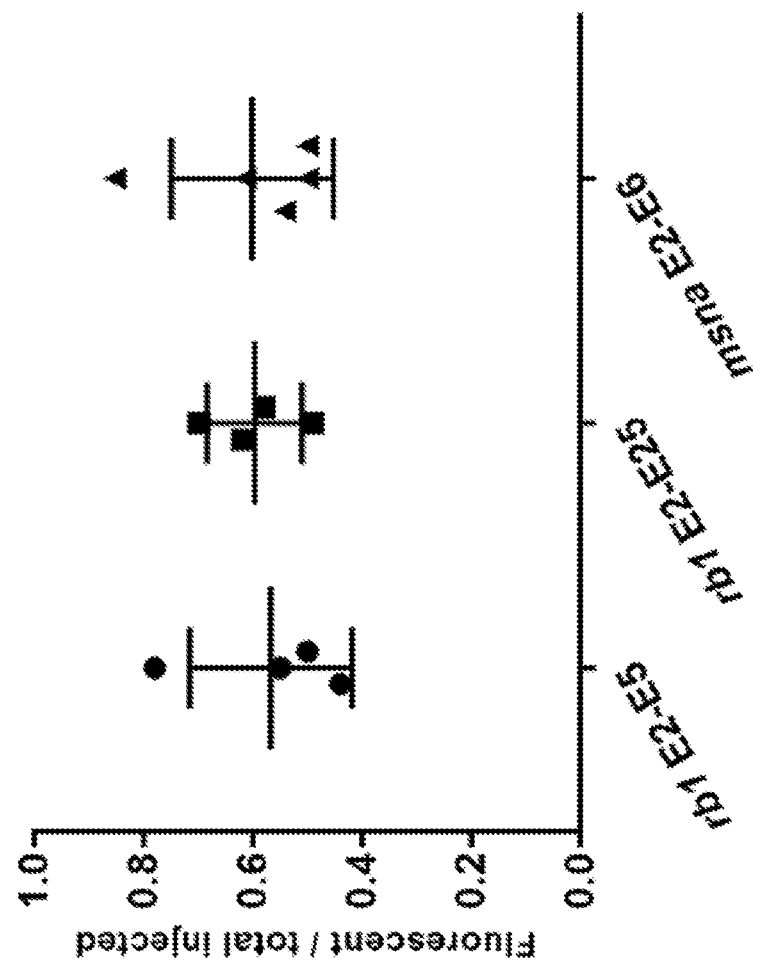
Figure 14A:
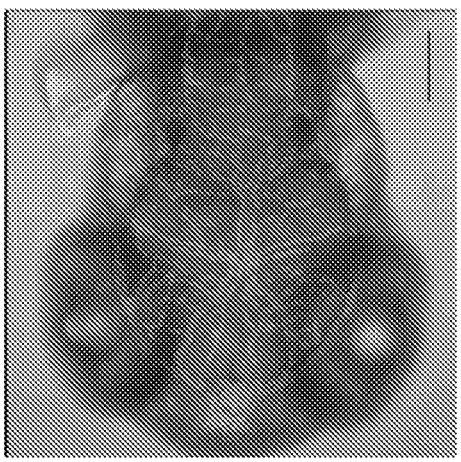
FIGS. 14A-14C are a series of live confocal images of F1 zebrafish with inherited germline alleles of integrated GTag reporters.
Figure 14A:
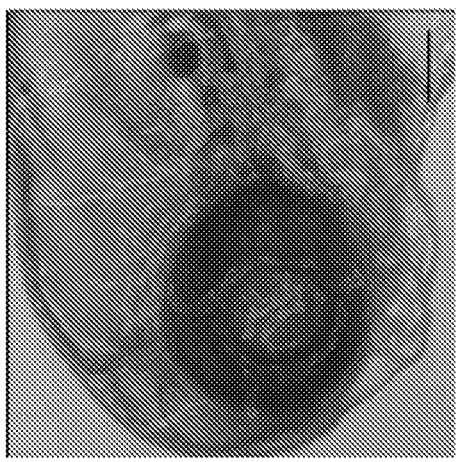
Figure 14B:
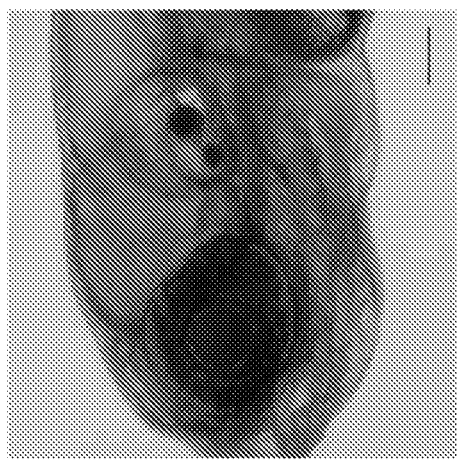
Figure 14B:
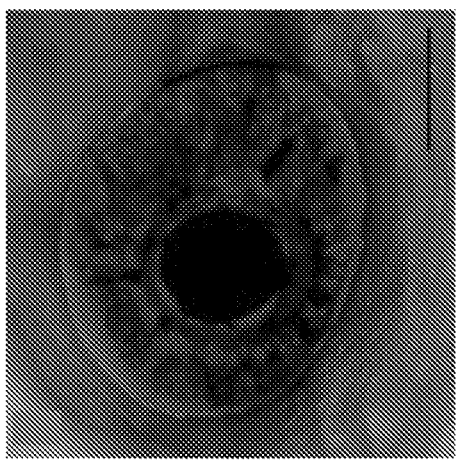
Figure 14C:
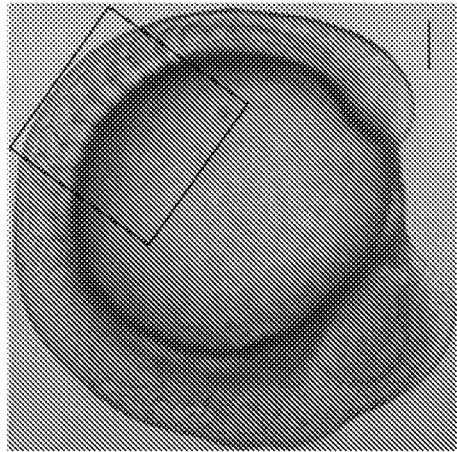
Figure 14C:
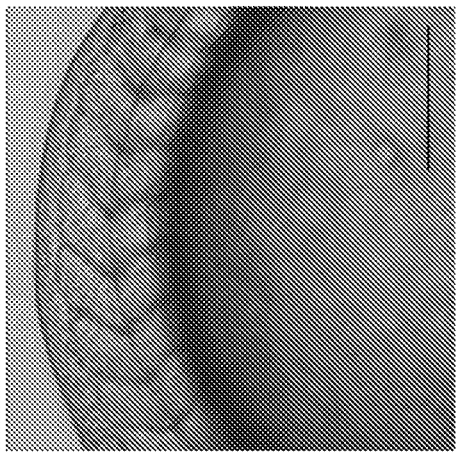

To further test the utility of GeneWeld reagents, studies were conducted to determine whether the pGTag donors could function to bridge two CRISPR/Cas9 genomic cuts, resulting in simultaneous deletion and integration to create a "deletion tagged" allele. The pGTag-2A-Gal4VP16 donor was programed to two gRNA target sites in retinoblastoma1 (rb1) gene exons 2 and 4 located 394 bp apart, or in exons 2 and 25 which are separated by ~48.4 kb (FIG. 13A). The 5' homology arm contained sequences upstream of the cut site in exon 2, while the 3' homology arm contained sequence downstream of the cut site in either exon 4 or exon 25. Injection of GeneWeld reagents with the corresponding exon 2-exon 4 or exon 2-exon 25 pGTag-2A-Gal4VP16-bactin donor into Tg(UAS:mRFP)$^{tpl2}$ embryos resulted in 59% and 60%, respectively, of injected embryos showing broad and ubiquitous RFP expression (FIG. 13B). Using the same approach to target moesina (msna) exons 2 and 6 with 2A-Gal4VP16-bactin resulted in 63% of the embryos displaying RFP in a pattern consistent with the expression of msna (FIGS. 13C and 13D). Somatic junction fragment analysis showed precise integration at both the 5' (85-100% of the fragments analyzed) and 3' ends (45-80%) of rb1 and msna (FIGS. 14A-14C). Taken together, these results demonstrate that simultaneous targeting of two distal genomic cut sites can create deletions that are efficiently replaced by insertion of a pGTag reporter cassette by HMEJ, and that increasing the size of the deleted region up to 48.4 kb did not affect the frequency of reporter integration.

These experiments greatly extend the utility of short homology-based gene targeting for precise integration of exogenous DNA, and expand the potential of efficient tagging to diverse loci with differing endogenous expression levels. The results also demonstrate that using short homology to bridge distal ends together simultaneously creates a deletion and a reporter integration, simplifying screening of deletion alleles. This strategy has additional applications to efficiently introduce other gene modifications, such as single or multiple nucleotide polymorphisms, by exon or gene replacement. The studies described herein demonstrated efficient integration of cargos up to 1.8 kb in length in zebrafish, and showed that both CRISPR/Cas9 and TALE nucleases can be effective genomic GeneWeld editors, providing flexibility in deployment and genome accessibility. This suite of targeting vectors with validated integration efficiencies, methods, and web interface for pGTag donor engineering can serve to streamline experimental design and broaden the use of designer nucleases for homology-based gene editing at CRISPR/Cas9 and TALE nuclease cut sites.

TABLE 1

Targeting domain information for GeneWeld experiments noto E1 target, 2A-TagRFP-CAAX-SV40 donor vector genomic target: GGGAGCGCAGAGCTGGAGACAGG (SEQ ID NO: 67)
donor target: GGGAGCGCAGAGCTGGAGACAGG (SEQ ID NO: 68)
5' spacer: aaa
1. 12 bp 5' homology (CAAACGCCTGTC; SEQ ID NO: 69)
3' spacer: N/A
3' homology: N/A
2. 24 bp 5' homology (AGCATAACCAACCAAACGCCTGTC; SEQ ID NO: 70)
3' spacer: N/A
3' homology: N/A
3. 48 bp 5' homology (AGAGAACGAACAAACGCGTACCGGAGCATAACCAACCAAACGCCTGTC (SEQ ID NO: 71)
3' spacer: N/A
3' homology: N/A noto E2 target, 2A-TagRFP-CAAX-SV40 donor vector genomic target: GACTGGAGAAAGAGTTCGCGCGG (SEQ ID NO: 72)
donor target: GACTGGAGAAAGAGTTCGCGCGG (SEQ ID NO: 73)
24 bp 5' homology (CTGTCCAGACTGGAGAAAGAGTTC; SEQ ID NO: 74)
3' spacer: N/A
3' homology: N/A
1. 5' spacer: aaa
2. 5' spacer: N/A noto E1 target, pGTag-2A-TagRFP-CAAX-SV40 donor vector genomic target: GGGAGCGCAGAGCTGGAGACAGG (SEQ ID NO: 67)
donor target: GGGAGGCGTTCGGGCCACAGCGG (SEQ ID NO: 75)
5' spacer: aaa
24 bp 5' homology (AGCATAACCAACCAAACGCCTGTC; SEQ ID NO: 70)
3' spacer: N/A
24 bp 3' homology (TCCAGCTCTGCGCTCCCGCTTATT; SEQ ID NO: 76)

TABLE 1-continued

Targeting domain information for GeneWeld experiments noto E1 target, pGTag-2A-eGFP-SV40 donor vector genomic target: GGGAGCGCAGAGCTGGAGACAGG (SEQ ID NO: 67)
donor target: GGGAGGCGTTCGGGCCACAGCGG (SEQ ID NO: 75)
5' spacer: aaa
48 bp 5' homology (AGAGAACGAACAAACGCGTACCGGAGCATAACCAACCAAACGCCTGTC; SEQ ID NO: 71)
3' spacer: ggg
48 bp 3' homology (TCCAGCTCTGCGCTCCCGCTTATTTACTCGCAGATGCCACACTTCGCG; SEQ ID NO: 77)

noto E1 target, 2A-TagRFP-CAAX-SV40 donor vector genomic target: GGGAGCGCAGAGCTGGAGACAGG (SEQ ID NO: 67)
donor target: GGGAGCGCAGAGCTGGAGACAGG (SEQ ID NO: 68)
5' spacer: N/A
3' spacer: N/A
3' homology: N/A
1. 47 bp 5' homology (GAGAACGAACAAACGCGTACCGGAGCATAACCAACCAAACGCCTGTC; SEQ ID NO: 78)
2. 48 bp 5' homology (AGAGAACGAACAAACGCGTACCGGAGCATAACCAACCAAACGCCTGTC; SEQ ID NO: 71)
3. 49 bp 5' homology (GAGAGAACGAACAAACGCGTACCGGAGCATAACCAACCAAACGCCTGTC; SEQ ID NO: 79)

cx43.4 E2 target, pGTag-2A-TagRFP-CAAX-SV40 donor vector genomic target: GAGCCATATCTTGCCCACGAAGG (SEQ ID NO: 80)
donor target: GGGAGGCGTTCGGGCCACAGCGG (SEQ ID NO: 75)
5' spacer: ccc
1. 24 bp 5' homology (AAATCTCCAACCACTCCACCTTCG; SEQ ID NO: 81)
3' spacer: ggg
24 bp 3' homology (TGGGCAAGATATGGCTCACGTTAT; SEQ ID NO: 82)
2. 48 bp 5' homology (GTTTTCTTACGCGGTTGTTGGATGAAATCTCCAACCACTCCACCTTCG; SEQ ID NO: 83)
3' spacer: aaa
48 bp 3' homology (TGGGCAAGATATGGCTCACGTTATTCATCATCTTCCGCATTGTTTTGA; SEQ ID NO: 84)

tyr E4 target, pGTag-2A-Gal4VP16-bactin donor vector genomic target: GTTCCTGTAGAGAGGGATGAAGG (SEQ ID NO: 85)
donor target: GGGAGGCGTTCGGGCCACAGCGG (SEQ ID NO: 77)
5' spacer: aaa
24 bp 5' homology (ACGGATACTTCATGGTGCCCTTCA; SEQ ID NO: 86)
3' spacer: N/A
24 bp 3' homology (TCCCTCTCTACAGGAACGGAGACT (SEQ ID NO: 87)

rb1 E2-E4 target, pGTag-2A-Gal4VP16-bactin donor vector genomic E2 target: GGAGAGGGAGATCAGATCGATGG (SEQ ID NO: 88)
genomic E4 target: GTCACAGCAGAGTTCACTTTAGG (SEQ ID NO: 89)
donor target: GGGAGGCGTTCGGGCCACAGCGG (SEQ ID NO: 77)
5' spacer: N/A
48 bp 5' homology (GCTCCAGTCCACTAACTCCATCTGTGATCATGCATGGAGAATATGGGA; SEQ ID NO: 90)
3' spacer: N/A

TABLE 1-continued

Targeting domain information for GeneWeld experiments 48 bp 3' homology (ACCCGCCTAGAGAACAAATACGATGTGACTTTGGCCCTCTACCAAAGA; SEQ ID NO: 91)

rb1 E2-E25 target, pGTag-2A-Gal4VP16-bactin donor vector genomic E2 target: GGAGAGGGAGATCAGATCGATGG (SEQ ID NO: 88)
genomic E25 target: GTCAAAGCGCAGCCTCTTCAGGG (SEQ ID NO: 92)
donor target: GGGAGGCGTTCGGGCCACAGCGG (SEQ ID NO: 75)
5' spacer: N/A
48 bp 5' homology (GCTCCAGTCCACTAACTCCATCTGTGATCATGCATGGAGAATATGGGA; SEQ ID NO: 90)
3' homology: N/A
48 bp 3' homology (ATGGACGGACAAGATGAAGCAGACGGAAGgtgggagtcatgatcagtt; SEQ ID NO: 93)

msna E2-E6 target, pGTag-2A-Gal4VP16-bactin donor vector genomic E2 target: GTTTCCCTGTGGTGCTGGGTTGG (SEQ ID NO: 94)
genomic E6 target: GTCTGGCACGAGGAGCACAAGGG (SEQ ID NO: 95)
donor target: GGGAGGCGTTCGGGCCACAGCGG (SEQ ID NO: 75)
5' spacer: ttt
48 bp 5' homology (TGTTCGTGTGACTACAATGGATGCCGAGCTGGAGTTTGCCATCCAACC; SEQ ID NO: 96)
3' spacer: aaa
48 bp 3' homology (CAAGGGCATGTTGAGGTACAGACAATGGAATGTGCTCTTGCTATTTTT; SEQ ID NO: 97)

esama E2 target, pGTag-2A-Gal4VP16-bactin donor vector genomic target: GGATGTGATCCAAGGGAAGATGG (SEQ ID NO: 98)
donor target: GGGAGGCGTTCGGGCCACAGCGG (SEQ ID NO: 75)
5' spacer: ctc
24 bp 5' homology (AAAATGTGGATGTGATCCAAGGGA; SEQ ID NO: 99)
3' spacer: gag
24 bp 3' homology (AGATGGTGGTGCTGCAGGCTTCA; SEQ ID NO: 100)

E = exon targeted,
N/A = not applicable,
CRISPR/Cas9 PAM underlined.

TABLE 2A

Somatic gene targeting experiments in zebrafish.

| Genomic target | Donor vector | Donor sgRNA target* | Homology length (5'/3') | Expt. number | Reporter positive embryos | Total embryos | % with + report |
|---|---|---|---|---|---|---|---|
| noto E1 | 2A-TagRFP-CAAX-SV40 | genomic sgRNA | 12/x | 1 | 4 | 32 | 12.5% |
|  | 2A-TagRFP-CAAX-SV40 | genomic sgRNA | 12/x | 2 | 12 | 91 | 13.2% |
|  | 2A-TagRFP-CAAX-SV40 | genomic sgRNA | 12/x | 3 | 6 | 55 | 10.9% |
|  |  |  |  | Average | 22 | 178 | 12.4% |
| noto E1 | 2A-TagRFP-CAAX-SV40 | genomic sgRNA | 24/x | 1 | 10 | 47 | 21.3% |
|  | 2A-TagRFP-CAAX-SV40 | genomic sgRNA | 24/x | 2 | 10 | 41 | 24.4% |
|  | 2A-TagRFP-CAAX-SV40 | genomic sgRNA | 24/x | 3 | 10 | 43 | 23.3% |
|  |  |  |  | Average | 30 | 131 | 22.9% |
| noto E1 | 2A-TagRFP-CAAX-SV40 | genomic sgRNA | 48/x | 1 | 10 | 29 | 34.5% |
|  | 2A-TagRFP-CAAX-SV40 | genomic sgRNA | 48/x | 2 | 15 | 40 | 37.5% |
|  | 2A-TagRFP-CAAX-SV40 | genomic sgRNA | 48/x | 3 | 15 | 45 | 33.3% |
|  |  |  |  | Average | 40 | 114 | 35.1% |
| noto E2 | 2A-TagRFP-CAAX-SV40 | UgRNA | 24/x | 1 | 13 | 62 | 21.0% |
|  | 2A-TagRFP-CAAX-SV40 | UgRNA | 24/x | 2 | 10 | 49 | 20.4% |
|  | 2A-TagRFP-CAAX-SV40 | UgRNA | 24/x | 3 | 9 | 39 | 23.1% |
|  |  |  |  | Average | 32 | 150 | 21.3% |
| noto E1 | pGTag-2A-TagRFP-CAAX-SV40 | UgRNA | 24/24 | 1 | 18 | 68 | 26.5% |
|  | pGTag-2A-TagRFP-CAAX-SV40 | UgRNA | 24/24 | 2 | 9 | 38 | 23.7% |
|  | pGTag-2A-TagRFP-CAAX-SV40 | UgRNA | 24/24 | 3 | 6 | 28 | 21.4% |
|  | pGTag-2A-TagRFP-CAAX-SV40 | UgRNA | 24/24 |  | 12 | 51 | 23.5% |
|  |  |  |  | Average | 45 | 185 | 24.3% |
| tyr E4 | pGTag-2A-Gal4VP16-bactin | UgRNA | 24/24 | 1 | 21 | 31 | 67.7% |
|  | pGTag-2A-Gal4VP16-bactin | UgRNA | 24/24 | 2 | 21 | 33 | 63.6% |
|  | pGTag-2A-Gal4VP16-bactin | UgRNA | 24/24 | 3 | 42 | 68 | 61.8% |
|  |  |  |  | Average | 84 | 132 | 63.6% |
| tyr E4 | 2A-TagRFP-CAAX-SV40 | genomic sgRNA | 24/x | 1 | 0 | 41 | 0.0% |
|  | 2A-TagRFP-CAAX-SV40 | genomic sgRNA | 24/x | 2 | 0 | 22 | 0.0% |
|  |  |  |  | Average | 0 | 63 | 0.0% |
| rb1 E2-4 | pGTag-2A-Gal4VP16-bactin | UgRNA | 48/48 | 1 | 48 | 108 | 44.0% |
|  | pGTag-2A-Gal4VP16-bactin | UgRNA | 48/48 | 2 | 56 | 111 | 50.0% |
|  | pGTag-2A-Gal4VP16-bactin | UgRNA | 48/48 | 3 | 53 | 96 | 55.0% |
|  | pGTag-2A-Gal4VP16-bactin | UgRNA | 48/48 | 4 | 116 | 148 | 78.0% |
|  |  |  |  | Average | 157 | 315 | 50.0% |
| rb1 E2-25 | pGTag-2A-Gal4VP16-bactin | UgRNA | 48/48 | 1 | 47 | 76 | 62.0% |
|  | pGTag-2A-Gal4VP16-bactin | UgRNA | 48/48 | 2 | 58 | 119 | 49.0% |
|  | pGTag-2A-Gal4VP16-bactin | UgRNA | 48/48 | 3 | 87 | 149 | 58.0% |
|  | pGTag-2A-Gal4VP16-bactin | UgRNA | 48/48 | 4 | 100 | 142 | 70.0% |
|  |  |  |  | Average | 192 | 344 | 56.0% |

TABLE 2A-continued

Somatic gene targeting experiments in zebrafish.

| Genomic target | Donor vector | Donor sgRNA target* | Homology length (5'/3') | Expt. number | Reporter positive embryos | Total embryos | % with + report |
|---|---|---|---|---|---|---|---|
| esama E2 | pGTag-2A-Gal4VP16-bactin | UgRNA | 48/48 | 1 | 9 | 40 | 22.5% |
| | pGTag-2A-Gal4VP16-bactin | UgRNA | 48/48 | 2 | 13 | 65 | 20.0% |
| | pGTag-2A-Gal4VP16-bactin | UgRNA | 48/48 | 3 | 12 | 57 | 21.1% |
| | | | | Average | 34 | 162 | 21.0% |
| noto E1 | pGTag-2A-eGFP-SV40 | UgRNA | 48/48 | 1 | 9 | 33 | 27.3% |
| | pGTag-2A-eGFP-SV40 | UgRNA | 48/48 | 2 | 17 | 71 | 23.9% |
| | pGTag-2A-eGFP-SV40 | UgRNA | 48/48 | 3 | 18 | 68 | 26.5% |
| | | | | Average | 44 | 172 | 25.6% |
| cx43.4 E1 | pGTag-2A-TagRFP-CAAX-SV40 | UgRNA | 48/48 | 1 | 10 | 34 | 29.4% |
| | pGTag-2A-TagRFP-CAAX-SV40 | UgRNA | 48/48 | 2 | 15 | 32 | 46.9% |
| | pGTag-2A-TagRFP-CAAX-SV40 | UgRNA | 48/48 | 3 | 6 | 15 | 40.0% |
| | | | | Average | 31 | 81 | 38.3% |
| cx43.4 E1 | pGTag-2A-TagRFP-CAAX-SV40 | UgRNA | 24/24 | 1 | 8 | 21 | 38.1% |
| | pGTag-2A-TagRFP-CAAX-SV40 | UgRNA | 24/24 | 2 | 15 | 29 | 51.7% |
| | pGTag-2A-TagRFP-CAAX-SV40 | UgRNA | 24/24 | 3 | 19 | 34 | 55.9% |
| | | | | Average | 42 | 84 | 50.0% |
| msna E2-E6 | pGTag-2A-Gal4VP16-bactin | UgRNA | 48/48 | 1 | 8 | 13 | 61.5% |
| | pGTag-2A-Gal4VP16-bactin | UgRNA | 48/48 | 2 | 29 | 34 | 85.3% |
| | pGTag-2A-Gal4VP16-bactin | UgRNA | 48/48 | 3 | 17 | 34 | 50.0% |
| | pGTag-2A-Gal4VP16-bactin | UgRNA | 48/48 | 4 | 26 | 48 | 54.2% |
| | pGTag-2A-Gal4VP16-bactin | UgRNA | 48/48 | 5 | 11 | 22 | 50.0% |
| | | | | Average | 91 | 151 | 60.3% |
| noto E1 | 2A-TagRFP-CAAX-SV40 | genomic sgRNA | 47/x | 1 | 2 | 40 | 5.0% |
| | 2A-TagRFP-CAAX-SV40 | genomic sgRNA | 47/x | 2 | 6 | 22 | 27.3% |
| | 2A-TagRFP-CAAX-SV40 | genomic sgRNA | 47/x | 3 | 6 | 35 | 17.1% |
| | | | | Average | 14 | 97 | 14.4% |
| noto E1 | 2A-TagRFP-CAAX-SV40 | genomic sgRNA | 48/x | 1 | 22 | 47 | 46.8% |
| | 2A-TagRFP-CAAX-SV40 | genomic sgRNA | 48/x | 2 | 29 | 83 | 34.9% |
| | 2A-TagRFP-CAAX-SV40 | genomic sgRNA | 48/x | 3 | 28 | 90 | 31.1% |
| | 2A-TagRFP-CAAX-SV40 | genomic sgRNA | 48/x | 4 | 22 | 64 | 34.4% |
| | 2A-TagRFP-CAAX-SV40 | genomic sgRNA | 48/x | 5 | 13 | 58 | 22.4% |
| | 2A-TagRFP-CAAX-SV40 | genomic sgRNA | 48/x | 6 | 21 | 54 | 38.9% |
| | 2A-TagRFP-CAAX-SV40 | genomic sgRNA | 48/x | 7 | 5 | 13 | 38.5% |
| | 2A-TagRFP-CAAX-SV40 | genomic sgRNA | 48/x | 8 | 12 | 32 | 37.5% |
| | | | | Average | 152 | 441 | 34.5% |
| noto E1 | 2A-TagRFP-CAAX-SV40 | genomic sgRNA | 49/x | 1 | 5 | 67 | 7.5% |
| | 2A-TagRFP-CAAX-SV40 | genomic sgRNA | 49/x | | 6 | 29 | 20.7% |
| | 2A-TagRFP-CAAX-SV40 | genomic sgRNA | 49/x | | 5 | 29 | 17.2% |
| | | | | Average | 16 | 125 | 12.8% |

*genomic or UgRNA x = no homology arm,

E = exon targeted

TABLE 2B

Somatic gene targeting experiments in zebrafish - totals and averages across all loci targeted.

| Genomic target | Donor vector | Donor sgRNA target* | Homology length (5'/3') | Reporter + embryos | Total embryos | % with + report | SEM |
|---|---|---|---|---|---|---|---|
| noto E1 | 2A-TagRFP-CAAX-SV40 | genomic sgRNA | 12/x | 22 | 178 | 12.4% | 0.006807 |
| noto E1 | 2A-TagRFP-CAAX-SV40 | genomic sgRNA | 24/x | 30 | 131 | 22.9% | 0.01286 |
| noto E1 | 2A-TagRFP-CAAX-SV40 | genomic sgRNA | 48/x | 40 | 114 | 35.1% | 0.01 |
| noto E1 | pGTag-2A-eGFP-SV40 | UgRNA | 48/48 | 44 | 172 | 25.6% | 0.01026 |
| noto E2 | 2A-TagRFP-CAAX-SV40 | UgRNA | 24/x | 32 | 150 | 21.3% | 0.008185 |
| noto E1 | pGTag-2A-TagRFP-CAAX-SV40 | UgRNA | 24/24 | 45 | 185 | 24.3% | 0.01047 |
| noto E1 | 2A-TagRFP-CAAX-SV40 | genomic sgRNA | 47/x | 14 | 97 | 14.4% | 0.06361 |
| noto E1 | 2A-TagRFP-CAAX-SV40 | genomic sgRNA | 48/x | 152 | 441 | 34.5% | 0.02917 |
| noto E1 | 2A-TagRFP-CAAX-SV40 | genomic sgRNA | 49/x | 16 | 125 | 12.8% | 0.04092 |
| tyr E4 | pGTag-2A-Gal4VP16-bactin | UgRNA | 24/24 | 84 | 132 | 63.6% | 0.01746 |
| cx43.4 E1 | pGTag-2A-TagRFP-CAAX-SV40 | UgRNA | 48/48 | 31 | 81 | 38.3% | 0.05089 |
| cx43.4 E1 | pGTag-2A-TagRFP-CAAX-SV40 | UgRNA | 24/24 | 42 | 84 | 50.0% | 0.05327 |
| esama E2 | | | | | | | 0.007234 |
| msna E2-E6 | pGTag-2A-Gal4VP16-bactin | UgRNA | 48/48 | 91 | 151 | 60.3% | 0.06617 |
| rb1 E2-E4 | pGTag-2A-Gal4VP16-bactin | UgRNA | 48/48 | 157 | 315 | 50.0% | 0.07432 |
| rb1 E2-E25 | pGTag-2A-Gal4VP16-bactin | UgRNA | 48/48 | 192 | 344 | 56.0% | 0.04366 |

*genomic or UgRNA
x = no homology arm,
E = exon targeted

TABLE 3

GeneWeld experiment F0 outcrosses for zebrafish.

| Target | Knock-in | Homology length | Ind. F0 | Crossed to | Reporter positive F1 embryos | Total F1 embryos | % germline transmission |
|---|---|---|---|---|---|---|---|
| noto E1 | pGTag-2A-TagRFP-CAAX-SV40 | 24/24 | 1 | Casper | 4 | 28 | 14.3% |
| noto E1 | pGTag-2A-TagRFP-CAAX-SV40 | 24/24 | 2 | Casper | 0 | 172 | 0.0% |
| noto E1 | pGTag-2A-TagRFP-CAAX-SV40 | 24/24 | 3 | Casper | 0 | 15 | 0.0% |
| noto E1 | pGTag-2A-TagRFP-CAAX-SV40 | 24/24 | 4 | Casper | 69 | 146 | 47.3% |
| tyr E4 | pGTag-2A-Gal4VP16-bactin | 24/24 | 1 | UAS:RFP | 0 | 174 | 0.0% |
| tyr E4 | pGTag-2A-Gal4VP16-bactin | 24/24 | 2 | UAS:RFP | 0 | 122 | 0.0% |
| tyr E4 | pGTag-2A-Gal4VP16-bactin | 24/24 | 3 | UAS:RFP | 0 | 45 | 0.0% |
| tyr E4 | pGTag-2A-Gal4VP16-bactin | 24/24 | 1 | UAS:RFP | 0 | 87 | 0.0% |

TABLE 3-continued

GeneWeld experiment F0 outcrosses for zebrafish.

| Target | Knock-in | Homology length | Ind. F0 | Crossed to | Reporter positive F1 embryos | Total F1 embryos | % germline transmission |
|---|---|---|---|---|---|---|---|
| tyr E4 | pGTag-2A-Gal4VP16-bactin | 24/24 | 2 | UAS:RFP | 0 | 103 | 0.0% |
| tyr E4 | pGTag-2A-Gal4VP16-bactin | 24/24 | 3 | UAS:RFP | 8 | 89 | 9.0% |
| tyr E4 | pGTag-2A-Gal4VP16-bactin | 24/24 | 4 | UAS:RFP | | | |
| tyr E4 | pGTag-2A-Gal4VP16-bactin | 24/24 | 3 | UAS:RFP | 13 | 151 | 8.6% |
| tyr E4 | pGTag-2A-Gal4VP16-bactin | 24/24 | 4 | UAS:RFP | 0 | 113 | 0.0% |
| tyr E4 | pGTag-2A-Gal4VP16-bactin | 24/24 | 3 | UAS:RFP | 19 | 155 | 12.3% |
| noto E1 | pGTag-2A-TagRFP-CAAX-SV40 | 24/24 | 1 | Casper | 11 | 61 | 18.0% |
| noto E1 | pGTag-2A-TagRFP-CAAX-SV40 | 24/24 | 5 | Casper | 0 | 81 | 0.0% |
| esama E2 | pGTag-2A-Gal4VP16-bactin | 48/48 | 1 (tank 3) | pDB790 | 0 | 21 | 0.0% |
| esama E2 | pGTag-2A-Gal4VP16-bactin | 48/48 | 2 (tank 3) | pDB790 | 0 | 212 | 0.0% |
| esama E2 | pGTag-2A-Gal4VP16-bactin | 48/48 | 3 (tank 2) | pDB790 | 0 | 31 | 0.0% |
| esama E2 | pGTag-2A-Gal4VP16-bactin | 48/48 | 4 (tank 2) | pDB790 | 1 | 4 | 25.0% |
| esama E2 | pGTag-2A-Gal4VP16-bactin | 48/48 | 5 (tank 2) | pDB790 | 1 | 12 | 8.3% |
| esama E2 | pGTag-2A-Gal4VP16-bactin | 48/48 | 6 (tank 1) | pDB790 | 14 | 104 | 13.5% |
| esama E2 | pGTag-2A-Gal4VP16-bactin | 48/48 | 1 (tank 3) | pDB790 | 0 | 87 | 0.0% |
| esama E2 | pGTag-2A-Gal4VP16-bactin | 48/48 | 2 (tank 3) | pDB790 | 0 | 209 | 0.0% |
| esama E2 | pGTag-2A-Gal4VP16-bactin | 48/48 | 3 (tank 2) | pDB790 | 0 | 132 | 0.0% |
| esama E2 | pGTag-2A-Gal4VP16-bactin | 48/48 | 4 (tank 2) | pDB790 | 4 | 18 | 22.2% |
| esama E2 | pGTag-2A-Gal4VP16-bactin | 48/48 | 5 (tank 2) | pDB790 | 0 | 37 | 0.0% |
| esama E2 | pGTag-2A-Gal4VP16-bactin | 48/48 | 6 (tank 1) | pDB790 | 11 | 43 | 25.6% |
| esama E2 | pGTag-2A-Gal4VP16-bactin | 48/48 | 7 (tank 3) | pDB790 | 14 | 97 | 14.4% |
| esama E2 | pGTag-2A-Gal4VP16-bactin | 48/48 | 8 (tank 2) | pDB790 | 0 | 91 | 0.0% |
| esama E2 | pGTag-2A-Gal4VP16-bactin | 48/48 | 9 (tank 1) | pDB790 | 7 | 127 | 5.5% |
| esama E2 | pGTag-2A-Gal4VP16-bactin | 48/48 | 10 (tank 2) | pDB790 | 0 | 25 | 0.0% |
| esama E2 | pGTag-2A-Gal4VP16-bactin | 48/48 | 4 (tank 2) | pDB790 | 30 | 137 | 21.9% |
| esama E2 | pGTag-2A-Gal4VP16-bactin | 48/48 | 5 (tank 2) | pDB790 | 8 | 265 | 3.0% |
| esama E2 | pGTag-2A-Gal4VP16-bactin | 48/48 | 6 (tank 1) | pDB790 | 31 | 227 | 13.7% |
| esama E2 | pGTag-2A-Gal4VP16-bactin | 48/48 | 9 (tank 1) | pDB790 | 11 | 146 | 7.5% |
| esama E2 | pGTag-2A-Gal4VP16-bactin | 48/48 | 10 (tank 2) | pDB790 | 0 | 188 | 0.0% |
| esama E2 | pGTag-2A-Gal4VP16-bactin | 48/48 | 11 (tank 2) | pDB790 | 3 | 66 | 4.5% |
| rb1 E2-E4 | pGTag-2A-Gal4VP16-bactin | 48/48 | 1 | pDB790 | 0 | 38 | 0.0% |
| rb1 E2-E4 | pGTag-2A-Gal4VP16-bactin | 48/48 | 2 | pDB790 | 0 | 103 | 0.0% |
| rb1 E2-E4 | pGTag-2A-Gal4VP16-bactin | 48/48 | 3 | pDB790 | 0 | 61 | 0.0% |
| rb1 E2-E4 | pGTag-2A-Gal4VP16-bactin | 48/48 | 4 | pDB790 | 0 | 73 | 0.0% |
| rb1 E2-E4 | pGTag-2A-Gal4VP16-bactin | 48/48 | 5 | pDB790 | 0 | 57 | 0.0% |
| rb1 E2-E4 | pGTag-2A-Gal4VP16-bactin | 48/48 | 6 | pDB790 | 0 | 69 | 0.0% |

TABLE 3-continued

GeneWeld experiment F0 outcrosses for zebrafish.

| Target | Knock-in | Homology length | Ind. F0 | Crossed to | Reporter positive F1 embryos | Total F1 embryos | % germline transmission |
|---|---|---|---|---|---|---|---|
| rb1 E2-E4 | pGTag-2A-Gal4VP16-bactin | 48/48 | 7 | pDB790 | 0 | 37 | 0.0% |
| rb1 E2-E4 | pGTag-2A-Gal4VP16-bactin | 48/48 | 8 | pDB790 | 0 | 113 | 0.0% |
| rb1 E2-E4 | pGTag-2A-Gal4VP16-bactin | 48/48 | 9 | pDB790 | 0 | 79 | 0.0% |
| rb1 E2-E4 | pGTag-2A-Gal4VP16-bactin | 48/48 | 10 | pDB790 | 0 | 20 | 0.0% |
| rb1 E2-E4 | pGTag-2A-Gal4VP16-bactin | 48/48 | 11 | pDB790 | 0 | 136 | 0.0% |
| rb1 E2-E4 | pGTag-2A-Gal4VP16-bactin | 48/48 | 12 | pDB790 | 0 | 124 | 0.0% |
| rb1 E2-E4 | pGTag-2A-Gal4VP16-bactin | 48/48 | 13 | pDB790 | 0 | 129 | 0.0% |
| rb1 E2-E4 | pGTag-2A-Gal4VP16-bactin | 48/48 | 14 | pDB790 | 0 | 39 | 0.0% |
| rb1 E2-E4 | pGTag-2A-Gal4VP16-bactin | 48/48 | 15 | pDB790 | 0 | 123 | 0.0% |
| rb1 E2-E4 | pGTag-2A-Gal4VP16-bactin | 48/48 | 16 | pDB790 | 0 | 40 | 0.0% |
| rb1 E2-E4 | pGTag-2A-Gal4VP16-bactin | 48/48 | 17 | pDB790 | 0 | 99 | 0.0% |
| rb1 E2-E4 | pGTag-2A-Gal4VP16-bactin | 48/48 | 18 | pDB790 | 0 | 208 | 0.0% |
| rb1 E2-E4 | pGTag-2A-Gal4VP16-bactin | 48/48 | 19 | pDB790 | 0 | 241 | 0.0% |
| rb1 E2-E25 | pGTag-2A-Gal4VP16-bactin | 48/48 | 1 | pDB790 | 0 | 49 | 0.0% |
| rb1 E2-E25 | pGTag-2A-Gal4VP16-bactin | 48/48 | 2 | pDB790 | 0 | 78 | 0.0% |
| rb1 E2-E25 | pGTag-2A-Gal4VP16-bactin | 48/48 | 3 | pDB790 | 0 | 162 | 0.0% |
| rb1 E2-E25 | pGTag-2A-Gal4VP16-bactin | 48/48 | 4 | pDB790 | 12 | 25 | 48.0% |
| rb1 E2-E25 | pGTag-2A-Gal4VP16-bactin | 48/48 | 5 | pDB790 | 0 | 79 | 0.0% |
| rb1 E2-E25 | pGTag-2A-Gal4VP16-bactin | 48/48 | 6 | pDB790 | 0 | 4 | 0.0% |
| rb1 E2-E25 | pGTag-2A-Gal4VP16-bactin | 48/48 | 7 | pDB790 | 0 | 200 | 0.0% |
| rb1 E2-E25 | pGTag-2A-Gal4VP16-bactin | 48/48 | 8 | pDB790 | 0 | 38 | 0.0% |
| rb1 E2-E25 | pGTag-2A-Gal4VP16-bactin | 48/48 | 9 | pDB790 | 0 | 128 | 0.0% |
| rb1 E2-E25 | pGTag-2A-Gal4VP16-bactin | 48/48 | 10 | pDB790 | 0 | 7 | 0.0% |
| rb1 E2-E25 | pGTag-2A-Gal4VP16-bactin | 48/48 | 11 | pDB790 | 0 | 119 | 0.0% |
| rb1 E2-E25 | pGTag-2A-Gal4VP16-bactin | 48/48 | 12 | pDB790 | 0 | 136 | 0.0% |
| rb1 E2-E25 | pGTag-2A-Gal4VP16-bactin | 48/48 | 13 | pDB790 | 0 | 76 | 0.0% |
| rb1 E2-E25 | pGTag-2A-Gal4VP16-bactin | 48/48 | 14 | pDB790 | 0 | 159 | 0.0% |
| rb1 E2-E25 | pGTag-2A-Gal4VP16-bactin | 48/48 | 15 | pDB790 | 0 | 168 | 0.0% |
| rb1 E2-E25 | pGTag-2A-Gal4VP16-bactin | 48/48 | 16 | pDB790 | 0 | 139 | 0.0% |
| rb1 E2-E25 | pGTag-2A-Gal4VP16-bactin | 48/48 | 17 | pDB790 | 0 | 25 | 0.0% |
| rb1 E2-E25 | pGTag-2A-Gal4VP16-bactin | 48/48 | 18 | pDB790 | 0 | 4 | 0.0% |
| rb1 E2-E25 | pGTag-2A-Gal4VP16-bactin | 48/48 | 19 | pDB790 | 0 | 81 | 0.0% |
| rb1 E2-E25 | pGTag-2A-Gal4VP16-bactin | 48/48 | 20 | pDB790 | 0 | 71 | 0.0% |
| rb1 E2-E25 | pGTag-2A-Gal4VP16-bactin | 48/48 | 21 | pDB790 | 0 | 75 | 0.0% |
| rb1 E2-E25 | pGTag-2A-Gal4VP16-bactin | 48/48 | 22 | pDB790 | 0 | 81 | 0.0% |
| rb1 E2-E25 | pGTag-2A-Gal4VP16-bactin | 48/48 | 23 | pDB790 | 0 | 76 | 0.0% |
| rb1 E2-E25 | pGTag-2A-Gal4VP16-bactin | 48/48 | 24 | pDB790 | 0 | 72 | 0.0% |

TABLE 3-continued

GeneWeld experiment F0 outcrosses for zebrafish.

| Target | Knock-in | Homology length | Ind. F0 | Crossed to | Reporter positive F1 embryos | Total F1 embryos | % germline transmission |
|---|---|---|---|---|---|---|---|
| rb1 E2-E25 | pGTag-2A-Gal4VP16-bactin | 48/48 | 25 | pDB790 | 0 | 69 | 0.0% |
| rb1 E2-E25 | pGTag-2A-Gal4VP16-bactin | 48/48 | 26 | pDB790 | 0 | 33 | 0.0% |
| rb1 E2-E25 | pGTag-2A-Gal4VP16-bactin | 48/48 | 27 | pDB790 | 0 | 74 | 0.0% |
| cx43.4 E2 | pGTag-2A-TagRFP-CAAX-SV40 | 48/48 | 1 | fli1:EGFP | 0 | 130 | 0.0% |
| cx43.4 E2 | pGTag-2A-TagRFP-CAAX-SV40 | 48/48 | 2 | fli1:EGFP | 0 | 100 | 0.0% |
| cx43.4 E2 | pGTag-2A-TagRFP-CAAX-SV40 | 48/48 | 3 | fli1:EGFP | 0 | 75 | 0.0% |
| cx43.4 E2 | pGTag-2A-TagRFP-CAAX-SV40 | 48/48 | 4 | fli1:EGFP | 0 | 52 | 0.0% |
| cx43.4 E2 | pGTag-2A-TagRFP-CAAX-SV40 | 48/48 | 5 | fli1:EGFP | 0 | 0 | N/A |
| cx43.4 E2 | pGTag-2A-TagRFP-CAAX-SV40 | 48/48 | 6 | fli1:EGFP | 0 | 12 | 0.0% |
| cx43.4 E2 | pGTag-2A-TagRFP-CAAX-SV40 | 48/48 | 7 | fli1:EGFP | 0 | 0 | N/A |
| cx43.4 E2 | pGTag-2A-TagRFP-CAAX-SV40 | 48/48 | 8 | fli1:EGFP | 0 | 0 | N/A |
| cx43.4 E2 | pGTag-2A-TagRFP-CAAX-SV40 | 48/48 | 9 | fli1:EGFP | 0 | 34 | 0.0% |
| cx43.4 E2 | pGTag-2A-TagRFP-CAAX-SV40 | 48/48 | 10 | fli1:EGFP | 0 | 86 | 0.0% |
| cx43.4 E2 | pGTag-2A-TagRFP-CAAX-SV40 | 48/48 | 11 | fli1:EGFP | 0 | 0 | N/A |
| cx43.4 E2 | pGTag-2A-TagRFP-CAAX-SV40 | 48/48 | 12 | fli1:EGFP | 0 | 0 | N/A |
| cx43.4 E2 | pGTag-2A-TagRFP-CAAX-SV40 | 48/48 | 13 | fli1:EGFP | 0 | 0 | N/A |
| cx43.4 E2 | pGTag-2A-TagRFP-CAAX-SV40 | 48/48 | 14 | fli1:EGFP | 0 | 0 | N/A |
| cx43.4 E2 | pGTag-2A-TagRFP-CAAX-SV41 | 24/24 | 1 | fli1:EGFP | 0 | 39 | 0.0% |
| cx43.4 E2 | pGTag-2A-TagRFP-CAAX-SV42 | 24/24 | 2 | fli1:EGFP | 0 | 0 | N/A |
| cx43.4 E2 | pGTag-2A-TagRFP-CAAX-SV43 | 24/24 | 3 | fli1:EGFP | 0 | 0 | N/A |
| cx43.4 E2 | pGTag-2A-TagRFP-CAAX-SV44 | 24/24 | 4 | fli1:EGFP | 0 | 15 | 0.0% |
| cx43.4 E2 | pGTag-2A-TagRFP-CAAX-SV45 | 24/24 | 5 | fli1:EGFP | 0 | 26 | 0.0% |
| cx43.4 E2 | pGTag-2A-TagRFP-CAAX-SV46 | 24/24 | 6 | fli1:EGFP | 0 | 0 | N/A |
| cx43.4 E2 | pGTag-2A-TagRFP-CAAX-SV47 | 24/24 | 7 | fli1:EGFP | 0 | 23 | 0.0% |
| cx43.4 E2 | pGTag-2A-TagRFP-CAAX-SV48 | 24/24 | 8 | fli1:EGFP | 0 | 0 | N/A |

TABLE 3-continued

GeneWeld experiment F0 outcrosses for zebrafish.

| Target | Knock-in | Homology length | Ind. F0 | Crossed to | Reporter positive F1 embryos | Total F1 embryos | % germline transmission |
|---|---|---|---|---|---|---|---|
| cx43.4 E2 | pGTag-2A-TagRFP-CAAX-SV49 | 24/24 | 9 | fli1:EGFP | 0 | 45 | 0.0% |
| cx43.4 E2 | pGTag-2A-TagRFP-CAAX-SV50 | 24/24 | 10 | fli1:EGFP | 0 | 82 | 0.0% |
| msna E2-E6 | pGTag-2A-Gal4VP16-bactin | 48/48 | 1 | pDB790 | 0 | 180 | 0.0% |
| msna E2-E6 | pGTag-2A-Gal4VP16-bactin | 48/48 | 2 | pDB790 | 0 | 53 | 0.0% |
| msna E2-E6 | pGTag-2A-Gal4VP16-bactin | 48/48 | 3 | pDB790 | 0 | 0 | N/A |
| msna E2-E6 | pGTag-2A-Gal4VP16-bactin | 48/48 | 4 | pDB790 | 0 | 0 | N/A |
| msna E2-E6 | pGTag-2A-Gal4VP16-bactin | 48/48 | 5 | pDB790 | 0 | 93 | 0.0% |
| msna E2-E6 | pGTag-2A-Gal4VP16-bactin | 48/48 | 6 | pDB790 | 0 | 23 | 0.0% |
| msna E2-E6 | pGTag-2A-Gal4VP16-bactin | 48/48 | 7 | pDB790 | 0 | 357 | 0.0% |
| msna E2-E6 | pGTag-2A-Gal4VP16-bactin | 48/48 | 8 | pDB790 | 0 | 100 | 0.0% |
| msna E2-E6 | pGTag-2A-Gal4VP16-bactin | 48/48 | 9 | pDB790 | 0 | 235 | 0.0% |
| msna E2-E6 | pGTag-2A-Gal4VP16-bactin | 48/48 | 10 | pDB790 | 0 | 237 | 0.0% |
| msna E2-E6 | pGTag-2A-Gal4VP16-bactin | 48/48 | 11 | pDB790 | 0 | 84 | 0.0% |
| msna E2-E6 | pGTag-2A-Gal4VP16-bactin | 48/48 | 12 | pDB790 | 0 | 117 | 0.0% |

TABLE 4

Zebrafish germline transmission

| Genomic target | F0s outcrossed | F0s transmitting | Germline transmission percentage |
|---|---|---|---|
| noto E1 | 5 | 2 | 40.0% |
| tyr E4 | 7 | 1 | 14.3% |
| esamaE2 | 12 | 7 | 58.3% |
| rb1 E2-E4 | 19 | 0 | 0.0% |
| rb1 E2-E25 | 27 | 1 | 3.7% |
| cx43.4 E2 24/24 | | | |
| cx43.4 E2 48/48 | | | |
| msna E2-E6 | | | |

TABLE 5

Primers and probes

| Primer Name | Sequence | SEQ ID: |
|---|---|---|
| Junction fragment analysis | | |
| notojxn5'f | GCTTTTTGGACTAAACAGACGCCATG | 101 |
| notojxn3'r | CTTGTGCGTACACAGCTCCACG | 102 |
| notojxn3'delr | CGATGTTATACTTGCTTCTTTTTAGTTTTGTACATAT | 103 |
| tyrjxn5'f | CATCTTTGAGCAGTGGTTGAGGAGA | 104 |
| tyrjxn3'r | CACCTGGATCCTGTAAAATGCATATTCATATC | 105 |

TABLE 5-continued

Primers and probes

| Primer Name | Sequence | SEQ ID: |
|---|---|---|
| esamajxn5'f | GGTCTTTCAGTCAGCGAGTTTAATGTC | 106 |
| esamajxn3'r | CATTTCAGTGCTGGTAGCAGACTG | 107 |
| cx43.4jxn5'f | GCAGGACTGAGACGGTGGTA | 108 |
| cx43.4fxn3'r | CAAATGCATCGTAGCAAACG | 109 |
| Rb2jF | AAGGACAAGGATCCTGAGTTTG | 110 |
| galjf | GCAAACGGCCTTAACTTTCC | 63 |
| GaljR | GCCTTGATTCCACTTCTGTCA | 60 |
| Rb4jR | GCTTTGCATCACAACCTCAA | 111 |
| Rb25jR | AGCCAGCTTCTGGATCAGTG | 112 |
| RFP5'jxnr | CCTTAATCAGTTCCTCGCCCTTAGA | 61 |
| sv403'jxnf | GGGGAGGTGTGGGAGGTTTT | 113 |
| gfp5'R | GCTGAACTTGTGGCCGTTTA | 62 |
| GFP3'F | ACATGGTCCTGCTGGAGTTC | 66 |
| F-msna-exon2 | TTCCTTCATTCATTCATTGACA | 114 |
| R-msna-exon6 | CGTGTGATTGACAGGGTCAC | 115 |

TABLE 5-continued

Primers and probes

| Primer Name | Sequence | SEQ ID: |
|---|---|---|
| Southern blot analysis | | |
| notoSBf | CAGATGCCACACTTCGCGT | 116 |
| notoSBr | CGATGTTATACTTGCTTCTTTTTAGTTTTGTACATAT | 117 |
| tyrSBe3f | GTTTTGCTAATCCTGAGACGGGTTTG | 118 |
| tyrSBe3r | CTGTCAATAAAAGCATGATGTATGATGAAAATGG | 119 |
| esamaSBe3f | ATCATCTCATTCGTCAATGGAGACTTCAG | 120 |
| esamaSBi4r | CACAGTGTGGCAGTGAGCATTC | 121 |
| gal4SBr | CTGAAGAACAACTGGGAGTGTCGC | 122 |
| gal4SBf | TTACATATCCAGAGCGCCGTAGGG | 123 |
| rfpSBf | ATGGTGTCTAAGGGCGAAGAGC | 124 |
| rfpSBr | AGCTTCAGGGCCATGTCGC | 125 |
| pGTag Cloning | | |
| F-2A-Gal4-BamHI | GGATCCGGAGCCACGAACTTCTCTCTGTTAAAGCAAGCAGGAGACGTGGAAGAAAACCCCGGTCCTTCTAGAAAGCTACTGTCTTCTATCGAACAAGCA | 126 |
| R-Gal4-NcoI | GCATCCATGGTAATTTATTTAGCAGTAGATAGCTATATTGTGTGAAACGC | 127 |
| F-eGFP-speI | AGACATACTAGTATGGTGAGCAAGGGCGAGGAGCTG | 128 |
| R-eGFP-XhoI | TGGATCCTCGAGTTACTTGTACAGCTCGT | 129 |
| F-p494-XhoI | CGCTGCCTCGAGGGCGCGCCTCTAGAACTATAG | 130 |
| R-p494-SpeI | AGCCATACTAGTAGGACCGGGGTTTTCTT | 131 |
| F-lacZ | TGATACACGCAGGTGCGCAACGCAATTAATGTGAGTT | 132 |
| R-lacZ | ATCCTGTGGCAGGTCCATTCGCCATTCAGGCTGC | 133 |
| F-lacZ-universal-1 | GGGAGGCGTTCGGGCCACAGCGGACACGCAGGTGCGCAACGCAATTAATG | 134 |
| R-lacZ-universal-BamHI | CTGATCGGATCCTGTGGCAGGTCCATTCG | 135 |
| F-lacZ-universal-EcoRI | GTACATGAATTCGGGAGGCGTTCGGGCCACAG | 136 |
| F-3'-uni-1 | CGTTGTCTAGCAAGGAAGTGAAGA | 137 |
| R-3'-uni-1 | GGGAGGCGTTCGGGCCACAGCGGAGAAGAGCATATTCAATGTCG | 138 |
| F-3'-uniNco1 | TGCAGCCATGGCGTTGTCTAGCAAGGAAGTGAAGA | 139 |
| R-3'-uniEagI | TCGAGCGGCCGAGATCCCATCGCTAGCGGG | 140 |
| F-TagRFPfix | 5'phos\CTTAATCAGTTCCTCGCCCTTAG | 141 |
| R-TagRFPfix | 5'phos\GAGAACATGCACATGAAGCTGTAC | 142 |
| F-BBfix | 5'phos\AATACGCAAACCGCCTCTCC | 143 |
| R-BBfix | 5'phos\GGGCGCACATCCGCTTC | 144 |
| F-Bactfix | 5'phos\TTTAAAAGTCAAACCACCATGACTG | 145 |
| R-Bactfix | 5'phos\CTGGCAGTTCCTTCCTGTTAA | 146 |
| F-Bact-AscI | ATATGTGGCGCGCCACGGACTGTTACCACTTCACG | 147 |
| R-Bact-NcoI | ACAACGCCATGGTAATTTATTTAGC | 148 |
| F-gal4-Ecofix | 5'phos\ACAGATCTCTCGAGCCGCCCC | 149 |
| R-gal4-Ecofix | 5'phos\ATTCCCGGGGTCGACCTCGA | 150 |
| ssRosa HDR Donor Cloning | | |
| ssRosa 760 5'HR F | GGAGAGAGCTGCACAAGAGGGC | 151 |
| ssRosa 5'HR R | GATATCGCTAGCACCGGTGCGGCCGCGTTTAAACACTAGTCCCGGGGGACAACGCCCAAGAATCAG | 152 |
| ssRosa 3'HR F | CCCGGGACTAGTGTTTAAACGCGGCCGCACCGGTGCTAGCGATATCTGCAGGGGATTGAGCAGGTG | 153 |
| ssRosa 736 3'HR R | AGCATTACGGCAACTGAGCT | 154 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid construct for modifying genomic DNA of a cell, wherein said nucleic acid construct comprises, in order from 5' to 3':
    (a) a first guide RNA (gRNA) target sequence, wherein said first gRNA target sequence comprises the nucleotide sequence set forth in SEQ ID NO:45,
    (b) a 5' homology sequence that is homologous to a sequence 5' of a selected target sequence present in said genomic DNA of said cell, wherein said first gRNA target sequence and said 5' homology sequence are not contiguous with each other in said genomic DNA of said cell, and wherein the length of said 5' homology sequence is 24 base pairs,
    (c) a donor sequence to be inserted into said selected target sequence, and
    (d) a 3' homology sequence that is homologous to a sequence 3' of said selected target sequence, wherein the length of said 3' homology sequence is 24 base pairs.

2. The nucleic acid construct of claim 1, wherein the construct further comprises a second gRNA target sequence, wherein the second gRNA target sequence is 3' of the 3' homology sequence.

3. The nucleic acid construct of claim 2, wherein the first and second gRNA target sequences are targets for the same gRNA.

4. The nucleic acid construct of claim 1, wherein the construct further comprises one or both of
    (a) between the 5' homology sequence and the donor sequence, a sequence encoding a peptide that causes translational skipping, and
    (b) between the donor sequence and the 3' homology sequence, a polyadenylation sequence (pA).

5. The nucleic acid construct of claim 1, wherein the donor sequence to be inserted encodes a reporter.

6. The nucleic acid construct of claim 1, wherein said first gRNA target sequence is not present in said genomic DNA of said cell.

7. A nucleic acid construct for modifying genomic DNA of a cell, wherein said nucleic acid construct comprises, in order from 5' to 3':
    (a) a first guide RNA (gRNA) target sequence, wherein said first gRNA target sequence comprises the nucleotide sequence set forth in SEQ ID NO:45,
    (b) a 5' homology sequence that is homologous to a sequence 5' of a selected target sequence present in said genomic DNA of said cell, wherein said first gRNA target sequence and said 5' homology sequence are not contiguous with each other in said genomic DNA of said cell, and wherein the length of said 5' homology sequence is 48 base pairs,
    (c) a donor sequence to be inserted into said selected target sequence, and
    (d) a 3' homology sequence that is homologous to a sequence 3' of said selected target sequence, wherein the length of said 3' homology sequence is 48 base pairs.

8. The nucleic acid construct of claim 7, wherein the construct further comprises a second gRNA target sequence, wherein the second gRNA target sequence is 3' of the 3' homology sequence.

9. The nucleic acid construct of claim 8, wherein the first and second gRNA target sequences are targets for the same gRNA.

10. The nucleic acid construct of claim 7, wherein the construct further comprises one or both of
    (a) between the 5' homology sequence and the donor sequence, a sequence encoding a peptide that causes translational skipping, and
    (b) between the donor sequence and the 3' homology sequence, a polyadenylation sequence (pA).

11. The nucleic acid construct of claim 7, wherein the donor sequence to be inserted encodes a reporter.

12. The nucleic acid construct of claim 7, wherein said first gRNA target sequence is not present in said genomic DNA of said cell.

* * * * *

SEQUENCE LISTING

<160> NUMBER OF SEQ ID NOS: 156

<210> SEQ ID NO 1
<211> LENGTH: 32
<212> TYPE: DNA
<213> ORGANISM: Artificial Sequence
<220> FEATURE:
<223> OTHER INFORMATION: synthetic oligonucleotide

```
<220> FEATURE:
<221> NAME/KEY: misc_feature
<222> LOCATION: (1)..(3)
<223> OTHER INFORMATION: n = a, c, g, or t

<400> SEQUENCE: 1
nnncaaacgc ctgtctcctg ctctgcgctc cc                                    32

<210> SEQ ID NO 2
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (30)..(32)
<223> OTHER INFORMATION: n = a, c, g, or t

<400> SEQUENCE: 2
gggagcgcag agcaggagac aggcgtttgn nn                                    32

<210> SEQ ID NO 3
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(26)
<223> OTHER INFORMATION: n = a, c, g, or t

<400> SEQUENCE: 3
gggagcgcag agcaggagac aggnnncaaa cgcctgtc                              38

<210> SEQ ID NO 4
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(15)
<223> OTHER INFORMATION: n = a, c, g, or t

<400> SEQUENCE: 4
gacaggcgtt tgnnncctgt ctcctgctct gcgctccc                              38

<210> SEQ ID NO 5
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n = a, c, g, or t
<220> FEATURE:
<221> NAME/KEY: misc_feature
<222> LOCATION: (31)..(33)
<223> OTHER INFORMATION: n = a, c, g, or t

<400> SEQUENCE: 5
nnncaaacgc ctgtctcctg ctctgcgctc nnn                                   33

<210> SEQ ID NO 6
```

```
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n = a, c, g, or t
<220> FEATURE:
<221> NAME/KEY: misc_feature
<222> LOCATION: (31)..(33)
<223> OTHER INFORMATION: n = a, c, g, or t

<400> SEQUENCE: 6
nnngagcgca gagcaggaga caggcgtttg nnn                                 33

<210> SEQ ID NO 7
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(26)
<223> OTHER INFORMATION: n = a, c, g, or t

<400> SEQUENCE: 7
gggaggcgtt cgggccacag cggnnncaaa cgcctgtc                            38

<210> SEQ ID NO 8
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(15)
<223> OTHER INFORMATION: n = a, c, g, or t

<400> SEQUENCE: 8
gacaggcgtt tgnnnccgct gtggcccgaa cgcctccc                            38

<210> SEQ ID NO 9
<211> LENGTH: 41
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (16)..(18)
<223> OTHER INFORMATION: n = a, c, g, or t

<400> SEQUENCE: 9
tcctgctctg cgctgnnncc gctgtggccc gaacgcctcc c                        41

<210> SEQ ID NO 10
<211> LENGTH: 41
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(26)
<223> OTHER INFORMATION: n = a, c, g, or t

<400> SEQUENCE: 10
```

```
gggaggcgtt cgggccacag cggnnncagc gcagagcagg a                          41
```

<210> SEQ ID NO 11
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n = a, c, g, or t

<400> SEQUENCE: 11

```
nnncaaacgc ctgtc                                                      15
```

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n = a, c, g, or t

<400> SEQUENCE: 12

```
nnngagcgca gagcagga                                                   18
```

<210> SEQ ID NO 13
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 13

```
gggaggcgtt cgggcca                                                    17
```

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(15)
<223> OTHER INFORMATION: n = a, c, g, or t

<400> SEQUENCE: 14

```
gacaggcgtt tgnnnccgct g                                               21
```

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (16)..(18)
<223> OTHER INFORMATION: n = a, c, g, or t

<400> SEQUENCE: 15

```
tcctgctctg cgctgnnncc gctg                                            24
```

<210> SEQ ID NO 16
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 16
gggaggcgtt cgggcca                                                   17

<210> SEQ ID NO 17
<211> LENGTH: 65
<212> TYPE: DNA
<213> ORGANISM: Danio rerio

<400> SEQUENCE: 17
agagaacgaa caaacgcgta ccggagcata accaaccaaa cgcctgtctc cagctctgcg    60
ctccc                                                                65

<210> SEQ ID NO 18
<211> LENGTH: 65
<212> TYPE: DNA
<213> ORGANISM: Danio rerio

<400> SEQUENCE: 18
gggagcgcag agctggagac aggcgtttgg ttggttatgc tccggtacgc gtttgttcgt    60
tctct                                                                65

<210> SEQ ID NO 19
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 19
gggagcgcag agctggagac aggaaaagag aacgaacaaa cgcgtaccgg agcataacca    60
accaaacgcc tgtc                                                      74

<210> SEQ ID NO 20
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 20
gacaggcgtt tggttggtta tgctccggta cgcgtttgtt cgttctcttt tcctgtctcc    60
agctctgcgc tccc                                                      74

<210> SEQ ID NO 21
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 21
accaaccaaa cgcctgtcgg atcc                                           24

<210> SEQ ID NO 22
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 22
accaaccaaa cgcctgtcag gatcc                                           25

<210> SEQ ID NO 23
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 23
taccggagca taaccaacca aacgcctgtc ggatcc                               36

<210> SEQ ID NO 24
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 24
taccggagca taaccaacca aacgcctgtc taggagcata accaaccaaa cgcctgtcgg     60
atcc                                                                  64

<210> SEQ ID NO 25
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 25
gagatgagag aacgaacaaa cgcgtaccgg agcataacca accaaacgcc tgtcggatcc     60

<210> SEQ ID NO 26
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 26
gagatgagag aagagaacaa acgcgtaccg gagcataacc aaccaaacgc ctgtcggatc     60
c                                                                     61

<210> SEQ ID NO 27
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 27
gagatgagag aacgaacaaa cgcgtaccgg agcataacca accaaacgcc tgtcggattc     60

<210> SEQ ID NO 28
<211> LENGTH: 23
<212> TYPE: RNA
<213> ORGANISM: Artificial Sequence
<220> FEATURE:
```

<223> OTHER INFORMATION: synthetic oligonucleotide

<400> SEQUENCE: 28
gggaggcguu cgggccacag cgg 23

<210> SEQ ID NO 29
<211> LENGTH: 38
<212> TYPE: DNA
<213> ORGANISM: Danio rerio

<400> SEQUENCE: 29
acggatcgga tctgagtcgg gatagcttgg attgctac 38

<210> SEQ ID NO 30
<211> LENGTH: 38
<212> TYPE: DNA
<213> ORGANISM: Danio rerio

<400> SEQUENCE: 30
gtagcaatcc aagctatccc gactcagatc cgatccgt 38

<210> SEQ ID NO 31
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 31
gggaggcgtt cgggccacag cggacggatc ggatctgagt cgggata 47

<210> SEQ ID NO 32
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 32
tatcccgact cagatccgat ccgtccgctg tggcccgaac gcctccc 47

<210> SEQ ID NO 33
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 33
tccagctctg cgctcccgct tattatctgc tctccaactc act 43

<210> SEQ ID NO 34
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 34
tccagctctg cgctcccgct tattccgctt atctgctctc caactcact 49

<210> SEQ ID NO 35
<211> LENGTH: 38
<212> TYPE: DNA
<213> ORGANISM: Artificial Sequence

```
<220> FEATURE:
<223> OTHER INFORMATION: synthetic oligonucleotide

<400> SEQUENCE: 35
acaacgacgg atacttcatg gtgcccttca ttggatcc                              38

<210> SEQ ID NO 36
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 36
acaacgacgg atacttcatg gtgcccttca ttggaccc                              38

<210> SEQ ID NO 37
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 37
acaacgacgg atacttcatg gtgcccttca ttggatcc                              38

<210> SEQ ID NO 38
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 38
ccatggtccc tctctacagg aacggagact attttc                                36

<210> SEQ ID NO 39
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 39
cttatgaaaa tgtggatgtg atccaaggga ttggatcc                              38

<210> SEQ ID NO 40
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 40
cttatgaaaa tgtggttgtg atccaaggga ttggatcc                              38

<210> SEQ ID NO 41
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 41
gataagaaaa tgtggttgtg atccaaggga ttggatcc                              38
```

<210> SEQ ID NO 42
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 42
ccatggagat ggtggtgctg caggcgtcat attcga                                36

<210> SEQ ID NO 43
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 43
ccatggagat ggtggtgctg caggcttcat attcga                                36

<210> SEQ ID NO 44
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 44
ccatggagat ggtggtgctg caggcttcat gaaggtgctg caggcttcat attcga          56

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gggaggcgtt cgggccacag cgg                                              23

<210> SEQ ID NO 46
<211> LENGTH: 57
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (20)..(37)
<223> OTHER INFORMATION: n = a, c, g, or t

<400> SEQUENCE: 46
taatacgact cactataggn nnnnnnnnnn nnnnnnngtt ttagagctag aaatagc         57

<210> SEQ ID NO 47
<211> LENGTH: 22
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(22)
<223> OTHER INFORMATION: n = a, c, g, or t

<400> SEQUENCE: 47
ggnnnnnnnn nnnnnnnnnn nn                                               22

<210> SEQ ID NO 48
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 48
taatacgact cactata                                                  17

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
gttttagagc tagaaatagc                                               20

<210> SEQ ID NO 50
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 50
gatccgcacc gactcggtgc cactttttca agttgataac ggactagcct tattttaact   60
tgctatttct agctctaaaa c                                             81

<210> SEQ ID NO 51
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 51
gatccgcacc gactcggtg                                                19

<210> SEQ ID NO 52
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 52
cggcctcggg atccaccggc cagaatcgat atactacgat gaacagagca aatttgtgtg   60
taatacggtc gccaccatgg cctcctcggt ttgctacgat gcatttgcac cactctctca   120
tgtccggttc tgggaggacg tcatcaagga gttcatgcgc ttcaaggtgc gcatggaggg   180
ctccgtgaac                                                          190

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53

```
ggcgttgtct agcaaggaag                                                 20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
atggctcata acaccccttg                                                 20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
gcatggatgt tttcccagtc                                                 20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
atggctcata acaccccttg                                                 20

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
gggaggcgtt cgggccacag                                                 20

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
gggaggcgtt cgggccacag                                                 20

<210> SEQ ID NO 59
<211> LENGTH: 101
<212> TYPE: RNA
<213> ORGANISM: Artificial Sequence
<220> FEATURE:
<223> OTHER INFORMATION: synthetic oligonucleotide

<400> SEQUENCE: 59
gggaggcguu cgggccacag guuuuagagc uagaaauagc aaguuaaaau aaggcuaguc     60
cguuaucaac uugaaaaagu ggcaccgagu cggugcggau c                        101

<210> SEQ ID NO 60
<211> LENGTH: 21
```

```
<212> TYPE: DNA
<213> ORGANISM: Artificial Sequence
<220> FEATURE:
<223> OTHER INFORMATION: synthetic oligonucleotide

<400> SEQUENCE: 60
gccttgattc cacttctgtc a                                             21

<210> SEQ ID NO 61
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 61
ccttaatcag ttcctcgccc ttaga                                         25

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
gctgaacttg tggccgttta                                               20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
gcaaacggcc ttaactttcc                                               20

<210> SEQ ID NO 64
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
ctacggcgct ctggatatgt                                               20

<210> SEQ ID NO 65
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 65
cgacctccct agcaaactgg gg                                            22

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
```

-continued

```
acatggtcct gctggagttc                                               20

<210> SEQ ID NO 67
<211> LENGTH: 23
<212> TYPE: DNA
<213> ORGANISM: Danio rerio

<400> SEQUENCE: 67
gggagcgcag agctggagac agg                                           23

<210> SEQ ID NO 68
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 68
gggagcgcag agctggagac agg                                           23

<210> SEQ ID NO 69
<211> LENGTH: 12
<212> TYPE: DNA
<213> ORGANISM: Danio rerio

<400> SEQUENCE: 69
caaacgcctg tc                                                       12

<210> SEQ ID NO 70
<211> LENGTH: 24
<212> TYPE: DNA
<213> ORGANISM: Danio rerio

<400> SEQUENCE: 70
agcataacca accaaacgcc tgtc                                          24

<210> SEQ ID NO 71
<211> LENGTH: 48
<212> TYPE: DNA
<213> ORGANISM: Danio rerio

<400> SEQUENCE: 71
agagaacgaa caaacgcgta ccggagcata accaaccaaa cgcctgtc                48

<210> SEQ ID NO 72
<211> LENGTH: 23
<212> TYPE: DNA
<213> ORGANISM: Danio rerio

<400> SEQUENCE: 72
gactggagaa agagttcgcg cgg                                           23

<210> SEQ ID NO 73
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 73
gactggagaa agagttcgcg cgg                                           23

<210> SEQ ID NO 74
<211> LENGTH: 24
```

```
<212> TYPE: DNA
<213> ORGANISM: Danio rerio

<400> SEQUENCE: 74
ctgtccagac tggagaaaga gttc                                          24

<210> SEQ ID NO 75
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 75
gggaggcgtt cgggccacag cgg                                           23

<210> SEQ ID NO 76
<211> LENGTH: 24
<212> TYPE: DNA
<213> ORGANISM: Danio rerio

<400> SEQUENCE: 76
tccagctctg cgctcccgct tatt                                          24

<210> SEQ ID NO 77
<211> LENGTH: 48
<212> TYPE: DNA
<213> ORGANISM: Danio rerio

<400> SEQUENCE: 77
tccagctctg cgctcccgct tatttactcg cagatgccac acttcgcg                48

<210> SEQ ID NO 78
<211> LENGTH: 47
<212> TYPE: DNA
<213> ORGANISM: Danio rerio

<400> SEQUENCE: 78
gagaacgaac aaacgcgtac cggagcataa ccaaccaaac gcctgtc                 47

<210> SEQ ID NO 79
<211> LENGTH: 49
<212> TYPE: DNA
<213> ORGANISM: Danio rerio

<400> SEQUENCE: 79
gagagaacga acaaacgcgt accggagcat aaccaaccaa acgcctgtc               49

<210> SEQ ID NO 80
<211> LENGTH: 23
<212> TYPE: DNA
<213> ORGANISM: Danio rerio

<400> SEQUENCE: 80
gagccatatc ttgcccacga agg                                           23

<210> SEQ ID NO 81
<211> LENGTH: 24
<212> TYPE: DNA
<213> ORGANISM: Danio rerio

<400> SEQUENCE: 81
aaatctccaa ccactccacc ttcg                                          24
```

```
<210> SEQ ID NO 82
<211> LENGTH: 24
<212> TYPE: DNA
<213> ORGANISM: Danio rerio

<400> SEQUENCE: 82
tgggcaagat atggctcacg ttat                                    24

<210> SEQ ID NO 83
<211> LENGTH: 48
<212> TYPE: DNA
<213> ORGANISM: Danio rerio

<400> SEQUENCE: 83
gttttcttac gcggttgttg gatgaaatct ccaaccactc caccttcg          48

<210> SEQ ID NO 84
<211> LENGTH: 48
<212> TYPE: DNA
<213> ORGANISM: Danio rerio

<400> SEQUENCE: 84
tgggcaagat atggctcacg ttattcatca tcttccgcat tgttttga          48

<210> SEQ ID NO 85
<211> LENGTH: 23
<212> TYPE: DNA
<213> ORGANISM: Danio rerio

<400> SEQUENCE: 85
gttcctgtag agagggatga agg                                     23

<210> SEQ ID NO 86
<211> LENGTH: 24
<212> TYPE: DNA
<213> ORGANISM: Danio rerio

<400> SEQUENCE: 86
acggatactt catggtgccc ttca                                    24

<210> SEQ ID NO 87
<211> LENGTH: 24
<212> TYPE: DNA
<213> ORGANISM: Danio rerio

<400> SEQUENCE: 87
tccctctcta caggaacgga gact                                    24

<210> SEQ ID NO 88
<211> LENGTH: 23
<212> TYPE: DNA
<213> ORGANISM: Danio rerio

<400> SEQUENCE: 88
ggagagggag atcagatcga tgg                                     23

<210> SEQ ID NO 89
<211> LENGTH: 23
<212> TYPE: DNA
<213> ORGANISM: Danio rerio

<400> SEQUENCE: 89
gtcacagcag agttcacttt agg                                     23
```

<210> SEQ ID NO 90
<211> LENGTH: 48
<212> TYPE: DNA
<213> ORGANISM: Danio rerio

<400> SEQUENCE: 90
gctccagtcc actaactcca tctgtgatca tgcatggaga atatggga         48

<210> SEQ ID NO 91
<211> LENGTH: 48
<212> TYPE: DNA
<213> ORGANISM: Danio rerio

<400> SEQUENCE: 91
acccgcctag agaacaaata cgatgtgact ttggccctct accaaaga         48

<210> SEQ ID NO 92
<211> LENGTH: 23
<212> TYPE: DNA
<213> ORGANISM: Danio rerio

<400> SEQUENCE: 92
gtcaaagcgc agcctcttca ggg                                    23

<210> SEQ ID NO 93
<211> LENGTH: 48
<212> TYPE: DNA
<213> ORGANISM: Danio rerio

<400> SEQUENCE: 93
atggacggac aagatgaagc agacggaagg tgggagtcat gatcagtt         48

<210> SEQ ID NO 94
<211> LENGTH: 23
<212> TYPE: DNA
<213> ORGANISM: Danio rerio

<400> SEQUENCE: 94
gtttccctgt ggtgctgggt tgg                                    23

<210> SEQ ID NO 95
<211> LENGTH: 23
<212> TYPE: DNA
<213> ORGANISM: Danio rerio

<400> SEQUENCE: 95
gtctggcacg aggagcacaa ggg                                    23

<210> SEQ ID NO 96
<211> LENGTH: 48
<212> TYPE: DNA
<213> ORGANISM: Danio rerio

<400> SEQUENCE: 96
tgttcgtgtg actacaatgg atgccgagct ggagtttgcc atccaacc         48

<210> SEQ ID NO 97
<211> LENGTH: 48
<212> TYPE: DNA
<213> ORGANISM: Danio rerio

<400> SEQUENCE: 97
caagggcatg ttgaggtaca gacaatggaa tgtgctcttg ctattttt       48

<210> SEQ ID NO 98
<211> LENGTH: 23
<212> TYPE: DNA
<213> ORGANISM: Danio rerio

<400> SEQUENCE: 98
ggatgtgatc caagggaaga tgg                                  23

<210> SEQ ID NO 99
<211> LENGTH: 24
<212> TYPE: DNA
<213> ORGANISM: Danio rerio

<400> SEQUENCE: 99
aaaatgtgga tgtgatccaa ggga                                 24

<210> SEQ ID NO 100
<211> LENGTH: 23
<212> TYPE: DNA
<213> ORGANISM: Danio rerio

<400> SEQUENCE: 100
agatggtggt gctgcaggct tca                                  23

<210> SEQ ID NO 101
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 101 gcttttgga ctaaacagac gccatg                                26

<210> SEQ ID NO 102
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 102
cttgtgcgta cacagctcca cg                                   22

<210> SEQ ID NO 103
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 103
cgatgttata cttgcttctt tttagttttg tacatat                   37

<210> SEQ ID NO 104
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 104
catctttgag cagtggttga ggaga                                25

<210> SEQ ID NO 105
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 105
cacctggatc ctgtaaatat gcatattcat atc                                33

<210> SEQ ID NO 106
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 106
ggtctttcag tcagcgagtt taatgtc                                       27

<210> SEQ ID NO 107
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 107
catttcagtg ctggtagcag actg                                          24

<210> SEQ ID NO 108
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 108
gcaggactga gacggtggta                                               20

<210> SEQ ID NO 109
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 109
caaatgcatc gtagcaaacg                                               20

<210> SEQ ID NO 110
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 110
aaggacaagg atcctgagtt tg                                            22

<210> SEQ ID NO 111
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 111
gctttgcatc acaacctcaa                                           20

<210> SEQ ID NO 112
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 112
agccagcttc tggatcagtg                                           20

<210> SEQ ID NO 113
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 113
ggggaggtgt gggaggtttt                                           20

<210> SEQ ID NO 114
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 114
ttccttcatt cattcattga ca                                        22

<210> SEQ ID NO 115
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 115
cgtgtgattg acagggtcac                                           20

<210> SEQ ID NO 116
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 116
cagatgccac acttcgcgt                                            19

<210> SEQ ID NO 117
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 117
cgatgttata cttgcttctt tttagttttg tacatat                        37

```
<210> SEQ ID NO 118
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 118
gttttgctaa tcctgagacg ggtttg                                          26

<210> SEQ ID NO 119
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 119
ctgtcaataa aagcatgatg tatgatgaaa atgg                                 34

<210> SEQ ID NO 120
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 120
atcatctcat tcgtcaatgg agacttcag                                       29

<210> SEQ ID NO 121
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 121
cacagtgtgg cagtgagcat tc                                              22

<210> SEQ ID NO 122
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 122
ctgaagaaca actgggagtg tcgc                                            24

<210> SEQ ID NO 123
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 123
ttacatatcc agagcgccgt aggg                                            24

<210> SEQ ID NO 124
<211> LENGTH: 22
<212> TYPE: DNA
<213> ORGANISM: Artificial Sequence
<220> FEATURE:
<223> OTHER INFORMATION: synthetic oligonucleotide
```

<400> SEQUENCE: 124
atggtgtcta agggcgaaga gc                                      22

<210> SEQ ID NO 125
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 125
agcttcaggg ccatgtcgc                                          19

<210> SEQ ID NO 126
<211> LENGTH: 99
<212> TYPE: DNA
<213> ORGANISM: Artificial Sequence
<220> FEATURE:
<223> OTHER INFORMATION: synthetic oligonucleotide

<400> SEQUENCE: 126
ggatccggag ccacgaactt ctctctgtta aagcaagcag gagacgtgga agaaaacccc    60
ggtccttcta gaaagctact gtcttctatc gaacaagca                          99

<210> SEQ ID NO 127
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 127
gcatccatgg taatttattt agcagtagat agctatattg tgtgaaacgc              50

<210> SEQ ID NO 128
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 128
agacatacta gtatggtgag caagggcgag gagctg                       36

<210> SEQ ID NO 129
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 129
tggatcctcg agttacttgt acagctcgt                               29

<210> SEQ ID NO 130
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 130
cgctgcctcg agggcgcgcc tctagaacta tag                          33

```
<210> SEQ ID NO 131
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 131
agccatacta gtaggaccgg ggttttctt                                    29

<210> SEQ ID NO 132
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 132
tgatacacgc aggtgcgcaa cgcaattaat gtgagtt                           37

<210> SEQ ID NO 133
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 133
atcctgtggc aggtccattc gccattcagg ctgc                              34

<210> SEQ ID NO 134
<211> LENGTH: 50
<212> TYPE: DNA
<213> ORGANISM: Artificial Sequence
<220> FEATURE:
<223> OTHER INFORMATION: synthetic oligonucleotide)

<400> SEQUENCE: 134
gggaggcgtt cgggccacag cggacacgca ggtgcgcaac gcaattaatg              50

<210> SEQ ID NO 135
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 135
ctgatcggat cctgtggcag gtccattcg                                    29

<210> SEQ ID NO 136
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 136
gtacatgaat tcgggaggcg ttcgggccac ag                                32

<210> SEQ ID NO 137
<211> LENGTH: 24
<212> TYPE: DNA
<213> ORGANISM: Artificial Sequence
<220> FEATURE:
<223> OTHER INFORMATION: synthetic oligonucleotide
```

```
<400> SEQUENCE: 137
cgttgtctag caaggaagtg aaga                                              24

<210> SEQ ID NO 138
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 138
gggaggcgtt cgggccacag cggagaagag catattcaat gtcg                        44

<210> SEQ ID NO 139
<211> LENGTH: 35
<212> TYPE: DNA
<213> ORGANISM: Artificial Sequence
<220> FEATURE:
<223> OTHER INFORMATION: synthetic oligonucleotide)

<400> SEQUENCE: 139
tgcagccatg gcgttgtcta gcaaggaagt gaaga                                  35

<210> SEQ ID NO 140
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 140
tcgagcggcc gagatcccat cgctagcggg                                        30

<210> SEQ ID NO 141
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 141
cttaatcagt tcctcgccct tag                                               23

<210> SEQ ID NO 142
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 142
gagaacatgc acatgaagct gtac                                              24

<210> SEQ ID NO 143
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 143
aatacgcaaa ccgcctctcc                                                   20

<210> SEQ ID NO 144
<211> LENGTH: 17
```

```
<212> TYPE: DNA
<213> ORGANISM: Artificial Sequence
<220> FEATURE:
<223> OTHER INFORMATION: synthetic oligonucleotide

<400> SEQUENCE: 144
gggcgcacat ccgcttc                                                    17

<210> SEQ ID NO 145
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 145
tttaaaagtc aaaccaccat gactg                                           25

<210> SEQ ID NO 146
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 146
ctggcagttc cttcctgtta a                                               21

<210> SEQ ID NO 147
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 147
atatgtggcg cgccacggac tgttaccact tcacg                                35

<210> SEQ ID NO 148
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 148
acaacgccat ggtaatttat ttagc                                           25

<210> SEQ ID NO 149
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 149
acagatctct cgagccgccc c                                               21

<210> SEQ ID NO 150
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 150
```

```
attcccgggg tcgacctcga                                               20
```

<210> SEQ ID NO 151
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 151

```
ggagagagct gcacaagagg gc                                            22
```

<210> SEQ ID NO 152
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 152

```
gatatcgcta gcaccggtgc ggccgcgttt aaacactagt cccggggac aacgcccaag    60 aatcag                                                              66
```

<210> SEQ ID NO 153
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 153

```
cccgggacta gtgtttaaac gcggccgcac cggtgctagc gatatctgca ggggattgag   60
caggtg                                                              66
```

<210> SEQ ID NO 154
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 154

```
agcattacgg caactgagct                                               20
```

<210> SEQ ID NO 155
<211> LENGTH: 4104
<212> TYPE: DNA
<213> ORGANISM: Streptococcus pyogenes

<400> SEQUENCE: 155

```
atggataaga aatactcaat aggcttagat atcggcacaa atagcgtcgg atgggcggtg   60
atcactgatg attataaggt tccgtctaaa aagttcaagg ttctgggaaa tacagaccgc  120
cacagtatca aaaaaaatct tatagggct cttttatttg gcagtggaga gacagcggaa   180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt ctttttttggt ggaagaagac aagaagcatg aacgtcatcc tatttttgga  360
aatatagtag atgaagttgc ttatcatgag aaatatccaa ctatctatca tctgcgaaaa  420
aaattggcag attctactga taaagcggat ttgcgcttaa tctatttggc cttagcgcat  480
atgattaagt ttcgtggtca ttttttgatt gagggagatt taaatcctga taatagtgat  540
```

```
gtggacaaac tatttatcca gttggtacaa atctacaatc aattatttga agaaaaccct      600
attaacgcaa gtagagtaga tgctaaagcg attctttctg cacgattgag taaatcaaga      660
cgattagaaa atctcattgc tcagctcccc ggtgagaaga gaaatggctt gtttgggaat      720
ctcattgctt tgtcattggg attgacccct aattttaaat caaattttga tttggcagaa      780
gatgctaaat tacagctttc aaaagatact tacgatgatg atttagataa tttattggcg      840
caaattggag atcaatatgc tgatttgttt ttggcagcta agaatttatc agatgctatt      900
ttactttcag atatcctaag agtaaatagt gaaataacta aggctcccct atcagcttca      960
atgattaagc gctacgatga acatcatcaa gacttgactc ttttaaaagc tttagttcga     1020
caacaacttc cagaaaagta taagaaatc ttttttgatc aatcaaaaaa cggatatgca      1080
ggttatattg atgggggagc tagccaagaa gaattttata aatttatcaa accaatttta     1140
gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat     1260
gctattttga gaagacaaga agactttat ccattttaa aagacaatcg tgagaagatt      1320
gaaaaaatct tgacttttcg aattccttat tatgttggtc cattggcgcg tggcaatagt     1380
cgttttgcat ggatgactcg gaagtctgaa gaaacaatta ccccatggaa ttttgaagaa     1440
gttgtcgata aaggtgcttc agctcaatca tttattgaac gcatgacaaa ctttgataaa     1500
aatcttccaa atgaaaaagt actaccaaaa catagtttgc tttatgagta ttttacggtt     1560
tataacgaat tgacaaaggt caaatatgtt actgagggaa tgcgaaaacc agcatttctt     1620
tcaggtgaac agaagaaagc cattgttgat ttactcttca aaacaaatcg aaaagtaacc     1680
gttaagcaat taaagaaga ttattttcaaa aaaatagaat gttttgatag tgttgaaatt     1740
tcaggagttg aagatagatt taatgcttca ttaggcgcct accatgattt gctaaaaatt     1800
attaaagata aagattttt ggataatgaa gaaaatgaag atatcttaga ggatattgtt      1860
ttaacattga ccttatttga agataggggg atgattgagg aaagacttaa aacatatgct     1920
cacctctttg atgataagt gatgaaacag cttaaacgtc gccgttatac tggttgggga     1980
cgtttgtctc gaaaattgat taatggtatt agggataagc aatctggcaa aacaatatta     2040
gattttttga aatcagatgg ttttgccaat cgcaatttta tgcagctgat ccatgatgat     2100
agtttgacat ttaagaaga tattcaaaaa gcacaggtgt ctggacaagg ccatagttta     2160
catgaacaga ttgctaactt agctggcagt cctgctatta aaaaaggtat tttacagact     2220
gtaaaaattg ttgatgaact ggtcaaagta atggggcata agccagaaaa tatcgttatt     2280
gaaatggcac gtgaaaatca gacaactcaa aagggccaga aaattcgcg agagcgtatg      2340 aaacgaatcg aagaaggtat caagaattaa ggaagtcaga tcttaaaga gcatcctgtt     2400 gaaaatactc aattgcaaaa tgaaaagctc tatctctatt atctacaaaa tggaagagac     2460
atgtatgtgg accaagaatt agatattaat cgtttaagtg attatgatgt cgatcacatt     2520
gttccacaaa gtttcattaa agacgattca atagacaata aggtactaac gcgttctgat     2580
aaaaatcgtg gtaaatcgga taacgttcca agtgaagaag tagtcaaaaa gatgaaaaac     2640
tattggagac aacttctaaa cgccaagtta atcactcaac gtaagtttga aatttaacg      2700 aaagctgaac gtggaggttt gagtgaactt gataaagctg gttttatcaa acgccaattg     2760
gttgaaactc gccaaatcac taagcatgtg gcacaaattt tggatagtcg catgaatact     2820
aaatacgatg aaaatgataa acttattcga gaggttaaag tgattacctt aaaatctaaa     2880
```

```
ttagtttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttctt ttactctaat     3120 atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca agtattgtc catgccccaa gtcaatattg tcaagaaaac agaagtacag     3300
acaggcggat tctccaagga gtcaatttta ccaaaaagaa attcggacaa gcttattgct    3360
cgtaaaaaag actgggatcc aaaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaaaga agttcctttg aaaaaaatcc gattgacttt    3540
ttagaagcta aaggatataa ggaagttaaa aaagacttaa tcattaaact acctaaatat    3600 agtcttttg agttagaaaa cggtcgtaaa cggatgctgg ctagtgccgg agaattacaa     3660
aaaggaaatg agctggctct gccaagcaaa tatgtgaatt ttttatattt agctagtcat    3720
tatgaaaagt tgaagggtag tccagaagat aacgaacaaa aacaattgtt tgtggagcag    3780
cataagcatt atttagatga gattattgag caaatcagtg aattttctaa gcgtgttatt    3840
ttagcagatg ccaatttaga taaagttctt agtgcatata caaacatag agacaaacca    3900 atacgtgaac aagcagaaaa tattattcat ttatttacgt tgacgaatct tggagctccc    3960
gctgctttta aatattttga tacaacaatt gatcgtaaac gatatacgtc tacaaaagaa    4020
gttttagatg ccactcttat ccatcaatcc atcactggtc tttatgaaac acgcattgat    4080
ttgagtcagc taggaggtga ctga                                           4104
```

<210> SEQ ID NO 156
<211> LENGTH: 1368
<212> TYPE: PRT
<213> ORGANISM: Streptococcus pyogenes

<400> SEQUENCE: 156

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
```

-continued

```
              995                 1000                1005
Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```